US006287854B1

(12) United States Patent
Spurr et al.

(10) Patent No.: US 6,287,854 B1
(45) Date of Patent: Sep. 11, 2001

(54) DIAGNOSIS OF SUSCEPTIBILITY TO CANCER AND TREATMENT THEREOF

(75) Inventors: Nigel K Spurr, Little Hallingbury; Ian C Gray, Peterbrough; Lorna M Stewart, Surbiton, all of (GB)

(73) Assignee: Imperial Cancer Research Technology Limited, London (GB)

( * ) Notice: Subject to any disclaimer, the term of this patent is extended or adjusted under 35 U.S.C. 154(b) by 0 days.

(21) Appl. No.: 08/906,156

(22) Filed: Aug. 5, 1997

Related U.S. Application Data

(60) Provisional application No. 60/042,655, filed on Apr. 2, 1997, and provisional application No. 60/033,147, filed on Dec. 13, 1996.

(30) Foreign Application Priority Data

Oct. 22, 1996 (GB) .................................... PCT/96GB/02588

(51) Int. Cl.$^7$ .............................. C12N 15/85; C12Q 1/68; C07H 21/04; C07K 5/00

(52) U.S. Cl. .................. 435/320.1; 435/69.1; 435/172.3; 435/325; 435/252.33; 536/23.5; 536/24.31; 536/24.33; 424/280.1; 530/300; 530/350

(58) Field of Search .............................. 435/320.1, 172.3, 435/69.1, 325, 252.3, 252.33; 536/23.1, 23.5, 24.3, 24.33, 24.31; 424/280.1; 530/350, 300

(56) References Cited

U.S. PATENT DOCUMENTS 5,658,730 * 8/1997 McGill et al. .......................... 435/6
5,700,657 * 12/1997 Beaudry et al. ..................... 435/69.1

FOREIGN PATENT DOCUMENTS

| 2013430 | 3/1990 | (CA) . |
|---|---|---|
| WO 94/24308 | 10/1994 | (WO) . |
| 95/22624 | 8/1995 | (WO) . |
| 95/32214 * | 11/1995 | (WO) . |
| WO 96/14877 | 5/1996 | (WO) . |
| WO 96/21671 | 7/1996 | (WO) . |
| WO 96/22360 | 7/1996 | (WO) . |
| WO 96/34951 | 11/1996 | (WO) . |
| WO 96 39435 | 12/1996 | (WO) . |
| 97/15686 | 5/1997 | (WO) . |
| WO 98/33907 | 8/1998 | (WO) . |
| WO 98/34624 | 8/1998 | (WO) . |

OTHER PUBLICATIONS

M.A. Pershouse et al., "Allelic Mapping of a Tumor Suppressing Region on Chromosome 10q in Human Glioblastomas" Abstract Univ. of Texas M.D. Anderson Cancer Center, Houston, TX.
Biotechnology Business News Dec. 12, 1996, pp. 11–12, "Scientist find susceptibility locus for prostrate cancer".
Scrip "Myriad/Anderson researchers identify glioma gene" Mar. 12, 1997.
Lundgren (1992) Genes Chrom. Cancer 4, 16–24.
Arps (1993) Genes Chrom. Cancer 66, 93–99.
Cannon–Albright & Eeles (1995) Nature Genetics 9, 336–338.
Sakr (1994) Cancer Res 54, 3273–3277.
Eagle (1995) Nature Genetics 9, 249–255.
Zenklusen (1994) Cancer Res 54 6370–6373.
HSC01F101, Feb. 12, 1995, Submitted (Jan. 19, 1995) to EMBL/GenBank/DDBJ databases, C.R. Acad. Sci. III, Sci. Vie 318, 263–272 (1995).
HSC01F102, Jan. 28, 1995, Submitted(Jan. 19, 1995) to the EMBL/GenBank/DDJB databases, C.R. Acad. Sci., III, Sci. Vie 318, 263–272 (1995).
Massenkeil et al, Anticancer–Res 1994 Nov.–Dec. 14(6B): 2785–90 (MEDLINE abstract).
Latil et al, Genes–Chromosom–Cancer 1994 Oct.; 11(2):119–25 (MEDLINE abstract).
Debruyne et al, Scand–J–Urol–Nephrol–Suppl 1994; 162:65–71 (MEDLINE abstract).
Phillips et al, Br J Urol 1994 Apr. 73(4): 390–5 (MEDLINE abstract).
Gao et al Oncogene 1994 Oct. 9(10): 2999–3003 (MEDLINE abstract).
Sakr et al, Cancer Res (1994) Jun. 15: 54(12): 3273–7 (MEDLINE abstract).
Macoska et al, Genes Chromosom Cancer 1993 Oct. 8(2): 88–97 (MEDLINE abstract).
Macoska et al, J Urol 1992 Apr.: 147(4): 1142–6 (MEDLINE abstract).
Kunimi et al, Nippon Hinyokika Gakkai Zasshi 1991 Dec. 82(12) 1930–8 (MEDLINE abstract).
Kunimi et al, Genomics 1991 Nov.; 11(3):530–6 (MEDLINE abstract).
Isaacs et al, Cancer Surv 1991; 11: 15–24 (MEDLINE abstract).
Lundgren, Scan J Urol Nephrol Suppl 1991; 136: 1–35 (MEDLINE abstract).
Carter et al PNAS (USA) 1990 Nov.; 87(22): 8751–5 (MEDLINE abstract).
Babu et al, Cancer Genet Cytogenet 1990 Aug. 1; 48(1): 83–7 (MEDLINE abstract).

(List continued on next page.)

Primary Examiner—Stephanie Zitomer
(74) Attorney, Agent, or Firm—Nixon & Vanderhye P.C.

(57) ABSTRACT

A method for determining the susceptibility of a patient to cancer comprising the steps (i) obtaining a sample containing nucleic acid derived from the patient; and (ii) contacting the said nucleic acid with a nucleic acid capable of selectively hybridising to the region of human chromosome 10 which region is bounded by DNA defined by the markers D10S541 and D10S215. A nucleic acid capable of selectively hybridising to the region of human chromosome 10 which region is bounded by DNA defined by the markers D10S541 and D10S215 provided that the nucleic acid is not any one of certain YACs, BACs, PACs or ESTs defined herein. Preferably the said nucleic acid is a prostate tumour suppressor gene.

30 Claims, 20 Drawing Sheets

OTHER PUBLICATIONS

Brothman et al, Caner Res 1990 Jun. 15; 50(12): 3795–803 (MEDLINE abstract).

Frayling et al (May 1997) Poster presented at the Cancer Family Study Group meeting on May 15, 1997: "Allelic loss in colorectal cancer at the Cowden's Disease/Juvenile Polyposis locus on 10q22".

Steck et al (Apr. 1997) Nature Genetics 15, 356–362.

Li et al (Mar. 1997) Science 275, 1943–1947.

Gyapay et al (1994) Nature Genetics 7, 246–339.

Gao (1994) Oncogene 9, 2999–3003.

Nihei et al (1995) Genes Chromosomes & Cancer 14(2) 112–119.

Hillier (1995) Database EMBL EST *H. sapiens* cDNA clone 126556 5' "WasU–Merck EST project" accession R06763. Table 13.

Hillier (1995) Database EMBL EST *H. sapiens* cDNA clone 126556 5' "WasU–Merck EST project" accession R06814. Table 14.

GenBank/EMBL Accession No. U96180, Li et al., TEP1, encoded by a candidate tumor suppressor locus, is a novel protein tyrosine phosphatase regulated by transforming growth factor beta, Apr. 2, 1997.*

Adams et al (1993) Database EMBL EST *H. sapiens* cDNA clone HFBCS42 "3400 expressed sequence tags identify diversity of transcripts from human brain" acccession T05157. Table 16.

Hillier (1995) Database EMBL EST *H. sapiens* cDNA clone 81420 5' "WasU–Merck EST project" accession T60214. Table 17.

Gray et al (1995) Cancer Res. 55, 4800–4803.

Gray et al (1995) Am J Human Genet 57(4), A65–346.

Rasheed et al (1995) Oncogene 10, 2243–2246.

Moschonas (1996) Cytogenet. Cell Genet. 72, 99–112.

Gray (1995) GDB citation 636618.

Trybus et al (1996) Cancer Res 56, 2263–2267.

Albarosa (1996) Am J. Hum. Genet. 58, 1260–1267.

Lacombe et al (1996) Int. J. Cancer 69, 110–113.

Marsh et al (1997) Cancer res. 57, 500–503.

Gray et al (1995) Genomics 28, 328–332.

Li et al (1997) Cancer Research 57, 2124–2129.

Marsh et al Nature Genetics, Aug. 16, 1997, 16, 333–334.

Gray et al (1997) Genomics 43, 85–88.

D. Cohen et al. "A First–Generation Physical Map of the Human Genome", Nature, vol. 366, Dec. 16, 1993, pp. 698–701.

J. Weissenbach et al., "A Second–Generation Linkage Map of the Human Genome", Nature, vol. 359, Oct. 29, 1992, pp 794–801.

* cited by examiner

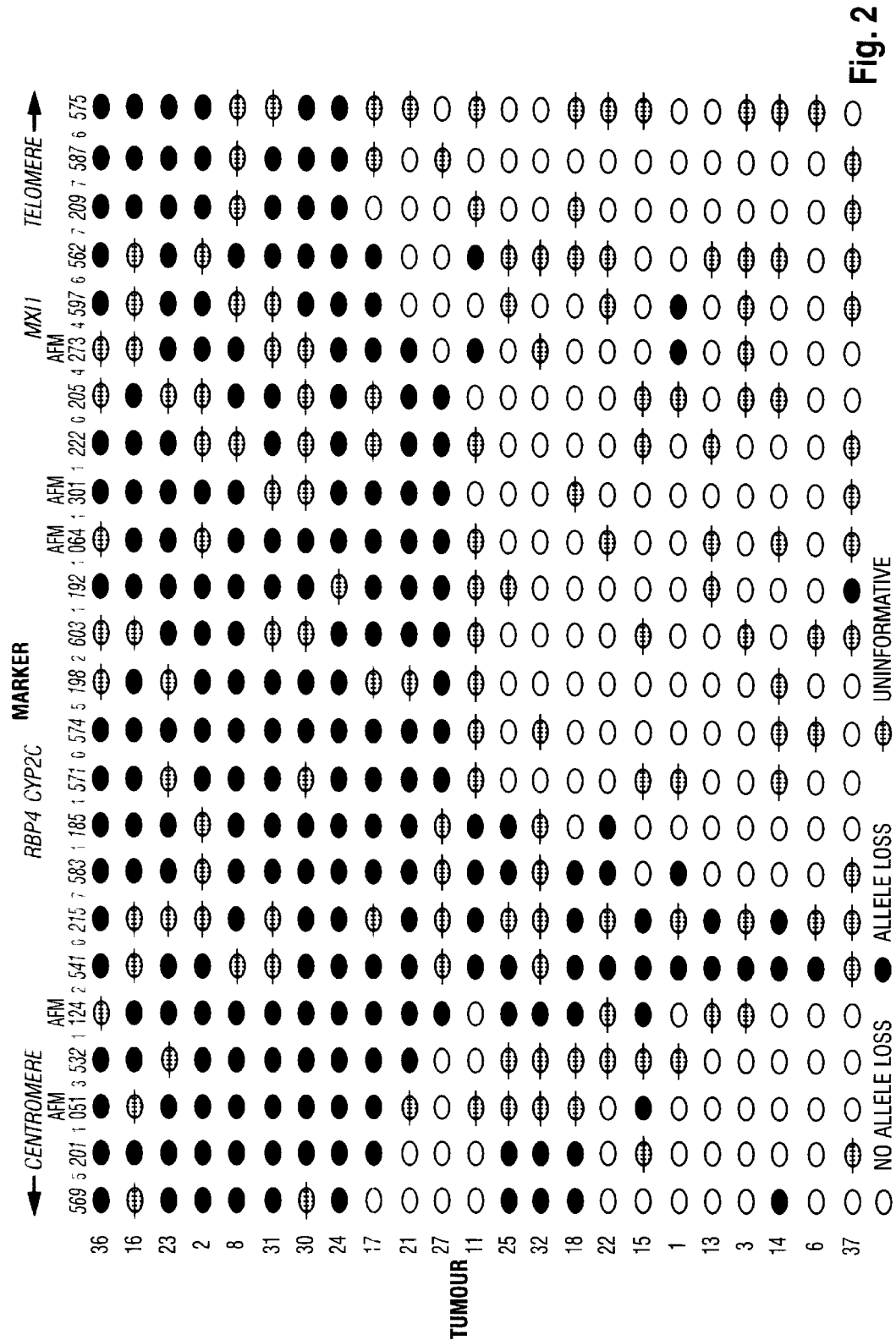

```
   1  CGGCCGCGGC GGCTGCAGCT CCAGGGAGGG GGTCTGAGTC GCCTGTCACC
  51  ATTTCCAGGG CTGGGAACGC CGGAGAGTTG GTCTCTCCCC TTCTACTGCC
 101  TCCAACACGG CGGCGGCGGC GGCGGCACAT CCAGGGACCC GGGCCGGTTT
 151  TAAACCTCCC GTCCGCCGCC GCCGCACCCC CCGTGGCCCG GCTCCGGAG
 201  GCCGCCGGCG GAAGCAGCCG TTCGGAGGAT TATTCGTCTT CTCCCCATTC
 251  CGCTGCCGCC GCTGCCAGGC CTCTGGCTGC TGAGGAGAAG CAGGCCCAGT
 301  CGCTGCAACC ATCCAGCAGC CGCCGCAGCA GCCATTACCC GGCTGCGGTC
 351  CAGAGCCAAG CGGCGGCAGA GCGAGGGGCA TCAGCTACCG CCAAGTCCAG
 401  AGCCATTTCC ATCCTGCAGA GAAGCCCCG CCACCAGCAG CTTCTGCCAT
 451  CTCTCTCCTC CTTTTCTTC AGCCACAGGC TCCCAGACAT GACAGCCATC
 501  ATCAAAGAGA TCGTTAGCAG AAACAAAAGG AGATATCAAG AGGATGGATT
                     ss
 551  CGACTTAGAC TTGACCTATA TTTATCCAAA CATTATTGCT ATGGGATTTC
 601  CTGCAGAAAG ACTTGAAGGC GTATACAGGA ACAATATTGA TGATGTAGTA
                                                         ss
 651  AGGTTTTTGG ATTCAAAGCA TAAAAACCAT TACAAGATAT ACAATCTTTG
                                                       ss
 701  TGCTGAAAGA CATTATGACA CCGCCAAATT TAATTGCAGA GTTGCACAAT
 751  ATCCTTTTGA AGACCATAAC CCACCACAGC TAGAACTTAT CAAACCCTTT
 801  TGTGAAGATC TTGACCAATG GCTAAGTGAA GATGACAATC ATGTTGCAGC
 851  AATTCACTGT AAAGCTGGAA AGGGACGAAC TGGTGTAATG ATATGTGCAT
 901  ATTTATTACA TCGGGGCAAA TTTTTAAAGG CACAAGAGGC CCTAGATTTC
                                               ss
 951  TATGGGGAAG TAAGGACCAG AGACAAAAAG GGAGTAACTA TTCCCAGTCA
1001  GAGGCGCTAT GTGTATTATT ATAGCTACCT GTTAAAGAAT CATCTGGATT
1051  ATAGACCAGT GGCACTGTTG TTTCACAAGA TGATGTTTGA AACTATTCCA
                                ss
1101  ATGTTCAGTG GCGGAACTTG CAATCCTCAG TTTGTGGTCT GCCAGCTAAA
1151  GGTGAAGATA TATTCCTCCA ATTCAGGACC CACACGACGG AAGACAAGT
1201  TCATGTACTT TGAGTTCCCT CAGCCGTTAC CTGTGTGTGG TGATATCAAA
                                                     ss
1251  GTAGAGTTCT TCCACAAACA GAACAAGATG CTAAAAAAGG ACAAAATGTT
1301  TCACTTTTGG GTAAATACAT TCTTCATACC AGGACCAGAG GAAACCTCAG
1351  AAAAAGTAGA AAATGGAAGT CTATGTGATC AAGAAATCGA TAGCATTTGC
1401  AGTATAGAGC GTGCAGATAA TGACAAGGAA TATCTAGTAC TTACTTTAAC
1451  ARAAAATGAT CTTGACAAAG CAAATAAAGA CAAAGCCAAC CGATACTTTT
                 ss
1501  CTCCAAATTT TAAGGTGAAG CTGTACTTCA CAAAAACAGT AGAGGAGCCG
```

Fig. 6-1

```
1551  TCAAATCCAG AGGCTAGCAG TTCAACTTCT GTAACACCAG ATGTTAGTGA
1601  CAATGAACCT GATCATTATA GATATTCTGA CACCACTGAC TCTGATCCAG
1651  AGAATGAACC TTTTGATGAA GATCAGCATA CACAAATTAC AAAAGTCtga
1701  atttttcttt atcaagaggg ataaacacc atgaaaataa acttgaataa
1751  actgaaaaaa aaaaaaaaa aaa
```

Fig. 6-2

```
TRANSLATION
    1  AAAAAAPGRG SESPVTISRA GNAGELVSPL LLPPTRRRRR RHIQGPGPVL
   51  NLPSAAAAPP VARAPEAAGG SSRSEDYSSS PHSAAAAARP LAAEEKQAQS
  101  LQPSSSRRSS HYPAAVQSQA AAERGASATA KSRAISILQK KPRHQQLLPS
  151  LSSFFFSHRL PDMTAIIKEI VSRNKRRYQE DGFDLDLTYI YPNIIAMGFP
  201  AERLEGVYRN NIDDVVRFLD SKHKNHYKIY NLCAERHYDT AKFNCRVAQY
  251  PFEDHNPPQL ELIKPFCEDL DQWLSEDDNH VAAIHCKAGK GRTGVMICAY
  301  LLHRGKFLKA QEALDFYGEV RTRDKKGVTI PSQRRYVYYY SYLLKNHLDY
  351  RPVALLFHKM MFETIPMFSG GTCNPQFVVC QLKVKIYSSN SGPTRREDKF
  401  MYFEFPQPLP VCGDIKVEFF HKQNKMLKKD KMFHFWVNTF FIPGPEETSE
  451  KVENGSLCDQ EIDSICSIER ADNDKEYLVL TLTXNDLDKA NKDKANRYFS
  501  PNFKVKLYFT KTVEEPSNPE ASSSTSVTPD VSDNEPDHYR YSDTTDSDPE
  551  NEPFDEDQHT QITKV*IFFY QEG*NTMKIN LNKLKKKKKK
```

Fig. 7

EXON 1

```
  1 CGGCCGCGGC GGCTGCAGCT CCAGGGAGGG GGTCTGAGTC GCCTGTCACC
 51 ATTTCCAGGG CTGGGAACGC CGGAGAGTTG GTCTCTCCCC TTCTACTGCC
101 TCCAACACGG CGGCGGCGGC GGCGGCACAT CCAGGGACCC GGGCCGGTTT
151 TAAACCTCCC GTCCGCCGCC GCCGCACCCC CCGTGGCCCG GGCTCCGGAG
201 GCCGCCGGCG GAAGCAGCCG TTCGGAGGAT TATTCGTCTT CTCCCCATTC
251 CGCTGCCGCC GCTGCCAGGC CTCTGGCTGC TGAGGAGAAG CAGGCCCAGT
301 CGCTGCAACC ATCCAGCAGC CGCCGCAGCA GCCATTACCC GGCTGCGGTC
351 CAGAGCCAAG CGGCGGCAGA GCGAGGGGCA TCAGCTACCG CCAAGTCCAG
401 AGCCATTTCC ATCCTGCAGA AGAAGCCCCG CCACCAGCAG CTTCTGCCAT
451 CTCTCTCCTC CTTTTTCTTC AGCCACAGGC TCCCAGACAT GACAGCCATC
501 ATCAAAGAGA TCGTTAGCAG AAACAAAAGG AGATATCAAG AGGATGGATT
551 CGACTTAGAC TTGACCTgta tccatttctg cggctgctcc tctttacctt
601 tctgtcactc tcttagaacg tgggagtaga cggatgcgaa aatgtccgta
651 gtttgggtga ctataacatt taaccctggt caggttgcta ggtcatatat
701 tttgtgtttc ctttctgtgt attcaaccta gggtgtgttt ggctagacgg
751 aactcttgcc tggttgcaag tgtcaagcca ccgattgctt tcttaggcta
801 tctatatggt ctcttcctga gggctattgt ccgttaatac agaatacagt
851 aaggagagga cagcgatcct a
```

Fig. 8

EXON 2A

```
tcgnatccnt acccgttcgt acgagaatcg ctgtccctct cccttctaat gttttaaaaa    60
gtattctttt agtttgattg ctgcatattt cagatatttc tttccttaac taaagtaact   120
cagATATTTA TCCAAACATT ATTGCTATGG GATTTCCTGC AGAAAGACTT GAAGGCGTAT   180
ACAGGAACAA TATTGATGAT GTAGTAAGGt aagaatgctt tgattttcta tttcaaatat   240
tgatgtttat attcatgttg tgttttcatt tagaaaagat ttctaagcca cagaaaaaga   300
tactttgtga tgtaaactat tattgtagtg ctctataatc atttttggc ttaccgtacc    360
taatggactt caggggata cagttcattt gataagaact gaccttatac attacataat    420
caggtactta tgtgataagg anaggacaca tctcgtacaa ngagg                   465
```

EXON 2B

```
ccgttcgtac gagaatcgct gtcctctcct tctcattttt gttaatggtg gcttttgtt    60
tgtttgtttt gttttaaggT TTTGGATTC AAAGCATAAA AACCATTACA AGATATACAA   120
TCTgtaagta tgttttctta tttgtatgct tgcaaatatc ttctaaaaca actattaagt   180
gaaagttatn tgcttgttag agtgaggtag agttaaagat acattttaac agaattgtat   240
tcctaaaccg attaagtcaa gaagtccaag agcattgtta gatcatttag aaagtgtagt   300
gatgaggtaa acattgttg gcacagattc atgttanctg atntgcttta aatganttgg    360
catntagccc atatttgagc ccataaccgt gtggtaattt gaagtgtnat tnacagtaga   420
gcttttgtta aagcactaat agcatnttcc anggaggtat aattcagagt gaatataaat   480
ttgtttatcc tgtgtcttta gagctattga ctgaaaagc tgttaggcat tntctaactg    540
t                                                                 541
```

Fig. 9

EXON 3

```
  1 taaaacacag cataatatgt gtcacattat aaagattcag gcaatgtttg
 51 ttagtattag tacttttttt tcttcctaag tgcaaaagat aactttatat
101 cacttttaaa cttttctttt agTTGTGCTG AAAGACATTA TGACACCGCC
151 AAATTTAATT GCAGaggtag gtatgaatgt actgtactat gttgtataac
201 ttaaacccga tagactgtat cttactgtca taacaataat gagtcatcca
251 gattatcgag tgagatacat atttatctta agaattatct ttaaaaattt
301 caaaaatttt aatttgactg ttgtgtttta ggaaaaagta ttgcataaag
351 ctattaatat tgtcaggaag actaaagtgc agcata
```

Fig. 10

EXON 4

```
  1 ttttctacct ctaatngctg acntatgcta ccagtccgta tagcgtaaat
 51 tcccagaata tatcctcctg aataaaatgg gggaaaataa tacctggctt
101 ccttaatgat tatatttaan acttatcaan anactatttt ctatttaaca
151 attagaaagt taagcaatac attatttttc tctggaatcc agtgtttctt
201 ttaaatacct gttaagtttg tatgcaacat ttctaaagtt acctacttgt
251 taattaaaaa ttcaanagtt tttttnctt attctgaggt tatcttttta
301 ccacAGTTGC ACAATATCCT TTGAAGACC ATAACCCACC ACAGCTAGAA
351 CTTATCAAAC CCTTTTGTGA AGATCTTGAC CAATGGCTAA GTGAAGATGA
401 CAATCATGTT GCAGCAATTC ACTGTAAAGC TGGAAAGGGA CGAACTGGTG
451 TAATGATATG TGCATATTTA TTACATCGGG GCAAATTTTT AAAGGCACAA
501 GAGGCCCTAG ATTTCTATGG GGAAGTAAGG ACCAGAGACA AAAaggtaa
551 gttatttttt gatgttttc ctttcctctt cctggatctg agaatttatt
601 ggaaaacaga ttttgggttt cttttttct tcagttttat tgaggtgtaa
651 ttgcacaagt aaaattata tataaataca atgtataata tgatgtttgg
701 atgtatgtgt atatacattg tgaa
```

Fig. 11

EXON 5

```
  1  aaggtcaaat gtctaatgta tatatgttct taaatggcta cgacccagtt
 51  accatagcaa tttagtgaaa taactataat ggaacatttt ttttcaattt
101  ggcttctctt tttttctgt ccaccAGGGA GTAACTATTC CCAGTCAGAG
151  GCGCTATGTG TATTATTATA GCTACCTGTT AAAGAATCAT CTGGATTATA
201  GACCAGTGGC ACTGTTGTTT CACAAGATGA TGTTTGAAAC TATTCCAATG
251  TTCAGTGGCG GAACTTGCAg taagtgcttg aatctcatcc ttccatgtta
301  ttgggaacag ttttcttaac catatctaga agtttacata aaaatttaga
351  aagaaattta ccacatttga aatttatgca ggagactata tttctgaagc
401  atttgaacaa attaattagc tttgttgttc aactcattgg gctaaagaag
451  ccaaaagcaa tgggttttaa tgtagtcgaa gccaaattat atttatgaaa
501  gaaatattct gtgttataac caccaaatac agcccaattc tg
```

Fig. 12

EXON 6

```
  1  actctgccac tagaagtcta attttgggac ttactattca tgaaatagga
 51  attgactttn atataagtaa taggaccctta ttttgaaggt tcaaactgga
101  gaaaatctta cattgtttat attttattt catttanttc agttgatttg
151  cttgagatca agattgcaga tacagaatcc atatttcgtg tatattgctg
201  atattaatca ttaaaatcgt ttttgacagt ttgacagtta aaggcatttc
251  cctgtgaaat aatactggta tgtatttaac catgcagATC CTCAGTTTGT
301  GGTCTGCCAG CTAAAGGTGA AGATATATTC CTCCAATTCA GGACCCACAC
351  GACGGGAAGA CAAGTTCATG TACTTTGAGT TCCCTCAGCC GTTACCTGTG
401  TGTGGTGATA TCAAAGTAGA GTTCTTCCAC AAACAGAACA AGATGCTAAA
451  AAgggtttgt actttacttt cattgggaga aatatccaaa ataaggacag
501  attanaagct ntattntatt ttatgacatg taaggaacta taatttgttt
551  tctattagat ctgccaggtg ttttgcttac tctggcattg gtgagacatt
601  atangggtaa ataatcctgt ttgaaggaan aggcctat
```

Fig. 13

EXON 7

```
  1 tttatcttag atcttgtgag attgtatttt tggtttaaaa tttgagaatt
 51 tgagtgaaga aaatcatgt gaatgaaaat gcaacagata actcagattg
101 ccttataata gtctttgtgt ttacctttat tcagaatatc aaatgatagt
151 ttattttgtt gacttttgc aaatgtttaa cataggtgac agatttnctt
201 ttttaaaaaa ataaaacatc attaattaaa tatgtcattt catttctttt
251 tcttttcttt tttttttttt tAGGACAAAA TGTTTCACTT TTGGGTAAAT
301 ACATTCTTCA TACCAGGACC AGAGGAAACC TCAGAAAAAG TAGAAAATGG
351 AAGTCTATGT GATCAAGAAA TCGATAGCAT TTGCAGTATA GAGCGTGCAG
401 ATAATGACAA GGAATATCTA GTACTTACTT TAACARAAAA TGATCTTGAC
451 AAAGCAAATA AAGACAAAGC CAACCGATAC TTTTCTCCAA ATTTTAAGgt
501 cagttaaatt aaacattttg tgggggntgg tgacttgtat gtatgtgatg
551 tgtgtttaat tctaggagta cagaaggaga ggacagcgat
```

Fig. 14

EXON 8

```
  1 ggaggcagag gttgcagtga gccaagatca tgccactgca ctccagcttg
 51 gcaacagagc aagactcttg tctccagaaa taaaaataaa taaattgtat
101 taacatcctg atagtttatc tgtttagtac ctagcaagaa agaaaatgtt
151 gaacatctta agaagagggt catttaaaag gcctcttaaa gatcatgttt
201 gttacagtgc ttaaaaatta atatgttcat ctgcaaaatg gaataaaaaa
251 tctgttaaaa atatatttca ctaaatagtt aagatgagtc atatttgtgg
301 gttttcattt taaattttct ttctctaGTG AAGCTGTACT TCACAAAAAC
351 AGTAGAGGAG CCGTCAAATC CAGAGGCTAG CAGTTCAACT TCTGTAACAC
401 CAGATGTTAG TGACAATGAA CCTGATCATT ATAGATATTC TGACACCACT
451 GACTCTGATC CAGAGAATGA ACCTTTTGAT GAAGATCAGC ATACACAAAT
501 TACAAAAGTC tgaatttttt tttatcaaga gggataaaac accatgaaaa
551 taaacttgaa taaactgaaa aaaaaaaaaa aaaaaa
```

Fig. 15

EXON 1

| | | | | | |
|---|---|---|---|---|---|
| CGGCCGCGGC | GGCTGCAGCT | CCAGGGAGGG | GGTCTGAGTC | GCCTGTCACC | ATTTCCAGGG | 60 |
| CTGGGAACGC | CGGAGAGTTG | GTCTCTCCCC | TTCTACTGCC | TCCAACACGG | CGGCGGCGGC | 120 |
| GGCGGCACAT | CCAGGGACCC | GGGCCGGTTT | TAAACCTCCC | GTCCGCCGCC | GCCGCACCCC | 180 |
| CCGTGGCCCG | GCTCCGGAG | GCCGCCGGCG | GAAGCAGCCG | TTCGGAGGAT | TATTCGTCTT | 240 |
| CTCCCCATTC | CGCTGCCGCC | GCTGCCAGGC | CTCTGGCTGC | TGAGGAGAAG | CAGGCCCAGT | 300 |
| CGCTGCAACC | ATCCAGCAGC | CGCCGCAGCA | GCCATTACCC | GGCTGCGGTC | CAGAGCCAAG | 360 |
| CGGCGGCAGA | GCGAGGGGCA | TCAGCTACCG | CCAAGTCCAG | AGCCATTTCC | ATCCTGCAGA | 420 |
| AGAAGCCCCG | CCACCAGCAG | CTTCTGCCAT | CTCTCTCCTC | CTTTTTCTTC | AGCCACAGGC | 480 |
| TCCCAGACAT | GACAGCCATC | ATCAAGAGA | TCGTTAGCAG | AAACAAAGG | AGATATCAAG | 540 |
| AGGATGGATT | CGACTTAGAC | TTGACCTGTA | TCCATTTCTG | CGGCTGCTCC | TCTTTACCTT | 600 |
| TCTGTCACTC | TCTTAGAACG | TGGGAGTAGA | CGGATGCGAA | AATGTCCGTA | GTTTGGGTGA | 660 |
| CTATAACATT | TAACCCTGGT | CAGGTTGCTA | GGTCATATAT | TTTGTGTTTC | CTTTCTGTGT | 720 |
| ATTCAACCTA | GGGTGTGTTT | GGCTAGACGG | AACTCTTGCC | TGGTTGCAAG | TGTCAAGCCA | 780 |
| CCGATTGCTT | TCTTAGGCTA | TCTATATGGT | CTCTTCCTGA | GGGCTATTGT | CCGTTAATAC | 840 |
| AGAATACAGT | AAGGAGAGGA | CAGCGATCCT | A | | | 871 |

Fig. 16

EXON 2a

| | | | | | |
|---|---|---|---|---|---|
| CTAATGTTTT | AAAAAGTATT | CTTTTAGTTT | GATTGCTGCA | TATTTCAGAT | ATTTCTTTCC | 60 |
| TTAACTAAAG | TAACTCAGAT | ATTTATCCAA | ACATTATTGC | TATGGGATTT | CCTGCAGAAA | 120 |
| GACTTGAAGG | CGTATACAGG | AACAATATTG | ATGATGTAGT | AAGGTAAGAA | TGCTTTGATT | 180 |
| TTCTATTTCA | AATATTGATG | TTTATATTCA | TGTTGTGTTT | TCATTTAGAA | AAGATTTCTA | 240 |
| AGCCACAGAA | AAAGATACTT | TGTGATGTAA | ACTATTATTG | TAGTGCTCTA | TAATCATTTT | 300 |
| TTGGCTTACC | GTACCTAATG | GACTTCAGGG | GGATACAGTT | CATTTGATAA | GAACTGACCT | 360 |
| TATACATTAC | ATAATCAGGT | ACTTATGTGA | TAAGGANAGG | ACACATCTCG | TACAANGAGG | 420 |

Fig. 17

EXON 2b

| | | | | | |
|---|---|---|---|---|---|
| CTCATTTTTG | TTAATGGTGG | CTTTTTGTTT | GTTTGTTTTG | TTTTAAGGTT | TTTGGATTCA | 60 |
| AAGCATAAAA | ACCATTACAA | GATATACAAT | CTGTAAGTAT | GTTTTCTTAT | TTGTATGCTT | 120 |
| GCAAATATCT | TCTAAAACAA | CTATTAAGTG | AAAGTTATCT | GCTTGTTAGA | GTGAGGTAGA | 180 |
| GTTAAAGATA | CATTTTAACA | GAATTGTATT | CCTAAACCGA | TTAAGTCAAG | AAGTCCAAGA | 240 |
| GCATTGTTAG | ATCATTTAGA | AAGTGTAGTG | ATGAGGTAAA | ACATTGTTGG | CACAGATTCA | 300 |
| TGTTANCTGA | TNTGCTTTAA | ATGANTTGGC | ATCTAGCCCA | TATTTGAGCC | CATAACCGTG | 360 |
| TGGTAATTTG | AAGTGTNATT | NACAGTAGAG | CTTTTGTTAA | AGCACTAATA | GCATNTTCCA | 420 |
| NGGAGGTATA | ATTCAGAGTG | AATATAAATT | TGTTTATCCT | GTGTCTTTAG | AGCTATTGAC | 480 |
| TGAAAAAGCT | GTTAGGCATT | NTCTAACTGT | | | | 510 |

Fig. 18

EXON 3.1

| | | | | | |
|---|---|---|---|---|---|
| TAAAACACAG | CATAATATGT | GTCACATTAT | AAAGATTCAG | GCAATGTTTG | TTAGTATTAG | 60
| TACTTTTTTT | TCTTCCTAAG | TGCAAAAGAT | AACTTTATAT | CACTTTTAAA | CTTTTCTTTT | 120
| AGTTGTGCTG | AAAGACATTA | TGACACCGCC | AAATTTAATT | GCAGAGGTAG | GTATGAATGT | 180
| ACTGTACTAT | GTTGTATAAC | TTAAACCCGA | TAGACTGTAT | CTTACTGTCA | TAACAATAAT | 240
| GAGTCATCCA | GATTATCGAG | TGAGATACAT | ATTTATCTTA | AGAATTATCT | TTAAAAATTT | 300
| CAAAAATTTT | AATTTACTG | TTGTGTTTTA | GGAAAAAGTA | TTGCATAAAG | CTATTAATAT | 360
| TGTCAGGAAG | ACTAAAGTGC | AGCATA | | | | 386

EXON 3.2

| | | | | | |
|---|---|---|---|---|---|
| TAAAACACAG | CATAATATGT | GTCACATTAT | AAAGATTCAG | GCAATGTTTG | TTAGTATTAG | 60
| TACTTTTTTT | TCTTCCTAAG | TGCAAAAGAT | AACTTTATAT | CACTTTTAAA | CTTTTCTTTT | 120
| AGTTGTGCTG | AAAGACATTA | TGACACCGCC | AAATTTAATT | GCAGAGGTAG | GTATGAATGT | 180
| ACTGTACTAT | GTTGTATAAC | TTAAACCCGA | TAGACTGTAT | CTTACTGTCA | TAACAATAAT | 240
| GAGTCATCCA | GATTATCGAG | TGAGATACAT | ATTTAAGAAT | TATCTTTAAA | AATTTCAAAA | 300
| ATTTTAATTT | TACTGTTGTG | TTTTAGGAAA | AAGTATTGCA | TAAAGCTATT | AATATTGTCA | 360
| GGAAGACTAA | AGTGCAGCAT | A | | | | 381

Fig. 19

EXON 4

```
TTTTCTACCT CTAATNGCTG ACNTATGCTA CCAGTCCGTA TAGCGTAAAT TCCCAGAATA        60
TATCCTCCTG AATAAAATGG GGGAAAATAA TACCTGGCTT CCTTAATGAT TATATTTAAN       120
ACTTATCAAN ANACTATTTT CTATTTAACA ATTAGAAAGT TAAGCAATAC ATTATTTTTC       180
TCTGGAATCC AGTGTTTCTT TTAAATACCT GTTAAGTTTG TATGCAACAT TTCTAAAGTT       240
ACCTACTTGT TAATTAAAAA TTCAAGAGTT TTTTTTTCTT ATTCTGAGGT TATCTTTTTA       300
CCACAGTTGC ACAATATCCT TTTGAAGACC ATAACCCACC ACAGCTAGAA CTTATCAAAC       360
CCTTTTGTGA AGATCTTGAC CAATGGCTAA GTGAAGATGA CAATCATGTT GCAGCAATTC       420
ACTGTAAAGC TGGAAGGGA CGAACTGGTG TAATGATATG TGCATATTTA TTACATCGGG        480
GCAAATTTTT AAAGGCACAA GAGGCCCTAG ATTTCTATGG GGAAGTAAGG ACCAGAGACA       540
AAAAGGTAAG TTATTTTTTG ATGTTTTCC TTTCCTCTTC CTGGATCTGA GAATTTATTG        600
GAAAACAGAT TTTGGGTTTC TTTTTTTCTT CAGTTTTATT GAGGTGTAAT TGCACAAGTA       660
AAAATTATAT ATAAATACAA TGTATAATAT GATGTTTGGA ATGTATGTGT ATATACATTG       720
TGAA                                                                    724
```

Fig. 20

EXON 5

```
AAGGTCAAAT GTCTAATGTA TATATGTTCT TAAATGGCTA CGACCCAGTT ACCATAGCAA        60
TTTAGTGAAA TAACTATAAT GGAACATTTT TTTTCAATTT GGCTTCTCTT TTTTTTCTGT       120
CCACCAGGGA GTAACTATTC CCAGTCAGAG GCGCTATGTG TATTATTATA GCTACCTGTT       180
AAAGAATCAT CTGGATTATA GACCAGTGGC ACTGTTGTTT CACAAGATGA TGTTTGAAAC       240
TATTCCAATG TTCAGTGGCG GAACTTGCAG TAAGTGCTTG AAATTCTCAT CCTTCCATGT       300
ATTGGAACAG TTTTCTTAAC CATATCTAGA AGTTTACATA AAAATTTAGA AAGAAATTTA       360
CCACATTTGA AATTTATGCA GGAGACTATA TTTCTGAAGC ATTTGAACAA ATTAATTAGC       420
TTTGTTGTTC AACTCATTGG GCTAAAGAAG CCAAAAGCAA TGGGTTTTAA TGTAGTCGAA       480
GCCAAATTAT ATTTATGAAA GAAATATTCT GTGTTATAAC CACCAAATAC AGCCCAATTC       540
TG                                                                      542
```

Fig. 21

EXON 6

```
ACTCTGCCAC TAGAAGTCTA ATTTTGGGAC TTACTATTCA TGAAATAGGA ATTGACTTTN      60
ATATAAGTAA TAGGACCTTA TTTTGAAGGT TCAAACTGGA GAAAATCTTA CATTGTTTAT     120
ATTTTTATTT CATTTANTTC AGTTGATTTG CTTGAGATCA AGATTGCAGA TACAGAATCC     180
ATATTTCGTG TATATTGCTG ATATTAATCA TTAAAATCGT TTTTGACAGT TTGACAGTTA     240
AAGGCATTTC CCTGTGAAAT AATACTGGTA TGTATTTAAC CATGCAGATC CTCAGTTTGT     300
GGTCTGCCAG CTAAAGGTGA AGATATATTC CTCCAATTCA GGACCCACAC GACGGGAAGA     360
CAAGTTCATG TACTTTGAGT TCCCTCAGCC GTTACCTGTG TGTGGTGATA TCAAAGTAGA     420
GTTCTTCCAC AAACAGAACA AGATGCTAAA AAAGGTTTGT ACTTTACTTT CATTGGGAGA     480
AATATCCAAA ATAAGGACAG ATTANAAGCT NTATTNTATT TTATGACATG TAAGGAACTA     540
TAATTTGTTT TCTATTAGAT CTGCCAGGTG TTTTGCTTAC TCTGGCATTG GTGAGACATT     600
ATANGGGTAA ATAATCCTGT TTGAAGGAAN AGGCCTAT                             638
```

Fig. 22

EXON 7

```
TTTATCTTAG ATCTTGTGAG ATTGTATTTT TGGTTTAAAA TTTGAGAATT TGAGTGAAGA      60
AAAATCATGT GAATGAAAAT GCAACAGATA ACTCAGATTG CCTTATAATA GTCTTTGTGT     120
TTACCTTTAT TCAGAATATC AAATGATAGT TTATTTGTT GACTTTTGC AAATGTTTAA      180
CATAGGTGAC AGATTTTCTT TTTTAAAAAA ATAAACATC ATTAATTAAA TATGTCATTT     240
CATTTCTTTT TCTTTTCTTT TTTTTTTTTT TAGGACAAAA TGTTTCACTT TTGGGTAAAT     300
ACATTCTTCA TACCAGGACC AGAGGAAACC TCAGAAAAG TAGAAAATGG AAGTCTATGT     360
GATCAAGAAA TCGATAGCAT TTGCAGTATA GAGCGTGCAG ATAATGACAA GGAATATCTA     420
GTACTTACTT TAACAAAAAA TGATCTTGAC AAAGCAAATA AAGACAAAGC CAACCGATAC     480
TTTTCTCCAA ATTTTAAGGT CAGTTAAATT AAACATTTTG TGGGGGTTGG TGACTTGTAT     540
GTATGTGATG TGTGTTTAAT TCTAGGAGTA CAG                                  573
```

Fig. 23

EXON 8

| | | | | | |
|---|---|---|---|---|---:|
| GGAGGCAGAG | GTTGCAGTGA | GCCAAGATCA | TGCCACTGCA | CTCCAGCTTG | GCAACAGAGC | 60 |
| AAGACTCTTG | TCTCCAGAAA | TAAAAATAAA | TAAATTGTAT | TAACATCCTG | ATAGTTTATC | 120 |
| TGTTTAGTAC | CTAGCAAGAA | AGAAAATGTT | GAACATCTTA | AGAAGAGGGT | CATTTAAAAG | 180 |
| GCCTCTTAAA | GATCATGTTT | GTTACAGTGC | TTAAAAATTA | ATATGTTCAT | CTGCAAAATG | 240 |
| GAATAAAAAA | TCTGTTAAAA | ATATATTTCA | CTAAATAGTT | AAGATGAGTC | ATATTTGTGG | 300 |
| GTTTTCATTT | TAAATTTTCT | TTCTCTAGGT | GAAGCTGTAC | TTCACAAAAA | CAGTAGAGGA | 360 |
| GCCGTCAAAT | CCAGAGGCTA | GCAGTTCAAC | TTCTGTAACA | CCAGATGTTA | GTGACAATGA | 420 |
| ACCTGATCAT | TATAGATATT | CTGACACCAC | TGACTCTGAT | CCAGAGAATG | AACCTTTTGA | 480 |
| TGAAGATCAG | CATACACAAA | TTACAAAAGT | CTGAATTTTT | TTTTATCAAG | AGGGATAAAA | 540 |
| CACCATGAAA | ATAAACTTGA | ATAAACTGAA | AAAAAAAAA | AAAAAA | | 587 |

Fig. 24

Ten μg of cell lysate run on a 12.5% reducing acrylamide gel.
Probed with 1:2,000 dilution of rabbit HB-10 serum

SEQUENCE LISTING (1) GENERAL INFORMATION:

(iii) NUMBER OF SEQUENCES: 94

(2) INFORMATION FOR SEQ ID NO: 1:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (vi) ORIGINAL SOURCE:
        (A) ORGANISM: Synthetic PCR primer (xi) SEQUENCE DESCRIPTION: SEQ ID NO: 1:

AAGCAAGTGA AGTCTTAGAA CCACC                                            25

(2) INFORMATION FOR SEQ ID NO: 2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (vi) ORIGINAL SOURCE:
        (A) ORGANISM: Synthetic PCR primer (xi) SEQUENCE DESCRIPTION: SEQ ID NO: 2:

CCACAAGTAA CAGAAAGCCT GTCTC                                            25

(2) INFORMATION FOR SEQ ID NO: 3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (vi) ORIGINAL SOURCE:
        (A) ORGANISM: Synthetic PCR primer (xi) SEQUENCE DESCRIPTION: SEQ ID NO: 3:

TGGCATCATT CTGGGGA                                                     17

```
(2) INFORMATION FOR SEQ ID NO: 4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (vi) ORIGINAL SOURCE:
        (A) ORGANISM: Synthetic PCR primer (xi) SEQUENCE DESCRIPTION: SEQ ID NO: 4:

GCTTTACGTT TCTTCACATG GT                                          22

(2) INFORMATION FOR SEQ ID NO: 5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (vi) ORIGINAL SOURCE:
        (A) ORGANISM: Synthetic PCR primer (xi) SEQUENCE DESCRIPTION: SEQ ID NO: 5:

ACACTTACAT AGTGCTTTCT GCG                                         23

(2) INFORMATION FOR SEQ ID NO: 6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (vi) ORIGINAL SOURCE:
        (A) ORGANISM: Synthetic PCR primer (xi) SEQUENCE DESCRIPTION: SEQ ID NO: 6:

CAGCCTCCCA AAGTTGC                                                17

(2) INFORMATION FOR SEQ ID NO: 7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (vi) ORIGINAL SOURCE:
        (A) ORGANISM: Synthetic PCR primer (xi) SEQUENCE DESCRIPTION: SEQ ID NO: 7:

GAGATTGAAG TGGATGTTGA AAG                                         23
```

```
(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (vi) ORIGINAL SOURCE:
        (A) ORGANISM: Synthetic PCR primer (xi) SEQUENCE DESCRIPTION: SEQ ID NO: 8:

AAATACAGGT CCTCTGACCC                                                   20

(2) INFORMATION FOR SEQ ID NO: 9:

(i) SEQUENCE CHARACTERISTICS:
        (A) LENGTH: 43 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Portion of exon 4 of gene correspondings to
            IMAGE 264611

(xi) SEQUENCE DESCRIPTION: SEQ ID NO: 9:

GAGGCCCTAG ATTTCTATGG GGAAGTAAGG ACCAGAGACA AAA                         43

(2) INFORMATION FOR SEQ ID NO: 10:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Mutant of exon4 of gene corresonding to IMAGE
            264611

(xi) SEQUENCE DESCRIPTION: SEQ ID NO: 10:

GAGGCCCTAG ATTTCTATGG GGAAGTTAAG GACCAGAGAC AAAA                        44

(2) INFORMATION FOR SEQ ID NO: 11:

(i) SEQUENCE CHARACTERISTICS:
        (A) LENGTH: 1773 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Partial cDNA of gene corresponding to IMAGE
            264611
```

(xi) SEQUENCE DESCRIPTION: SEQ ID NO: 11:

```
CGGCCGCGGC GGCTGCAGCT CCAGGGAGGG GGTCTGAGTC GCCTGTCACC ATTTCCAGGG      60
CTGGGAACGC CGGAGAGTTG GTCTCTCCCC TTCTACTGCC TCCAACACGG CGGCGGCGGC     120
GGCGGCACAT CCAGGGACCC GGGCCGGTTT TAAACCTCCC GTCCGCCGCC GCCGCACCCC     180
CCGTGGCCCG GGCTCCGGAG GCCGCCGGCG GAAGCAGCCG TTCGGAGGAT TATTCGTCTT     240
CTCCCCATTC CGCTGCCGCC GCTGCCAGGC CTCTGGCTGC TGAGGAGAAG CAGGCCCAGT     300
CGCTGCAACC ATCCAGCAGC CGCCGCAGCA GCCATTACCC GGCTGCGGTC CAGAGCCAAG     360
CGGCGGCAGA GCGAGGGGCA TCAGCTACCG CCAAGTCCAG AGCCATTTCC ATCCTGCAGA     420
AGAAGCCCCG CCACCAGCAG CTTCTGCCAT CTCTCTCCTC CTTTTTCTTC AGCCACAGGC     480
TCCCAGACAT GACAGCCATC ATCAAAGAGA TCGTTAGCAG AAACAAAAGG AGATATCAAG     540
AGGATGGATT CGACTTAGAC TTGACCTATA TTTATCCAAA CATTATTGCT ATGGGATTTC     600
CTGCAGAAAG ACTTGAAGGC GTATACAGGA ACAATATTGA TGATGTAGTA AGGTTTTTGG     660
ATTCAAAGCA TAAAAACCAT TACAAGATAT ACAATCTTTG TGCTGAAAGA CATTATGACA     720
CCGCCAAATT TAATTGCAGA GTTGCACAAT ATCCTTTTGA AGACCATAAC CCACCACAGC     780
TAGAACTTAT CAAACCCTTT TGTGAAGATC TTGACCAATG GCTAAGTGAA GATGACAATC     840
ATGTTGCAGC AATTCACTGT AAAGCTGGAA AGGGACGAAC TGGTGTAATG ATATGTGCAT     900
ATTTATTACA TCGGGGCAAA TTTTTAAAGG CACAAGAGGC CCTAGATTTC TATGGGGAAG     960
TAAGGACCAG AGACAAAAAG GGAGTAACTA TTCCCAGTCA GAGGCGCTAT GTGTATTATT    1020
ATAGCTACCT GTTAAAGAAT CATCTGGATT ATAGACCAGT GGCACTGTTG TTTCACAAGA    1080
TGATGTTTGA AACTATTCCA ATGTTCAGTG GCGGAACTTG CAATCCTCAG TTTGTGGTCT    1140
GCCAGCTAAA GGTGAAGATA TATTCCTCCA ATTCAGGACC CACACGACGG GAAGACAAGT    1200
TCATGTACTT TGAGTTCCCT CAGCCGTTAC CTGTGTGTGG TGATATCAAA GTAGAGTTCT    1260
TCCACAAACA GAACAAGATG CTAAAAAAGG ACAAAATGTT TCACTTTTGG GTAAATACAT    1320
TCTTCATACC AGGACCAGAG GAAACCTCAG AAAAAGTAGA AAATGGAAGT CTATGTGATC    1380
AAGAAATCGA TAGCATTTGC AGTATAGAGC GTGCAGATAA TGACAAGGAA TATCTAGTAC    1440
TTACTTTAAC ARAAAATGAT CTTGACAAAG CAAATAAAGA CAAAGCCAAC CGATACTTTT    1500
CTCCAAATTT TAAGGTGAAG CTGTACTTCA CAAAAACAGT AGAGGAGCCG TCAAATCCAG    1560
AGGCTAGCAG TTCAACTTCT GTAACACCAG ATGTTAGTGA CAATGAACCT GATCATTATA    1620
GATATTCTGA CACCACTGAC TCTGATCCAG AGAATGAACC TTTTGATGAA GATCAGCATA    1680
CACAAATTAC AAAAGTCTGA ATTTTTTTTT ATCAAGAGGG ATAAAACACC ATGAAAATAA    1740
ACTTGAATAA ACTGAAAAAA AAAAAAAAAA AAA                                 1773
```

(2) INFORMATION FOR SEQ ID NO: 12:

(i) SEQUENCE CHARACTERISTICS:
        (A) LENGTH: 565 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Translation of partial cDNA sequence (xi) SEQUENCE DESCRIPTION: SEQ ID NO: 12:

```
Ala Ala Ala Ala Ala Pro Gly Arg Gly Ser Glu Ser Pro Val Thr
 1               5                  10                  15

Ile Ser Arg Ala Gly Asn Ala Gly Glu Leu Val Ser Pro Leu Leu Leu
            20                  25                  30

Pro Pro Thr Arg Arg Arg Arg Arg His Ile Gln Gly Pro Gly Pro
            35                  40                  45

Val Leu Asn Leu Pro Ser Ala Ala Ala Pro Pro Val Ala Arg Ala
 50                      55                  60

Pro Glu Ala Ala Gly Gly Ser Ser Arg Ser Glu Asp Tyr Ser Ser Ser
 65                  70                  75                  80

Pro His Ser Ala Ala Ala Ala Arg Pro Leu Ala Ala Glu Glu Lys
            85                  90                  95

Gln Ala Gln Ser Leu Gln Pro Ser Ser Ser Arg Arg Ser Ser His Tyr
                100                 105                 110

Pro Ala Ala Val Gln Ser Gln Ala Ala Glu Arg Gly Ala Ser Ala
            115                 120                 125

Thr Ala Lys Ser Arg Ala Ile Ser Ile Leu Gln Lys Lys Pro Arg His
    130                 135                 140

Gln Gln Leu Leu Pro Ser Leu Ser Ser Phe Phe Phe Ser His Arg Leu
145                 150                 155                 160

Pro Asp Met Thr Ala Ile Ile Lys Glu Ile Val Ser Arg Asn Lys Arg
                165                 170                 175

Arg Tyr Gln Glu Asp Gly Phe Asp Leu Asp Leu Thr Tyr Ile Tyr Pro
                180                 185                 190

Asn Ile Ile Ala Met Gly Phe Pro Ala Glu Arg Leu Glu Gly Val Tyr
                195                 200                 205

Arg Asn Asn Ile Asp Asp Val Val Arg Phe Leu Asp Ser Lys His Lys
    210                 215                 220

Asn His Tyr Lys Ile Tyr Asn Leu Cys Ala Glu Arg His Tyr Asp Thr
225                 230                 235                 240

Ala Lys Phe Asn Cys Arg Val Ala Gln Tyr Pro Phe Glu Asp His Asn
                245                 250                 255

Pro Pro Gln Leu Glu Leu Ile Lys Pro Phe Cys Glu Asp Leu Asp Gln
                260                 265                 270

Trp Leu Ser Glu Asp Asp Asn His Val Ala Ala Ile His Cys Lys Ala
            275                 280                 285

Gly Lys Gly Arg Thr Gly Val Met Ile Cys Ala Tyr Leu Leu His Arg
    290                 295                 300

Gly Lys Phe Leu Lys Ala Gln Glu Ala Leu Asp Phe Tyr Gly Glu Val
305                 310                 315                 320

Arg Thr Arg Asp Lys Lys Gly Val Thr Ile Pro Ser Gln Arg Arg Tyr
                325                 330                 335

Val Tyr Tyr Tyr Ser Tyr Leu Leu Lys Asn His Leu Asp Tyr Arg Pro
                340                 345                 350

Val Ala Leu Leu Phe His Lys Met Met Phe Glu Thr Ile Pro Met Phe
            355                 360                 365

Ser Gly Gly Thr Cys Asn Pro Gln Phe Val Val Cys Gln Leu Lys Val
    370                 375                 380

Lys Ile Tyr Ser Ser Asn Ser Gly Pro Thr Arg Arg Glu Asp Lys Phe
385                 390                 395                 400

Met Tyr Phe Glu Phe Pro Gln Pro Leu Pro Val Cys Gly Asp Ile Lys
                405                 410                 415
```

```
Val Glu Phe Phe His Lys Gln Asn Lys Met Leu Lys Lys Asp Lys Met
            420                 425                 430
Phe His Phe Trp Val Asn Thr Phe Phe Ile Pro Gly Pro Glu Glu Thr
            435                 440                 445
Ser Glu Lys Val Glu Asn Gly Ser Leu Cys Asp Gln Glu Ile Asp Ser
            450                 455                 460
Ile Cys Ser Ile Glu Arg Ala Asp Asn Asp Lys Glu Tyr Leu Val Leu
465                 470                 475                 480
Thr Leu Thr Xaa Asn Asp Leu Asp Lys Ala Asn Lys Asp Lys Ala Asn
            485                 490                 495
Arg Tyr Phe Ser Pro Asn Phe Lys Val Lys Leu Tyr Phe Thr Lys Thr
            500                 505                 510
Val Glu Glu Pro Ser Asn Pro Glu Ala Ser Ser Ser Thr Ser Val Thr
            515                 520                 525
Pro Asp Val Ser Asp Asn Glu Pro Asp His Tyr Arg Tyr Ser Asp Thr
            530                 535                 540
Thr Asp Ser Asp Pro Glu Asn Glu Pro Phe Asp Glu Asp Gln His Thr
545                 550                 555                 560
Gln Ile Thr Lys Val (2) INFORMATION FOR SEQ ID NO: 13:

(i) SEQUENCE CHARACTERISTICS:
        (A) LENGTH: 871 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Part of gene corresponding to IMAGE 264611

(xi) SEQUENCE DESCRIPTION: SEQ ID NO: 13:

CGGCCGCGGC GGCTGCAGCT CCAGGGAGGG GGTCTGAGTC GCCTGTCACC ATTTCCAGGG      60

CTGGGAACGC CGGAGAGTTG GTCTCTCCCC TTCTACTGCC TCCAACACGG CGGCGGCGGC     120

GGCGGCACAT CCAGGGACCC GGGCCGGTTT TAAACCTCCC GTCCGCCGCC GCCGCACCCC     180

CCGTGGCCCG GCTCCGGAG GCCGCCGGCG GAAGCAGCCG TTCGGAGGAT TATTCGTCTT     240

CTCCCCATTC CGCTGCCGCC GCTGCCAGGC CTCTGGCTGC TGAGGAGAAG CAGGCCCAGT     300

CGCTGCAACC ATCCAGCAGC CGCCGCAGCA GCCATTACCC GGCTGCGGTC CAGAGCCAAG     360

CGGCGGCAGA GCGAGGGGCA TCAGCTACCG CCAAGTCCAG AGCCATTTCC ATCCTGCAGA     420

AGAAGCCCCG CCACCAGCAG CTTCTGCCAT CTCTCTCCTC CTTTTTCTTC AGCCACAGGC     480

TCCCAGACAT GACAGCCATC ATCAAAGAGA TCGTTAGCAG AAACAAAAGG AGATATCAAG     540

AGGATGGATT CGACTTAGAC TTGACCTGTA TCCATTTCTG CGGCTGCTCC TCTTTACCTT     600

TCTGTCACTC TCTTAGAACG TGGGAGTAGA CGGATGCGAA AATGTCCGTA GTTTGGGTGA     660

CTATAACATT TAACCCTGGT CAGGTTGCTA GGTCATATAT TTTGTGTTTC CTTTCTGTGT     720

ATTCAACCTA GGGTGTGTTT GGCTAGACGG AACTCTTGCC TGGTTGCAAG TGTCAAGCCA     780

CCGATTGCTT TCTTAGGCTA TCTATATGGT CTCTTCCTGA GGCTATTGT CCGTTAATAC     840

AGAATACAGT AAGGAGAGGA CAGCGATCCT A                                   871
```

(2) INFORMATION FOR SEQ ID NO: 14:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Part of gene corresponding to IMAGE 264611

(xi) SEQUENCE DESCRIPTION: SEQ ID NO: 14:

```
TCGNATCCNT ACCCGTTCGT ACGAGAATCG CTGTCCCTCT CCCTTCTAAT GTTTTAAAAA      60
GTATTCTTTT AGTTTGATTG CTGCATATTT CAGATATTTC TTTCCTTAAC TAAAGTAACT     120
CAGATATTTA TCCAAACATT ATTGCTATGG GATTTCCTGC AGAAAGACTT GAAGGCGTAT     180
ACAGGAACAA TATTGATGAT GTAGTAAGGT AAGAATGCTT TGATTTTCTA TTTCAAATAT     240
TGATGTTTAT ATTCATGTTG TGTTTTCATT TAGAAAAGAT TTCTAAGCCA CAGAAAAGA      300
TACTTTGTGA TGTAAACTAT TATTGTAGTG CTCTATAATC ATTTTTTGGC TTACCGTACC     360
TAATGGACTT CAGGGGGATA CAGTTCATTT GATAAGAACT GACCTTATAC ATTACATAAT     420
CAGGTACTTA TGTGATAAGG ANAGGACACA TCTCGTACAA NGAGG                    465
```

(2) INFORMATION FOR SEQ ID NO: 15:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Part of gene corresponding to IMAGE 264611

(xi) SEQUENCE DESCRIPTION: SEQ ID NO: 15:

```
TAAAACACAG CATAATATGT GTCACATTAT AAAGATTCAG GCAATGTTTG TTAGTATTAG      60
TACTTTTTTT TCTTCCTAAG TGCAAAAGAT AACTTTATAT CACTTTTAAA CTTTTCTTTT     120
AGTTGTGCTG AAAGACATTA TGACACCGCC AAATTTAATT GCAGAGGTAG GTATGAATGT     180
ACTGTACTAT GTTGTATAAC TTAAACCCGA TAGACTGTAT CTTACTGTCA TAACAATAAT     240
GAGTCATCCA GATTATCGAG TGAGATACAT ATTTATCTTA AGAATTATCT TTAAAAATTT     300
CAAAAATTTT AATTTGACTG TTGTGTTTTA GGAAAAAGTA TTGCATAAAG CTATTAATAT     360
TGTCAGGAAG ACTAAAGTGC AGCATA                                        386
```

(2) INFORMATION FOR SEQ ID NO: 16:

(i) SEQUENCE CHARACTERISTICS:
        (A) LENGTH: 724 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
    (A) ORGANISM: Part of gene corresponding to IMAGE 264611

(xi) SEQUENCE DESCRIPTION: SEQ ID NO: 16:

```
TTTTCTACCT CTAATNGCTG ACNTATGCTA CCAGTCCGTA TAGCGTAAAT TCCCAGAATA      60
TATCCTCCTG AATAAAATGG GGGAAAATAA TACCTGGCTT CCTTAATGAT TATATTTAAN    120
ACTTATCAAN ANACTATTTT CTATTTAACA ATTAGAAAGT TAAGCAATAC ATTATTTTC     180
TCTGGAATCC AGTGTTTCTT TTAAATACCT GTTAAGTTTG TATGCAACAT TTCTAAAGTT    240
ACCTACTTGT TAATTAAAAA TTCAANAGTT TTTTTTNCTT ATTCTGAGGT TATCTTTTA     300
CCACAGTTGC ACAATATCCT TTTGAAGACC ATAACCCACC ACAGCTAGAA CTTATCAAAC    360
CCTTTTGTGA AGATCTTGAC CAATGGCTAA GTGAAGATGA CAATCATGTT GCAGCAATTC    420
ACTGTAAAGC TGGAAAGGGA CGAACTGGTG TAATGATATG TGCATATTTA TTACATCGGG    480
GCAAATTTTT AAAGGCACAA GAGGCCCTAG ATTTCTATGG GGAAGTAAGG ACCAGAGACA    540
AAAAAGGTAA GTTATTTTTT GATGTTTTTC CTTTCCTCTT CCTGGATCTG AGAATTTATT    600
GGAAAACAGA TTTTGGGTTT CTTTTTTTCT TCAGTTTTAT TGAGGTGTAA TTGCACAAGT    660
AAAAATTATA TATAAATACA ATGTATAATA TGATGTTTGG ATGTATGTGT ATATACATTG    720
TGAA                                                                 724
```

(2) INFORMATION FOR SEQ ID NO: 17:

(i) SEQUENCE CHARACTERISTICS:
        (A) LENGTH: 542 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Part of gene corresponding to IMAGE 264611

(xi) SEQUENCE DESCRIPTION: SEQ ID NO: 17:

```
AAGGTCAAAT GTCTAATGTA TATATGTTCT TAAATGGCTA CGACCCAGTT ACCATAGCAA      60
TTTAGTGAAA TAACTATAAT GGAACATTTT TTTTCAATTT GGCTTCTCTT TTTTTTCTGT    120
CCACCAGGGA GTAACTATTC CCAGTCAGAG GCGCTATGTG TATTATTATA GCTACCTGTT    180
AAAGAATCAT CTGGATTATA GACCAGTGGC ACTGTTGTTT CACAAGATGA TGTTTGAAAC    240
TATTCCAATG TTCAGTGGCG GAACTTGCAG TAAGTGCTTG AATCTCATCC TTCCATGTTA    300
TTGGGAACAG TTTTCTTAAC CATATCTAGA AGTTTACATA AAAATTTAGA AAGAAATTTA    360
CCACATTTGA AATTTATGCA GGAGACTATA TTTCTGAAGC ATTTGAACAA ATTAATTAGC    420
TTTGTTGTTC AACTCATTGG GCTAAAGAAG CCAAAAGCAA TGGGTTTTAA TGTAGTCGAA    480
GCCAAATTAT ATTTATGAAA GAAATATTCT GTGTTATAAC CACCAAATAC AGCCCAATTC    540
TG                                                                   542
```

(2) INFORMATION FOR SEQ ID NO: 18:

(i) SEQUENCE CHARACTERISTICS:
        (A) LENGTH: 638 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
    (A) ORGANISM: Part of gene corresponding to IMAGE 264611

(xi) SEQUENCE DESCRIPTION: SEQ ID NO: 18:

| | | | | | |
|---|---|---|---|---|---|
| ACTCTGCCAC | TAGAAGTCTA | ATTTTGGGAC | TTACTATTCA | TGAAATAGGA | ATTGACTTTN | 60 |
| ATATAAGTAA | TAGGACCTTA | TTTTGAAGGT | TCAAACTGGA | GAAAATCTTA | CATTGTTTAT | 120 |
| ATTTTTATTT | CATTTANTTC | AGTTGATTTG | CTTGAGATCA | AGATTGCAGA | TACAGAATCC | 180 |
| ATATTTCGTG | TATATTGCTG | ATATTAATCA | TTAAAATCGT | TTTTGACAGT | TTGACAGTTA | 240 |
| AAGGCATTTC | CCTGTGAAAT | AATACTGGTA | TGTATTTAAC | CATGCAGATC | CTCAGTTTGT | 300 |
| GGTCTGCCAG | CTAAAGGTGA | AGATATATTC | CTCCAATTCA | GGACCCACAC | GACGGGAAGA | 360 |
| CAAGTTCATG | TACTTTGAGT | TCCCTCAGCC | GTTACCTGTG | TGTGGTGATA | TCAAAGTAGA | 420 |
| GTTCTTCCAC | AAACAGAACA | AGATGCTAAA | AAGGGTTTGT | ACTTTACTTT | CATTGGGAGA | 480 |
| AATATCCAAA | ATAAGGACAG | ATTANAAGCT | NTATTNTATT | TTATGACATG | TAAGGAACTA | 540 |
| TAATTTGTTT | TCTATTAGAT | CTGCCAGGTG | TTTTGCTTAC | TCTGGCATTG | GTGAGACATT | 600 |
| ATANGGGTAA | ATAATCCTGT | TTGAAGGAAN | AGGCCTAT | | | 638 |

(2) INFORMATION FOR SEQ ID NO: 19:

(i) SEQUENCE CHARACTERISTICS:
        (A) LENGTH: 590 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Part of gene corresponding to IMAGE 264611

(xi) SEQUENCE DESCRIPTION: SEQ ID NO: 19:

| | | | | | |
|---|---|---|---|---|---|
| TTTATCTTAG | ATCTTGTGAG | ATTGTATTTT | TGGTTTAAAA | TTTGAGAATT | TGAGTGAAGA | 60 |
| AAAATCATGT | GAATGAAAAT | GCAACAGATA | ACTCAGATTG | CCTTATAATA | GTCTTTGTGT | 120 |
| TTACCTTTAT | TCAGAATATC | AAATGATAGT | TTATTTTGTT | GACTTTTTGC | AAATGTTTAA | 180 |
| CATAGGTGAC | AGATTTNCTT | TTTTAAAAAA | ATAAAACATC | ATTAATTAAA | TATGTCATTT | 240 |
| CATTTCTTTT | TCTTTTCTTT | TTTTTTTTTT | TAGGACAAAA | TGTTTCACTT | TTGGGTAAAT | 300 |
| ACATTCTTCA | TACCAGGACC | AGAGGAAACC | TCAGAAAAAG | TAGAAAATGG | AAGTCTATGT | 360 |
| GATCAAGAAA | TCGATAGCAT | TTGCAGTATA | GAGCGTGCAG | ATAATGACAA | GGAATATCTA | 420 |
| GTACTTACTT | TAACARAAAA | TGATCTTGAC | AAAGCAAATA | AAGACAAAGC | CAACCGATAC | 480 |
| TTTTCTCCAA | ATTTTAAGGT | CAGTTAAATT | AAACATTTTG | TGGGGGNTGG | TGACTTGTAT | 540 |
| GTATGTGATG | TGTGTTTAAT | TCTAGGAGTA | CAGAAGGAGA | GGACAGCGAT | | 590 |

(2) INFORMATION FOR SEQ ID NO: 20:

(i) SEQUENCE CHARACTERISTICS:
        (A) LENGTH: 586 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
            (A) ORGANISM: Part of gene corresponding to IMAGE 264611

(xi) SEQUENCE DESCRIPTION: SEQ ID NO: 20:

| | | | | | |
|---|---|---|---|---|---|
| GGAGGCAGAG | GTTGCAGTGA | GCCAAGATCA | TGCCACTGCA | CTCCAGCTTG | GCAACAGAGC | 60 |
| AAGACTCTTG | TCTCCAGAAA | TAAAAATAAA | TAAATTGTAT | TAACATCCTG | ATAGTTTATC | 120 |
| TGTTTAGTAC | CTAGCAAGAA | AGAAAATGTT | GAACATCTTA | AGAAGAGGGT | CATTTAAAAG | 180 |
| GCCTCTTAAA | GATCATGTTT | GTTACAGTGC | TTAAAAATTA | ATATGTTCAT | CTGCAAAATG | 240 |
| GAATAAAAAA | TCTGTTAAAA | ATATATTTCA | CTAAATAGTT | AAGATGAGTC | ATATTTGTGG | 300 |
| GTTTTCATTT | TAAATTTTCT | TTCTCTAGTG | AAGCTGTACT | TCACAAAAAC | AGTAGAGGAG | 360 |
| CCGTCAAATC | CAGAGGCTAG | CAGTTCAACT | TCTGTAACAC | CAGATGTTAG | TGACAATGAA | 420 |
| CCTGATCATT | ATAGATATTC | TGACACCACT | GACTCTGATC | CAGAGAATGA | ACCTTTTGAT | 480 |
| GAAGATCAGC | ATACACAAAT | TACAAAAGTC | TGAATTTTTT | TTTATCAAGA | GGGATAAAAC | 540 |
| ACCATGAAAA | TAAACTTGAA | TAAACTGAAA | AAAAAAAAAA | AAAAAA | | 586 |

(2) INFORMATION FOR SEQ ID NO: 21:

(i) SEQUENCE CHARACTERISTICS:
        (A) LENGTH: 234 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 21:

| | | | | | |
|---|---|---|---|---|---|
| TTTAATACGA | CTCACTATAG | GGAATTTGGC | CCTCGAGGCC | AAGAATTCCC | GACTACGTAG | 60 |
| TCGGGGATCC | GTCTTAATTA | AGCGGCCGCA | AGCTTATTCC | CTTTAGTGAG | GGTTAATTTT | 120 |
| AGCTTGGCAC | TGGCCGTCGT | TTTACAACGT | CGTGACTGGG | AAAACCCTGG | CGTTACCCAA | 180 |
| CTTAATCGCC | TTGCAGCACA | TCCCCCTTTC | GCCAGCTGGC | GTAATAGCGA | AGAG | 234 |

(2) INFORMATION FOR SEQ ID NO: 22:

(i) SEQUENCE CHARACTERISTICS:
        (A) LENGTH: 510 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human (xi) SEQUENCE DESCRIPTION: SEQ ID NO: 22:

| | | | | | |
|---|---|---|---|---|---|
| ATGTAGTAAG | GTTTTTGGAT | TCAAAGCATA | AAAACCATTA | CAAGATATAC | AATCTTTGTG | 60 |
| CTGAAAGACA | TTATGACACC | GCCAAATTTA | ATTGCAGAGT | TGCACAATAT | CCTTTTGAAG | 120 |
| ACCATAACCC | ACCACAGCTA | GAACTTATCA | AACCCTTTTG | TGAAGATCTT | GACCAATGGC | 180 |
| TAAGTGAAGA | TGACAATCAT | GTTGCAGCAA | TTCACTGTAA | AGCTGGAAAG | GGACGAACTG | 240 |
| GTGTAATGAT | ATGTGCATAT | TTATTACATC | GGGGCAAATT | TTTAAAGGCA | CAAGAGGGCC | 300 |

```
CTAGATTTCT ATGGGGAAGT AAGGACCAGA GACAAAAAGG GAGTAACTAT TTCCCAGTCA      360

GAAGGCGCTA TGTGTATTAT TATTAGCTAC CTGTTAAAGA ATCATCTGGA TTATAGACCA      420

GTGGCACTGT TGTTTCCCAA GATGATGNTT TGAAACTATT NCCAATGTTC AGTGGCNGGA      480

CCTTGCAATC CNCAGTTTGT GGGTCCTGCN                                       510
```

(2) INFORMATION FOR SEQ ID NO: 23:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 23:

```
CAGTTTATTC AAGTTTATTT TCATGGTGTT TTATCCCTCT TGATAAAAAA AAATTCAGAC       60

TTTTGTAATT TGTGTATGCT GATCTTCATC AAAAGGTTCA TTCTCTGGAT CAGAGTCAGT      120

GGTGTCAGAA TATCTATAAT GATCAGGTTC ATTGTCACTA ACATCTGGTG TTACAGAAGT      180

TGAACTGCTA GCCTCTGGAT TTGACGGCTC CTCTACTGTT TTTGTGAAGT ACAGCTTCAC      240

CTTAAAATTT GGAGAAAAGT ATCGGTTGGC TTTGTCTTTA TTTGCTTTGT CAAGATCATT      300

TTTTGTTAAA GTAAGTACTA GATATTCCTT GTCATTATCT GCACGCTCTA TACTGCAAAT      360

GCTATCGATT TCTTGATCAC ATAGACTTTC CATTTTCNAC TTTTTCNGAG GTTT            414
```

(2) INFORMATION FOR SEQ ID NO: 24:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 24:

```
GCGGCCGCGG NGGNTGCAGC TCCANGNAGG GGGTCTGAGT CGCCTGTCAC CATTTNCAGG       60

GCTGGGAACG CCGGAGAGTT GGTCTCTCCC CTTCTACTGC CTCCAACACG GCGGCNGCGG      120

CGGCGGCACA TCCAGGGACC CGGGCCGGTT TTAAACCTCC CGTCCGCCGC CGCCGCACCC      180

CCCAGTGGCC CGGGCTCCGG AGNCCGCCTG GCGGAGGCAA GCCGTTCGGA GGGATTATTC      240

G                                                                      241
```

(2) INFORMATION FOR SEQ ID NO: 25:

(i) SEQUENCE CHARACTERISTICS:
        (A) LENGTH: 84 base pairs
        (B) TYPE: nucleic acid
        (C) STRANDEDNESS: single (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 25:

GATCAGCATA CACAAATNAC AAAAGTCTGA ATTTTTTTTT ATCAAGAGGG ATAAAACACC     60

ATGAAAATAA ACTTGAATAA ACTG                                          84

(2) INFORMATION FOR SEQ ID NO: 26:

(i) SEQUENCE CHARACTERISTICS:
        (A) LENGTH: 427 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 26:

GGAAGTNGGT NATGGTCTTC AAAAGGATAT TGTGCAACTC TGCAATTAAA TTTGGCGGTG     60

TCATAATGTC TTTCAGCACA AAGATTGTAT ATCTTGTAAT GGTTTTTATG CTTTGAATCC    120

AAAAACCTTA CTACATCATC AATATTGTTC CTGTATACGC CTTCAAGTCT TTCTGCAGGA    180

AATCCCATAG CAATAATGTT TGGATAAATA TAGGTCAAGT CTAAGTCGAA TCCATCCTCT    240

TGATATCTCC TTTTGTTTCT GGCTAACGAT CTCTTTGGAT GGATGGCTGT CATGTCTGGG    300

GAGCCTGTGN TGGNAAGGAA AAAGGGAGGG AGAGAGATGG GCAGAAGCTG GCTCGGTGGG    360

CGGGGGCTTT CTTCTGGCAG GGATGGGAAA TGGGCTCTGG GGACTGGGCG GTACTGGATG    420

GCCCCTC                                                            427

(2) INFORMATION FOR SEQ ID NO: 27:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 27:

TCCAGGGCTG GGAACGCCGG AGAGTTGGTC TCTCCCCTTC TACTGCCTCN AACACGGCGG     60

CGGCGGCGGC GGCACATCCA GGGACCCGGG CCGGTTTTAA ACCTCCCGTC CGCCGCC      117

(2) INFORMATION FOR SEQ ID NO: 28:

(i) SEQUENCE CHARACTERISTICS:
        (A) LENGTH: 322 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 28:

GGTCTGAGTC GCCTGTCACC ATTTCCAGGG CTGGGAACGC NGGAGAGTTG GTCTCTCCCC    60

TTCTACTGCC TCCAACACGG CGGCGGCGGC GGCGGCACAT CCAGGGACCC GGGCCGGTTT   120

TAAACCTCCC GTCCGCCGCC GCCGCACCCC CCGTGGCCCG GGCTCCGGAG GCCGCCGGCG   180

GAGNAAGCCG TTTCGGAGGA TTATTCGTCT TCTCCCCATT CCGCTGCCGC CCGCTGCCAG   240

GCTCTTGGTG CTTGAAGAAG AAGCAGGCCA GTTGNCTGAA ACCATTCNAG AAGCCGCNGA   300

AGCAGCCATT ACNCGGCTGC GG                                           322

(2) INFORMATION FOR SEQ ID NO: 29:

(i) SEQUENCE CHARACTERISTICS:
        (A) LENGTH: 427 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 29:

TAAGTACTAG ATATTCCTTG TCATTATCTG CACGCTCTAT ACTGCAAATG CTATCGATTT    60

CTTGATCACA TAGACTTCCA TTTTCTACTT TTTCTGAGGT TTCCTCTGGT CCTGGTATGA   120

AGAATGTATT TACCCAAAAG TGAAACATTT TGTCCTTTTT TAGCATCTTG TTCTGTTTGT   180

GGAAGAACTC TACTTTGATA TCACCACACA CAGGTAACGG CTGAGGGAAC TCAAAGTACA   240

TGAACTTGTC TTCCCGTCGT GTGGGTCCTG AATTGGAGGA ATATATCTTC ACCTTTAGCT   300

GGCAGACCAC AAACTGNAGG ATTGCAAGTT CCGCCACTGA ACATTGGAAT AGTTTCAAAC   360

ATCATCTTGT GAAACAACAG TGCCACTGGT CTATAAGCCA GATGATTCTT TAACAGGGTA   420

GCTATAA                                                            427

(2) INFORMATION FOR SEQ ID NO: 30:

(i) SEQUENCE CHARACTERISTICS:
        (A) LENGTH: 437 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (A) ORGANISM: HUMAN (xi) SEQUENCE DESCRIPTION: SEQ ID NO: 30:

CAGTTTATTC AAGTTTATTT TCATGGTGTT TTATCCCTCT TGATAAAAAA AAATTCAGAC      60

TTTTGTAATT TGTGTATGCT GATCTTCATC AAAAGGTTCA TTCTCTGGAT CAGAGTCAGT    120

GGTGTCAGAA TATCTATAAT GATCAGGTTC ATTGTCACTA ACATCTGGTG TTACAGAAGT    180

TGAACTGCTA GCCTCTGGAT TTGACGGCTC CTCTACTGTT TTNGTGAAGT ACAGCTTCAC    240

CTTAAAATTT GGAGAAAAGT ATCGGTTGGC TTTGTCTTTA TTTGCNTTGT CAAGATCATT    300

TTCTGTTAAA GTAAGTACTA TGATATTCCT TGTCATTATC TGCACGCTCT ATACTGCAAA    360

TGCTATCGAT TTCTTGATCA CATAGACTTC CATTTTCTAC TTTTTCNGAG GTTTCCCCCN    420

GGTCCNGGGT AATGAAN                                                   437

(2) INFORMATION FOR SEQ ID NO: 31:

(i) SEQUENCE CHARACTERISTICS:
            (A) LENGTH: 372 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (A) ORGANISM: HUMAN (xi) SEQUENCE DESCRIPTION: SEQ ID NO: 31:

TTTTTGGATT CAAAGCATAA AAACCATTAC AAGATATTTT ATCTTCTNNG CTGAAAGACA     60

TTATGACACC GCCAAATTTA ATTGCAGAGT TGCACAATAT CCTTTTGAAG ACCATAACCC    120

ACCACAGCTA GAACTTATCA AACCCTTTTG TGAAGATCTT GACCAATGGC TAAGTGAAGA    180

TGACAATCAT GTTGCAGCAA TTCACTGTAA AGCTGGAAAG GGACGAACTG GTGTAATGAT    240

ATGTGCATAT TTATTACATC GGGGCAAATT TTTAAAGGCA CAAGAGGCCC NAAGATTTCT    300

ATGGGGAAGT AAGGGCCCGA GACNAAAAGG GNGTAACTAT TCCCAGTCAG AGGGCGCTAT    360

GTGTNTTATT AT                                                        372

(2) INFORMATION FOR SEQ ID NO: 32:

(i) SEQUENCE CHARACTERISTICS:
            (A) LENGTH: 474 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (A) ORGANISM: HUMAN (xi) SEQUENCE DESCRIPTION: SEQ ID NO: 32:

AGCCGCTTTA ATTAAAGATC TTTTTTTTTT TTTTTTTTTC AGTTTATTCA AGTTTATTTT     60

```
CATGGTGTTT TATCCCTCTT GATAAAAAAA AATTCAGACT TTTGTAATTT GTGTATGCTG    120

ATCTTCATCA AAAGGGTTCA TTCTCTGGAT CAGAGTCAGT GGGTGTCAGA ATATCTATAA    180

TGATCAGGTT CATTGTCACT AACATCTGGN GTTACAGAAG TTGAACTGCT AGCCTCTGGG    240

ATTTGACGGC TCCNCTACTG TTTTTGTGAA GTACAGCTTC ACCTTAAAAT TTGGNGAAAA    300

GTATCGGTTG GCTTTGTCTT TATTTGCTTT GTCAAGATCA TTTTTTGTTA AAGTAAGGAC    360

TAGGATATTC CCTGTCATTA TCTGCACGCT CTATACTGCA AATGCTATCG ATTTCTTGAT    420

CACATAGGGC TTCCNTTTTC TACTTTTTCT GAGGGTTNCC CTGGTCCGGG NTTG          474
```

(2) INFORMATION FOR SEQ ID NO: 33:

(i) SEQUENCE CHARACTERISTICS:
        (A) LENGTH: 429 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 33:

```
TGTTCTGTAA GTTACTTTTA CCGTTAAACT TCTTAATGTT GCTTATTGTT TGTCTTACAT     60

TTTTAGGTTG GATTTTTCTT AAGTCACATG TCTAATAAAA AAAACCCTTA AATACCTCAT    120

TTATTCGTCT TCGTTAGTGA ATGCATTGTT GTACATATTA GATTTTTCTC TTTAGATAAC    180

TCAGCTTCCC CTATTAAGTG CCACATGTAT TACAAAATTT TATTTATGTT TTATTGTTTA    240

ATAAACTCTT GAGAACTAGA TACATTTTAA TCATTTGTAA TACTTACATT TTCTAAAACA    300

CTTCATTTTT CCCGGGGTTC TTCAACAAAG GGGATGGCAT GTAGGTACAA GGGATAGCTT    360

TACCNGTGTT AGGAAGGTTG TTTTCACACC TTTACATCAA CTGCATAGTC CCGTTTTTGT    420

TGGGGCCCA                                                            429
```

(2) INFORMATION FOR SEQ ID NO: 34:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 34:

```
GGGCTCCGGA GCCGCCGGCG GAGGCAGCCG TTCGGAGGAT TATTCGTCTT CTCCCCATTC     60

CGCTGCCGCC GCTGCCAGGC CTCTGCTGCT GAGGAGAAGC AGGCCCAGTC GCTGCAACCA    120

TCCAGCAGCC GCCGCAGCAG CCATTACCCG GCTGCGGTCC AGAGCCAAGA CGCAGAGAGG    180

GCATCAGCTA CCGCCAAGTC AGAGCATTTC CATCTCAGAA GAAG                     224
```

(2) INFORMATION FOR SEQ ID NO: 35:

(i) SEQUENCE CHARACTERISTICS:
        (A) LENGTH: 266 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 35:

```
TGGAGGGAAG ACAAGTTCAT GTACTTTGAG TTCCCTCAGC CGTTACCTGT GTGTGGTGAT      60
ATCAAAGTAG AGTTCTTCCA CAAACAGAAC AAGATGCTAA AAAAGGACAA AATGTTTCAC     120
TTTTGGGTAA ATACATTCTT CATACCAGGA CCAGAGGAAA CCTCAGAAAA AGTAGAAAAT     180
GGAAGTCTAT GTGATCAAGN AATCGATAGC ATTTGCAGTA TAGAGCGTGC AGATAATGAC     240
AAGGAATATC TAGTACTTAC TTTAAC                                         266
```

(2) INFORMATION FOR SEQ ID NO: 36:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 36:

```
TCAAATCCAG AGGCTAGCAG TTCAACTTCT GTAACACCAG ATGTTAGTGA CAATGAACCT      60
GATCATTATA GATATTCTGA CACCACTGAC TCTGATCCAG AGAATGAACC TTTTGATGAA     120
GATCAGCATA CACAAATTAC AAAAGTCTGA ATTTTTTTTT ATCAAGAGGG ATAAAACACC     180
ATGAAAATAA ACTTGAATAA ACTGAAAATG GGACCTTTTT TTTTTTTAAT GGGCAATAGG     240
GACATTGTGT CAGGATTACC AGTTATAGGG GACAATTCTC TTTTCCCTGG ACCCAATCTT     300
GTTTTTTACC CTATACATCC ACCGGGGGTT TTTTGACACT TGTTTGTCCC AGTTGGAAAA     360
AGGGTTGTNT TGGCCGTNGT CCAGGATTAT ACCCTT                              396
```

(2) INFORMATION FOR SEQ ID NO: 37:

(i) SEQUENCE CHARACTERISTICS:
        (A) LENGTH: 451 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:

(A) ORGANISM: HUMAN (xi) SEQUENCE DESCRIPTION: SEQ ID NO: 37:

CAACTTCTGT AACACCAGAT GTTAGTGACA ATGAACCTGA TCATTATAGA TATTCTGACA        60

CCACTGACTC TGATCCAGAG AATGAACCTT TTGATGAAGA TCAGCATACA CAAATTACAA       120

AAGTCTGAAT TTTTTTTTAT CAAGAGGGAT AAAACACCAT GAAATAAAC TTGAATAAAC        180

TGAAAATGGA CCTTTTTTTT TTTAATGGCA ATAGGACATT GTGTCAGATT ACCAGTTATA       240

GGAACAATTC TCTTTTCCTG ACCAATCTTG NTTTACCCNA TACATTCCCA GGGGTTTGGA       300

CACTTGGTGG TCCAGNTTGA AAAAAGGTTG TGTAGCTGTG NCATGGTATA TACCTTTTTG       360

TGGCCAAAAG GGACATTTAA AATTCAATTA GGATTAATAA AGATGGGCAC TTTCCCGTTT       420

AATTCCAGTT TTATAAAAAG TGGGGACAGA C                                     451

(2) INFORMATION FOR SEQ ID NO: 38:

(i) SEQUENCE CHARACTERISTICS:
        (A) LENGTH: 902 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 38:

GNGNNNTTNC TACTCANGAT CATTTGGNGG TTAAAGTAAG TACTAGATAN TCCTTGTCAT        60

TATCTGCACG CTCTATACTG CAAATGCTAT CGATTTCTTG ATCACATAGA CTTCCATTTT       120

CTACTTTTNC TGAGGTTNCC TCTGGTCCTG GTATGAAGAA TGTATTTACC CAAAAGTGAA       180

ACATTGGGTC CTTTTTTAGC ATCTGGTNCT GTGNGTGGAA GAACTCTACT TGGATATCAC       240

CACACACAGG TAACGGCTGA GGGAACTCAA AGTACATGAA CTTGTCTTCC CGNCGNGTGG       300

GTCCTGAATT GGAGGAATAT NTCTTCACCT NNAGCTGGCA GACCACAAAC TGAGGATTGC       360

AAGTNCCGCC ACTGAACATG GGAATAGGNT CAAACATCAN CTTGGGAAAC AACAGGGNCA       420

CTGGTCTTTT ANCCAGNTGA TCNNNACAGG GGGTATNATA NACANANGGG CCCNNNNNGG       480

AATGGGNCNC CNNGGGGTTN NNCCCNNNNC CCANNNNNNC ANNGGGNTNC CGGNGGGNNN       540

NNNNNNNNNN NNNNNNNNNN NNNNNNNNNN NNNNNNNNNN NNNNNNNNNN NNNNNNNNNN       600

NNNNNNNNNN NNNNNNNNNN NNNNNNNNNN NNNNNNNNNN NNNNNNNNNN NNNNNNNNNN       660

NNNNNNNNNN NNNNNNNNNN NNNNNNNNNN NNNNNNNNNN NNNNNNNNNN NNNNNNNNNN       720

NNNNNNNNNN NNNNNNNNNN NNNNNNNNNN NNNNNNNNNN NNNNNNNNNN NNNNNNNNNN       780

NNNNNNNNNN NNNNNNNNNN NNNNNNNNNN NNNNNNNNNN NNNNNNNNNN NNNNNNNNNN       840

NNNNNNNNNN NNNNNNNNNN NNNNNNNNNN NNNNNNNNNN NNNNNNNNNN NNNNNNNNNN       900

CC                                                                     902

(2) INFORMATION FOR SEQ ID NO: 39:

(i) SEQUENCE CHARACTERISTICS:
        (A) LENGTH: 601 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (A) ORGANISM: HUMAN (xi) SEQUENCE DESCRIPTION: SEQ ID NO: 39:

| | | | | | |
|---|---|---|---|---|---|
| GCAAGAGGGA | TAAAACACCA | TGAAAATAAA | CTTGAATAAA | CTGAAAATGG | ACCCTTTTTT | 60 |
| TTTTAATGGC | AATAGGACAT | TGTGTCAGAT | TACCAGTTAT | AGGAACAATT | CTCTTTTCCT | 120 |
| GACCAATCTT | GTTTTACCCT | ATACATCCAC | AGGGTTTTGA | CACTTGTTGT | CCAGTTGAAA | 180 |
| AAAGGTTGTG | TAGCTGTGTC | ATGTATATAC | CTTTTTGTGT | CAAAAGGACA | TTTAAAATTC | 240 |
| AATTAGGATT | AATAAAGATG | GCACTTTCCC | GTTTTATTCC | AGTTTTATAA | AAAGTGGAGA | 300 |
| CAGACTGATG | TGTATACGTA | GGAATTTTTT | CCTTTTGTGT | TCTGTCACCA | ACTGAAGTGG | 360 |
| CTAAAGAGCT | TTGTGATATA | CTGGTTCACA | TCCTACCCCT | TTGCACTTGT | GGCAACAGAT | 420 |
| AAGTTTGCAG | TTGGGCTAAG | AGAGGTTTCC | GAAGGGTTTT | GCTACATTCT | AATGCATGTA | 480 |
| TTCGGGGTTA | GGGGAATGGA | GGGGAATGCT | CAGAAAGGAA | ATAATTTTAA | TGCTGGACTC | 540 |
| TGGACCATAT | ACCATCTCCA | GCTANTTACA | CACACCTTTC | CTTAGCATGC | CACAGTTATT | 600 |
| A | | | | | | 601 |

(2) INFORMATION FOR SEQ ID NO: 40:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (A) ORGANISM: HUMAN (xi) SEQUENCE DESCRIPTION: SEQ ID NO: 40:

| | | | | | |
|---|---|---|---|---|---|
| ATACCAGGAC | CAGAGGAAAC | CTCAGAAAAA | GTAGAAAATG | GAAGTCTATG | TGATCAAGAA | 60 |
| ATCGATAGCA | TTTGCAGTAT | AGAGCGTGCA | GATAATGACA | AGGAATATCT | AGTACTTACT | 120 |
| TTAACAAAAA | ATGATCTTGA | CAAAGCAAAT | AAAGACAAAG | CCAACCGATA | CTTTTCTCCA | 180 |
| AATTTTAAGG | TGAAGCTGTA | CTTCACAAAA | ACAGTAGAGG | AGCCGTCAAA | TCCAGAGGCT | 240 |
| AGCAGTTCAA | CTTCTGTAAC | ACCAGATGTT | ACGTGACAAT | GAACCTGATC | ATTATAGATA | 300 |
| TTCTGACACC | ACTGACTCTG | ATCCAGAGAA | TGAACCTTTT | GATGAAGATC | AGCATACACA | 360 |
| AATTACAAAA | GTCTGAATTT | TTTTTTATCA | AGAGGGATAA | AACACCATGG | AAAATAAACT | 420 |
| TGGAATAAAC | TGAAAAANAA | AAAAAAAAA | GAT | | | 453 |

(2) INFORMATION FOR SEQ ID NO: 41:

(i) SEQUENCE CHARACTERISTICS:
        (A) LENGTH: 429 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
    (A) ORGANISM: HUMAN (xi) SEQUENCE DESCRIPTION: SEQ ID NO: 41:

```
CAGTTTATTC AAGTTTATTT TCATGGTGTT TTATCCCTCT TGATAAAAAA AAATTCAGAC      60

TTTTGTAATT TGTGTATGCT GATCTTCATC AAAAGGTTCA TTCTCTGGAT CAGAGTCAGT     120

GGTGTCAGAA TATCTATAAT GATCAGGTTC ATTGTCACTA ACATCTGGTG TTACAGAAGT     180

TGAACTGCTA GCCTCTGGAT TTGACGGCTC CTCTACTGTT TTTGTGAAGT ACAGCTTCAC     240

CTTAAAATTT GGAGAAAAGT ATCGGTTGGC TTTGTCTTTA TTTGCTTTGT CAAGATCATT     300

TTTTGTTAAA GTAAGTACTA AGATATTCCT TGTCATTATC TGCACGCTCT AATACTGCAA     360

ATGGCTATCC GATTTCCTGG ATCCACCATA GGNCTTCCNA TTTCCAACTT TTCCCTGNGG     420

TTCCCCCGG                                                             429
```

(2) INFORMATION FOR SEQ ID NO: 42:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 42:

```
TAAAAAAGGA CAAAATGTTT CACTTTTGGG TAAATACATT CTTCATACCA GGACCAGAGG      60

AAACCTCAGA AAAAGTAGAA AATGGAAGTC TATGTGATCA AGAAATCCGA TAGCATTTGC     120

NGTATAGAGC GTGCAGATAA TGNCAAGGAA TATCTAGTAC TTACTTTAAC CAAAAANTGA     180

TCTTGACAAA GCAAATAAAG NCCAACCNAC CGNTACTTTT CTCCCAATTT TTAGGGGG      238
```

(2) INFORMATION FOR SEQ ID NO: 43:

(i) SEQUENCE CHARACTERISTICS:
        (A) LENGTH: 332 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 43:

```
CGTCTTCTCC CCATTCCGCT GCCGCCGCTG CCAGGCCTCT GCGCTGCTGA GGAGAAGCAG      60

GCCCAGTCGC TGCAACCATC CAGCAGCCGC CGCAGCAGCC ATTACCCGGC TGCGGTCCAG     120

AGCCAAGCGG CGGCAGAGCG AGGGGCATCA GCTACCGCCA AGTCCAGAGC CATTTCCATC     180
```

```
CTGCAGAAGA AGCCCCGCCA CCAGCAGCTT CTGCCATCTC TCTCCTCCTT TTCTTCAGCC         240

ACAGGCTCCC AGACATGACA GCCATCATCA AAGAGATCGT TAGCAGAAAC AAAAGGAGAT         300

ATCAAGAGGA TGGATTCGAC TTAGACTTGA CC                                      332
```

(2) INFORMATION FOR SEQ ID NO: 44:

(i) SEQUENCE CHARACTERISTICS:
        (A) LENGTH: 543 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 44:

```
TTTTTTTTTT ACAATTGAGA AAACATATTT AATAAATCAT TGTCAATTTT TATAATGTTT          60

CAAGCCCATT CTTTGTTGAT AGCCTCCACA TTTATATGGT TAAGTCATTG TTGCTGTGTT         120

TCTTACCTAT GACATTATTT TTATATCCCT TCATTTGTGG ATCTTAAGAT GTTGCAGAAG         180

GTTCATTCCT GTACCCCAAT ACAGATTCAC TTCCTTTAGC TGCCTTTTCT AGCACCAATA         240

TGCTTTAAAA AAAAATGCGC AAACAACAAN GCAGTGACAG CGGCCAATTC CTCGAATGTC         300

CAGATTAATA ACTGTAGCAT GCTAAAGAAA GGTGTGTGTA AATAGCTCGG AGATGGGTAT         360

ATGGTCCAGA GTCCAGCATA AAATTATTTC CTTTCTGAGC ATTCCCTCCA TTGCCCCTAA         420

CCCGAATACA TGCATTAGAA TGGTAGCANA ACCCTTNCGG AAACCTCTCT TAGCCAACTG         480

CAAACTTATC TGTTGCCACA AGTGCAAAGG GGGTAGGATG TGAANCCAGT ATATTCCNCA         540

AAG                                                                      543
```

(2) INFORMATION FOR SEQ ID NO: 45:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 45:

```
AAGCTGTGTC ATGTATATAC CTTTTTGTGT CAAAAGGACA TTTAAAATTC AATTAGGATT          60

AATAAAGATG GCACTTTCCC GTTTTATTCC AGTTTTATAA AAAGTGGAGA CAGACTGATG         120

TGTATACGTA GGAATTTTTT CCTTTTGTGT TCTGTCACCA ACTGAAGTGG CTAAAGAGCT         180

TTGTGATATA CTGGTTCACA TCCTACCCCT TTGCACTTGT GGCAACAGAT AAGTTTGCAG         240

TTGGCTAAAG AGAGGTTTNC CGAAGGGTTT TGGCTACATT C                            281
```

(2) INFORMATION FOR SEQ ID NO: 46:

(i) SEQUENCE CHARACTERISTICS:
        (A) LENGTH: 455 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 46:

GTTACAATTG AGAAAACATA TTTAATAAAT CATTGTCAAT TTTNATAATG TTTCAAGCCC      60

ATTCTTTGTT GATAGCCTCC ACATTTATAT GGTTAAGTCA TTGTTGCTGT GTTTCTTACC     120

TATGACATTA TTTTNATATC CCTTCATTTG TGGATCTTAA GATGTTGCAG AAGGTTCATT     180

CCTGTACCCC AATACAGATT CACTTCCTTT AGCTGCCTTT NCTAGCACCA ATATGCTTTA     240

AAAAAAAATG CGCAAACAAC AAGCAGTGAC AGCGGCCAAT TCCTCGAATG TCCAGATTAA     300

TAACTGTAGC ATGCTAAAGA AAGGTGTGTG TAAATAGCTG GAGATGGTAT ATGGTCCAGA     360

GTCCAGCATA AAATTATTTC CTTTCTGAGG CATTCCCTCC ATTCCCCTAA CCCGGATACA     420

TGCATTAGGA ATGTAGCAAA ACCCTTCGGG GAACC                                455

(2) INFORMATION FOR SEQ ID NO: 47:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 47:

TTTTTTTTTT TTTACAATTG AGAAAACATA TTTAATAAAT CATTGTCAAT TTTTATAATG      60

TTTCAAGCCC ATTCTTTGTT GATAGCCTCC ACATTTATAT GGTTAAGTCA TTGTTGCTGT     120

GTTTCTTACC TATGACATTA TTTTTATATC CCTTCATTTG TGGATCTTAA GATGTTGCAG     180

AAGGTTCATT CCTGTACCCC AATACAGATT CACTTCCTTT AGCTGCCTTT TCTAGCACCA     240

ATATGCTTTA AAAAAAAATG CGCAAACAAC AAGCAGTGAC AGCGGCCAAT TCCTCGAATG     300

TCCAGATTAA TAACTGTAGC ATGCTAAAGA AAGGTGTGTG TAAATAGCTG GAGATGGTAT     360

ATGGTCCAGA GTCCAGCATA AAATTATTCC TT                                   392

(2) INFORMATION FOR SEQ ID NO: 48:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (A) ORGANISM: HUMAN (xi) SEQUENCE DESCRIPTION: SEQ ID NO: 48:

GTTTCGGAAC GAGGGCGGCT GACAGCTATT GAATAAGTGC ATCATAAATC TTCAAAGAAA      60

AAAAACGCTT ACTGTAGAAT CTCAAATTGA AAATTTCTGT GCAGCATTAC AAAATATTTT     120

ATATTTAATG AGAAAAAAGA AGCTTGCAGG CAGCACATGA AGCATCCACA GCAGGTATTA     180

TGATTGAAAA CTAGTAAAAT AAGTGTAAGT TGTTGACTGA TGTAGGTACT AACAGCATCT     240

GAATTTTAGC ACTGGCCTTG ATTACACAGG AGATGGAGAA GTCGTTACAA TTGAGAAAAC     300

ATATTTAATA AATCATTGTC AATTTTTATA ATGTTTCAAG CCCATTCTTT GTTGATAGCC     360

TCCACATTTA TATGGTTAAG TCATTGTTGC TGTGTTTCTT ACCTATGACA TTATTTTNAT     420

ATCCCTTCAT TTGTGGATCT TAAGATGTNG CAGAAGGTTC ATTCCTGNAC CCCA           474

(2) INFORMATION FOR SEQ ID NO: 49:

(i) SEQUENCE CHARACTERISTICS:
             (A) LENGTH: 241 base pairs
             (B) TYPE: nucleic acid
             (C) STRANDEDNESS: single
             (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (A) ORGANISM: HUMAN (xi) SEQUENCE DESCRIPTION: SEQ ID NO: 49:

GCGGCCGCGG NGGNTGCAGC TCCANGNAGG GGGTCTGAGT CGCCTGTCAC CATTTNCAGG      60

GCTGGGAACG CCGGAGAGTT GGTCTCTCCC CTTCTACTGC CTCCAACACG GCGGCNGCGG     120

CGGCGGCACA TCCAGGGACC CGGGCCGGTT TTAAACCTCC CGTCCGCCGC CGCCGCACCC     180

CCCAGTGGCC CGGGCTCCGG AGNCCGCCTG GCGGAGGCAA GCCGTTCGGA GGGATTATTC     240

G                                                                    241

(2) INFORMATION FOR SEQ ID NO: 50:

(i) SEQUENCE CHARACTERISTICS:
             (A) LENGTH: 405 base pairs
             (B) TYPE: nucleic acid
             (C) STRANDEDNESS: single
             (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (A) ORGANISM: HUMAN (xi) SEQUENCE DESCRIPTION: SEQ ID NO: 50:

TTACAATTGA GAAAACATAT TTAATAAATC ATTGTCAATT TTTATAATGT TTCAAGCCCA      60

TTCTTTGTTG ATAGCCTCCA CATTTATATG GTTAAGTCAT TGTTGCTGTG TTTCTTACCT     120

ATGACATTAT TTTTATATCC CTTCATTTGT GGATCTTAAG ATGTTGCAGA AGGTTCATTC     180

-continued

```
CTGTACCCCA ATACAGNTTC ACTTCCTTTA GCTGCCTTTT CTAGCACCAA TATGCTTTAA      240

AAAAAAANTG CGCAAACAAC AAGCAGTGAC AGCGGCCAAT TCCTCGATTG TCCNGATTAA      300

TANCTGTAGC ATGCTAAAGG AAGGTGTGTG TAAATAGGCT GGAGATGGGT ATATGGNTCC      360

AGAGTCCAGC TGAANATTGT NTCCTTNCTG AGCNTTCCCT NCATT                     405
```

(2) INFORMATION FOR SEQ ID NO: 51:

(i) SEQUENCE CHARACTERISTICS:
        (A) LENGTH: 473 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 51:

```
ANAGTTNGTG TGCAGCATTA CAAAATATTT TATATTTAAT GAGAAAAAAG AAGCTTGCAG       60

GCAGCACATG AAGCATCCAC AGCAGGTATT ATGATTGAAA ACTAGTAAAA TAAGTGTAAG      120

TTGTTGACTG ATGTAGGTAC TAACAGCATC TGAATTTTAG CACTGGCCTT GATTACACAG      180

GAGATGGAGA AGTCGTTACA ATTGAGAAAA CATATTTAAT AAATCATTGT CAATTTTTAT      240

AATGTTTCAA GCCCATTCTT TGTTGATAGC CTCCACATTT ATATGGGTTA AGTCATTGTT      300

GCTGTGTTTC TTACCTATGA CATTATTTTT ATATCCCTTC ATTTGTGGGA TCTTAAGGAT      360

GTTGCAGGAA GGGTTCATTC CCTGTACCCC CAATACAGAT TCACTTCCTT TAGGCTGCCT      420

TTTCTAGGCA CCAATATGCT TTAAAAAAAA ATGGCGGCAA ACAACAGGCN GTG            473
```

(2) INFORMATION FOR SEQ ID NO: 52:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 52:

```
TCAAATCCAG AGGCTAGCAG TTCAACTTCT GTAACACCAG ATGTTAGTGA CAATGAACCT       60

GATCATTATA GATATTCTGA CACCACTGAC TCTGATCCAG AGAATGAACC TTTTGATGAA      120

GATCAGCATA CACAAATTAC AAAAGTCTGA ATTTTTTTTT ATCAAGAGGG ATAAAACACC      180

ATGAAAATAA ACTTGAATAA ACTGAAAATG GGACCTTTTT TTTTTTTAAT GGGCAATAGG      240

GACATTGTGT CAGGATTACC AGTTATAGGG GACAATTCTC TTTTCCCTGG ACCCAATCTT      300

GTTTTTTACC CTATACATCC ACCGGGGGTT TTTTGACACT TGTTTGTCCC AGTTGGAAAA      360

AGGGTTGTNT TGGCCGTNGT CCAGGATTAT ACCCTT                                396
```

(2) INFORMATION FOR SEQ ID NO: 53:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 53:

```
GGGCTCCGGA GCCGCCGGCG GAGGCAGCCG TTCGGAGGAT TATTCGTCTT CTCCCCATTC    60

CGCTGCCGCC GCTGCCAGGC CTCTGCTGCT GAGGAGAAGC AGGCCCAGTC GCTGCAACCA   120

TCCAGCAGCC GCCGCAGCAG CCATTACCCG GCTGCGGTCC AGAGCCAAGA CGCAGAGAGG   180

GCATCAGCTA CCGCCAAGTC AGAGCATTTC CATCTCAGAA GAAG                   224
```

(2) INFORMATION FOR SEQ ID NO: 54:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 54:

```
GATCCACAAA TGAAAGGGAT ATAAAAATAA TGTCATAGGT AAGAAACACA GCAACAATGA    60

CTTAACCATA TAAATGTGGA GGCTATCAAC AAAGAATGGG CTTGAAACAT TATAAAANTT   120

GACAATGATT TATTAAATAT GTTTNCTCAA TTGT                              154
```

(2) INFORMATION FOR SEQ ID NO: 55:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 55:

```
TAGAATCTCA AATTGAAAAT TTCTGTGCAG CATTACAAAA TATTTTATAT TTAATGAGAA    60

AAAAGAAGCT TGCAGGCAGC ACATGAAGCA TCCACAGCAG GTATTATGAT TGAAAACTAG   120

TAAAATAAGT GTAAGTTGTT GACTGATGTA GGTACTAACA GCATCTGAAT TTTAGCACTG   180
```

```
GCCTTGATTA CACAGGAGAT GGAGAAGTCG TTACAATTGA GAAAACATAT TTAATAAATC     240

ATTGTCAATT NTTAATAATG GTTTCAAGCC CATNCTTTNG TTGATAGCCT CCNCCATTTT     300

ATATCGGTTA AGTCATTGGG TGCTNGTGTT TCTTACCTAT GACCATTATN TTTATATCCC     360
```

(2) INFORMATION FOR SEQ ID NO: 56:

(i) SEQUENCE CHARACTERISTICS:
        (A) LENGTH: 150 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN (xi) SEQUENCE DESCRIPTION: SEQ ID NO: 56:

```
ATGACCTTTG ATGAGATCAG CATACACAAA TACAAAAGTC TGAGTTTTTT TTTATCAGGA      60

GGGATAAACA CCATGAAATA AACTTGAATA AACTGAAAAT GGACCTTTTT TTTTTAATGG     120

CATAGGCATG GGCGTTCCCG TTTGGACAAT                                      150
```

(2) INFORMATION FOR SEQ ID NO: 57:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HUMAN EXON 2B (xi) SEQUENCE DESCRIPTION: SEQ ID NO: 57:

```
CCGTTCGTAC GAGAATCGCT GTCCTCTCCT TCTCATTTTT GTTAATGGTG GCTTTTTGTT      60

TGTTTGTTTT GTTTTAAGGT TTTTGGATTC AAAGCATAAA AACCATTACA AGATATACAA     120

TCTGTAAGTA TGTTTTCTTA TTTGTATGCT TGCAAATATC TTCTAAAACA ACTATTAAGT     180

GAAAGTTATN TGCTTGTTAG AGTGAGGTAG AGTTAAAGAT ACATTTTAAC AGAATTGTAT     240

TCCTAAACCG ATTAAGTCAA GAAGTCCAAG AGCATTGTTA GATCATTTAG AAAGTGTAGT     300

GATGAGGTAA AACATTGTTG GCACAGATTC ATGTTANCTG ATNTGCTTTA AATGANTTGG     360

CATNTAGCCC ATATTTGAGC CCATAACCGT GTGGTAATTT GAAGTGTNAT TNACAGTAGA     420

GCTTTTGTTA AAGCACTAAT AGCATNTTCC ANGGAGGTAT AATTCAGAGT GAATATAAAT     480

TTGTTTATCC TGTGTCTTTA GAGCTATTGA CTGAAAAAGC TGTTAGGCAT TNTCTAACTG     540

T                                                                    541
```

(2) INFORMATION FOR SEQ ID NO: 58:

(i) SEQUENCE CHARACTERISTICS:
        (A) LENGTH: 871 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: human (vii) IMMEDIATE SOURCE:
        (B) CLONE: part of IMAGE clone 264611

(xi) SEQUENCE DESCRIPTION: SEQ ID NO: 58:

```
CGGCCGCGGC GGCTGCAGCT CCAGGGAGGG GGTCTGAGTC GCCTGTCACC ATTTCCAGGG     60
CTGGGAACGC CGGAGAGTTG GTCTCTCCCC TTCTACTGCC TCCAACACGG CGGCGGCGGC    120
GGCGGCACAT CCAGGGACCC GGGCCGGTTT TAAACCTCCC GTCCGCCGCC GCCGCACCCC    180
CCGTGGCCCG GGCTCCGGAG GCCGCCGGCG GAAGCAGCCG TTCGGAGGAT TATTCGTCTT    240
CTCCCCATTC CGCTGCCGCC GCTGCCAGGC CTCTGGCTGC TGAGGAGAAG CAGGCCCAGT    300
CGCTGCAACC ATCCAGCAGC CGCCGCAGCA GCCATTACCC GGCTGCGGTC CAGAGCCAAG    360
CGGCGGCAGA GCGAGGGGCA TCAGCTACCG CCAAGTCCAG AGCCATTTCC ATCCTGCAGA    420
AGAAGCCCCG CCACCAGCAG CTTCTGCCAT CTCTCTCCTC CTTTTTCTTC AGCCACAGGC    480
TCCCAGACAT GACAGCCATC ATCAAAGAGA TCGTTAGCAG AAACAAAAGG AGATATCAAG    540
AGGATGGATT CGACTTAGAC TTGACCTGTA TCCATTTCTG CGGCTGCTCC TCTTTACCTT    600
TCTGTCACTC TCTTAGAACG TGGGAGTAGA CGGATGCGAA AATGTCCGTA GTTTGGGTGA    660
CTATAACATT TAACCCTGGT CAGGTTGCTA GGTCATATAT TTTGTGTTTC CTTTCTGTGT    720
ATTCAACCTA GGGTGTGTTT GGCTAGACGG AACTCTTGCC TGGTTGCAAG TGTCAAGCCA    780
CCGATTGCTT TCTTAGGCTA TCTATATGGT CTCTTCCTGA GGGCTATTGT CCGTTAATAC    840
AGAATACAGT AAGGAGAGGA CAGCGATCCT A                                    871
```

(2) INFORMATION FOR SEQ ID NO: 59:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: human (vii) IMMEDIATE SOURCE:
        (B) CLONE: part of IMAGE clone 264611

(xi) SEQUENCE DESCRIPTION: SEQ ID NO: 59:

```
CTAATGTTTT AAAAAGTATT CTTTTAGTTT GATTGCTGCA TATTTCAGAT ATTTCTTTCC     60
TTAACTAAAG TAACTCAGAT ATTTATCCAA ACATTATTGC TATGGGATTT CCTGCAGAAA    120
GACTTGAAGG CGTATACAGG AACAATATTG ATGATGTAGT AAGGTAAGAA TGCTTTGATT    180
TTCTATTTCA AATATTGATG TTTATATTCA TGTTGTGTTT TCATTTAGAA AAGATTTCTA    240
AGCCACAGAA AAAGATACTT TGTGATGTAA ACTATTATTG TAGTGCTCTA TAATCATTTT    300
```

```
TTGGCTTACC GTACCTAATG GACTTCAGGG GGATACAGTT CATTTGATAA GAACTGACCT      360

TATACATTAC ATAATCAGGT ACTTATGTGA TAAGGANAGG ACACATCTCG TACAANGAGG      420
```

(2) INFORMATION FOR SEQ ID NO: 60:

(i) SEQUENCE CHARACTERISTICS:
        (A) LENGTH: 510 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: human (vii) IMMEDIATE SOURCE:
        (B) CLONE: part of IMAGE clone 264611

(xi) SEQUENCE DESCRIPTION: SEQ ID NO: 60:

```
CTCATTTTTG TTAATGGTGG CTTTTTGTTT GTTTGTTTTG TTTTAAGGTT TTTGGATTCA       60

AAGCATAAAA ACCATTACAA GATATACAAT CTGTAAGTAT GTTTTCTTAT TTGTATGCTT      120

GCAAATATCT TCTAAAACAA CTATTAAGTG AAAGTTATCT GCTTGTTAGA GTGAGGTAGA      180

GTTAAAGATA CATTTTAACA GAATTGTATT CCTAAACCGA TTAAGTCAAG AAGTCCAAGA      240

GCATTGTTAG ATCATTTAGA AAGTGTAGTG ATGAGGTAAA ACATTGTTGG CACAGATTCA      300

TGTTANCTGA TNTGCTTTAA ATGANTTGGC ATCTAGCCCA TATTTGAGCC CATAACCGTG      360

TGGTAATTTG AAGTGTNATT NACAGTAGAG CTTTTGTTAA AGCACTAATA GCATNTTCCA      420

NGGAGGTATA ATTCAGAGTG AATATAAATT TGTTTATCCT GTGTCTTTAG AGCTATTGAC      480

TGAAAAAGCT GTTAGGCATT NTCTAACTGT                                      510
```

(2) INFORMATION FOR SEQ ID NO: 61:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC OLIGONUCLEOTIDE"

(iii) HYPOTHETICAL: NO (iv) ANTI-SENSE: NO (xi) SEQUENCE DESCRIPTION: SEQ ID NO: 61:

```
GGTGGCGACG ACTCCTGGAG CC                                               22
```

(2) INFORMATION FOR SEQ ID NO: 62:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: human (vii) IMMEDIATE SOURCE:
              (B) CLONE: part of IMAGE clone 264611

(xi) SEQUENCE DESCRIPTION: SEQ ID NO: 62:

```
TAAAACACAG CATAATATGT GTCACATTAT AAAGATTCAG GCAATGTTTG TTAGTATTAG      60

TACTTTTTTT TCTTCCTAAG TGCAAAAGAT AACTTTATAT CACTTTTAAA CTTTTCTTTT     120

AGTTGTGCTG AAAGACATTA TGACACCGCC AAATTTAATT GCAGAGGTAG GTATGAATGT     180

ACTGTACTAT GTTGTATAAC TTAAACCCGA TAGACTGTAT CTTACTGTCA TAACAATAAT     240

GAGTCATCCA GATTATCGAG TGAGATACAT ATTTATCTTA AGAATTATCT TTAAAAATTT     300

CAAAAATTTT AATTTTACTG TTGTGTTTTA GGAAAAAGTA TTGCATAAAG CTATTAATAT     360

TGTCAGGAAG ACTAAAGTGC AGCATA                                          386
```

(2) INFORMATION FOR SEQ ID NO: 63:

(i) SEQUENCE CHARACTERISTICS:
              (A) LENGTH: 381 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: human (vii) IMMEDIATE SOURCE:
              (B) CLONE: part of IMAGE clone 264611

(xi) SEQUENCE DESCRIPTION: SEQ ID NO: 63:

```
TAAAACACAG CATAATATGT GTCACATTAT AAAGATTCAG GCAATGTTTG TTAGTATTAG      60

TACTTTTTTT TCTTCCTAAG TGCAAAAGAT AACTTTATAT CACTTTTAAA CTTTTCTTTT     120

AGTTGTGCTG AAAGACATTA TGACACCGCC AAATTTAATT GCAGAGGTAG GTATGAATGT     180

ACTGTACTAT GTTGTATAAC TTAAACCCGA TAGACTGTAT CTTACTGTCA TAACAATAAT     240

GAGTCATCCA GATTATCGAG TGAGATACAT ATTTAAGAAT TATCTTTAAA AATTTCAAAA     300

ATTTTAATTT TACTGTTGTG TTTTAGGAAA AAGTATTGCA TAAAGCTATT AATATTGTCA     360

GGAAGACTAA AGTGCAGCAT A                                               381
```

(2) INFORMATION FOR SEQ ID NO: 64:

(i) SEQUENCE CHARACTERISTICS:
              (A) LENGTH: 724 base pairs
              (B) TYPE: nucleic acid
              (C) STRANDEDNESS: single
              (D) TOPOLOGY: linear (iii) HYPOTHETICAL: NO (iv) ANTI-SENSE: NO (vi) ORIGINAL SOURCE:
              (A) ORGANISM: human (xi) SEQUENCE DESCRIPTION: SEQ ID NO: 64:

```
TTTTCTACCT CTAATNGCTG ACNTATGCTA CCAGTCCGTA TAGCGTAAAT TCCCAGAATA      60
```

-continued

```
TATCCTCCTG AATAAAATGG GGGAAAATAA TACCTGGCTT CCTTAATGAT TATATTTAAN      120

ACTTATCAAN ANACTATTTT CTATTTAACA ATTAGAAAGT TAAGCAATAC ATTATTTTTC      180

TCTGGAATCC AGTGTTTCTT TTAAATACCT GTTAAGTTTG TATGCAACAT TTCTAAAGTT     240

ACCTACTTGT TAATTAAAAA TTCAAGAGTT TTTTTTTCTT ATTCTGAGGT TATCTTTTTA     300

CCACAGTTGC ACAATATCCT TTTGAAGACC ATAACCCACC ACAGCTAGAA CTTATCAAAC     360

CCTTTTGTGA AGATCTTGAC CAATGGCTAA GTGAAGATGA CAATCATGTT GCAGCAATTC     420

ACTGTAAAGC TGGAAAGGGA CGAACTGGTG TAATGATATG TGCATATTTA TTACATCGGG     480

GCAAATTTTT AAAGGCACAA GAGGCCCTAG ATTTCTATGG GGAAGTAAGG ACCAGAGACA     540

AAAAGGTAAG TTATTTTTTG ATGTTTTCC TTTCCTCTTC CTGGATCTGA GAATTTATTG     600

GAAACAGAT TTTGGGTTTC TTTTTTTCTT CAGTTTTATT GAGGTGTAAT TGCACAAGTA     660

AAAATTATAT ATAAATACAA TGTATAATAT GATGTTTGGA ATGTATGTGT ATATACATTG     720

TGAA                                                                  724
```

(2) INFORMATION FOR SEQ ID NO: 65:

(i) SEQUENCE CHARACTERISTICS:
        (A) LENGTH: 542 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human (xi) SEQUENCE DESCRIPTION: SEQ ID NO: 65:

```
AAGGTCAAAT GTCTAATGTA TATATGTTCT TAAATGGCTA CGACCCAGTT ACCATAGCAA       60

TTAGTGAAA TAACTATAAT GGAACATTTT TTTTCAATTT GGCTTCTCTT TTTTTTCTGT      120

CCACCAGGGA GTAACTATTC CCAGTCAGAG GCGCTATGTG TATTATTATA GCTACCTGTT     180

AAAGAATCAT CTGGATTATA GACCAGTGGC ACTGTTGTTT CACAAGATGA TGTTTGAAAC     240

TATTCCAATG TTCAGTGGCG GAACTTGCAG TAAGTGCTTG AAATTCTCAT CCTTCCATGT     300

ATTGGAACAG TTTTCTTAAC CATATCTAGA AGTTTACATA AAAATTTAGA AAGAAATTTA     360

CCACATTTGA AATTTATGCA GGAGACTATA TTTCTGAAGC ATTTGAACAA ATTAATTAGC     420

TTTGTTGTTC AACTCATTGG GCTAAAGAAG CCAAAAGCAA TGGGTTTTAA TGTAGTCGAA     480

GCCAAATTAT ATTTATGAAA GAAATATTCT GTGTTATAAC CACCAAATAC AGCCCAATTC     540

TG                                                                    542
```

(2) INFORMATION FOR SEQ ID NO: 66:

(i) SEQUENCE CHARACTERISTICS:
        (A) LENGTH: 638 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human (xi) SEQUENCE DESCRIPTION: SEQ ID NO: 66:

```
ACTCTGCCAC TAGAAGTCTA ATTTTGGGAC TTACTATTCA TGAAATAGGA ATTGACTTTN      60

ATATAAGTAA TAGGACCTTA TTTTGAAGGT TCAAACTGGA GAAAATCTTA CATTGTTTAT     120

ATTTTTATTT CATTTANTTC AGTTGATTTG CTTGAGATCA AGATTGCAGA TACAGAATCC     180

ATATTTCGTG TATATTGCTG ATATTAATCA TTAAAATCGT TTTTGACAGT TTGACAGTTA     240

AAGGCATTTC CCTGTGAAAT AATACTGGTA TGTATTTAAC CATGCAGATC CTCAGTTTGT     300

GGTCTGCCAG CTAAAGGTGA AGATATATTC CTCCAATTCA GGACCCACAC GACGGGAAGA     360

CAAGTTCATG TACTTTGAGT TCCCTCAGCC GTTACCTGTG TGTGGTGATA TCAAAGTAGA     420

GTTCTTCCAC AAACAGAACA AGATGCTAAA AAAGGTTTGT ACTTTACTTT CATTGGGAGA     480

AATATCCAAA ATAAGGACAG ATTANAAGCT NTATTNTATT TTATGACATG TAAGGAACTA     540

TAATTTGTTT TCTATTAGAT CTGCCAGGTG TTTTGCTTAC TCTGGCATTG GTGAGACATT     600

ATANGGGTAA ATAATCCTGT TTGAAGGAAN AGGCCTAT                             638
```

(2) INFORMATION FOR SEQ ID NO: 67:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human (xi) SEQUENCE DESCRIPTION: SEQ ID NO: 67:

```
TTTATCTTAG ATCTTGTGAG ATTGTATTTT TGGTTTAAAA TTTGAGAATT TGAGTGAAGA      60

AAAATCATGT GAATGAAAAT GCAACAGATA ACTCAGATTG CCTTATAATA GTCTTTGTGT     120

TTACCTTTAT TCAGAATATC AAATGATAGT TTATTTTGTT GACTTTTTGC AAATGTTTAA     180

CATAGGTGAC AGATTTTCTT TTTTAAAAAA ATAAAACATC ATTAATTAAA TATGTCATTT     240

CATTTCTTTT TCTTTTCTTT TTTTTTTTTT TAGGACAAAA TGTTTCACTT TTGGGTAAAT     300

ACATTCTTCA TACCAGGACC AGAGGAAACC TCAGAAAAAG TAGAAAATGG AAGTCTATGT     360

GATCAAGAAA TCGATAGCAT TTGCAGTATA GAGCGTGCAG ATAATGACAA GGAATATCTA     420

GTACTTACTT TAACAAAAAA TGATCTTGAC AAAGCAAATA AAGACAAAGC CAACCGATAC     480

TTTTCTCCAA ATTTTAAGGT CAGTTAAATT AAACATTTTG TGGGGGTTGG TGACTTGTAT     540

GTATGTGATG TGTGTTTAAT TCTAGGAGTA CAG                                  573
```

(2) INFORMATION FOR SEQ ID NO: 68:

(i) SEQUENCE CHARACTERISTICS:
        (A) LENGTH: 587 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human (xi) SEQUENCE DESCRIPTION: SEQ ID NO: 68:

```
GGAGGCAGAG GTTGCAGTGA GCCAAGATCA TGCCACTGCA CTCCAGCTTG GCAACAGAGC        60

AAGACTCTTG TCTCCAGAAA TAAAAATAAA TAAATTGTAT TAACATCCTG ATAGTTTATC       120

TGTTTAGTAC CTAGCAAGAA AGAAAATGTT GAACATCTTA AGAAGAGGGT CATTTAAAAG       180

GCCTCTTAAA GATCATGTTT GTTACAGTGC TTAAAAATTA ATATGTTCAT CTGCAAAATG       240

GAATAAAAAA TCTGTTAAAA ATATATTTCA CTAAATAGTT AAGATGAGTC ATATTTGTGG       300

GTTTTCATTT TAAATTTTCT TTCTCTAGGT GAAGCTGTAC TTCACAAAAA CAGTAGAGGA       360

GCCGTCAAAT CCAGAGGCTA GCAGTTCAAC TTCTGTAACA CCAGATGTTA GTGACAATGA       420

ACCTGATCAT TATAGATATT CTGACACCAC TGACTCTGAT CCAGAGAATG AACCTTTTGA       480

TGAAGATCAG CATACACAAA TTACAAAAGT CTGAATTTTT TTTTATCAAG AGGGATAAAA       540

CACCATGAAA ATAAACTTGA ATAAACTGAA AAAAAAAAAA AAAAAAA                     587
```

(2) INFORMATION FOR SEQ ID NO: 69:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human (xi) SEQUENCE DESCRIPTION: SEQ ID NO: 69:

```
TTTATCCAAA CATTATTGCT ATGGGATTTC CTGCAGAAAG ACTT                         44
```

(2) INFORMATION FOR SEQ ID NO: 70:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human (xi) SEQUENCE DESCRIPTION: SEQ ID NO: 70:

```
TTTATCCAAA CATTATTGCT ATGGATTTCC TGCAGAAAGA CTT                          43
```

(2) INFORMATION FOR SEQ ID NO: 71:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human (xi) SEQUENCE DESCRIPTION: SEQ ID NO: 71:

ATTATTGCTA TGGGATTTCC TGCAGAAAGA CTTGAAGGCG TATACAGGAA        50

(2) INFORMATION FOR SEQ ID NO: 72:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human (xi) SEQUENCE DESCRIPTION: SEQ ID NO: 72:

ATTATTGCTA TGGGATTTCC TGCAGAAAGA CTTGAAGACA GAAAGACAGG AA     52

(2) INFORMATION FOR SEQ ID NO: 73:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human (xi) SEQUENCE DESCRIPTION: SEQ ID NO: 73:

GCAGAAAGAC TTGAAGGCGT ATACA                                  25

(2) INFORMATION FOR SEQ ID NO: 74:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human (xi) SEQUENCE DESCRIPTION: SEQ ID NO: 74:

GCAGAAAGAC TTGAAGACAG AAAGACA                                27

(2) INFORMATION FOR SEQ ID NO: 75:

(i) SEQUENCE CHARACTERISTICS:
        (A) LENGTH: 20 amino acids
        (B) TYPE: amino acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 75:

Ala Pro Gly Arg Gly Ser Glu Ser Pro Val Thr Ile Ser Arg Ala Gly
1               5                   10                  15

```
Asn Ala Gly Glu
        20

(2) INFORMATION FOR SEQ ID NO: 76:

(i) SEQUENCE CHARACTERISTICS:
        (A) LENGTH: 22 amino acids
        (B) TYPE: amino acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 76:

Gln Leu Lys Val Lys Ile Tyr Ser Ser Asn Ser Gly Pro Thr Arg Arg
1               5                   10                  15
Glu Asp Lys Phe Met Tyr
        20

(2) INFORMATION FOR SEQ ID NO: 77:

(i) SEQUENCE CHARACTERISTICS:
        (A) LENGTH: 19 amino acids
        (B) TYPE: amino acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 77:

Lys Val Lys Leu Tyr Phe Thr Lys Thr Val Glu Glu Pro Ser Asn Pro
1               5                   10                  15
Glu Ala Ser (2) INFORMATION FOR SEQ ID NO: 78:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC OLIGO"

(iii) HYPOTHETICAL: NO (iv) ANTI-SENSE: NO (xi) SEQUENCE DESCRIPTION: SEQ ID NO: 78:

TGTTACCAAT CTGAAGTGGG AGCGGCCGCA TCTTTTTTTT TTTTTTTTTT          50

(2) INFORMATION FOR SEQ ID NO: 79:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "PCR PRIMER"

(iii) HYPOTHETICAL: NO
```

(iv) ANTI-SENSE: NO (xi) SEQUENCE DESCRIPTION: SEQ ID NO: 79:

TGTTACCAAT CTGAAGTGGG AGCGGCCGCG CTTTTTTTTT TTTTTTTTTT          50

(2) INFORMATION FOR SEQ ID NO: 80:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC OLIGO"

(iii) HYPOTHETICAL: NO (iv) ANTI-SENSE: NO (xi) SEQUENCE DESCRIPTION: SEQ ID NO: 80:

TGTTACCAAT CTGAAGTGGG AGCGGCCGCA GTTTTTTTTT TTTTTTTTTT          50

(2) INFORMATION FOR SEQ ID NO: 81:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC OLIGO"

(iii) HYPOTHETICAL: NO (iv) ANTI-SENSE: NO (xi) SEQUENCE DESCRIPTION: SEQ ID NO: 81:

AACTGGAAGA ATTAATTAAA GATCTTTTTT TTTTTTTTTT TTT                 43

(2) INFORMATION FOR SEQ ID NO: 82:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC OLIGO"

(iii) HYPOTHETICAL: NO (iv) ANTI-SENSE: NO (xi) SEQUENCE DESCRIPTION: SEQ ID NO: 82:

CTCGAGTTTT TTTTTTTTTT TTTT                                      24

(2) INFORMATION FOR SEQ ID NO: 83:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC OLIGO"

(iii) HYPOTHETICAL: NO (iv) ANTI-SENSE: NO (xi) SEQUENCE DESCRIPTION: SEQ ID NO: 83:

GATTCGGCAC GAG                                                              13

(2) INFORMATION FOR SEQ ID NO: 84:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC OLIGO"

(iii) HYPOTHETICAL: NO (iv) ANTI-SENSE: NO (xi) SEQUENCE DESCRIPTION: SEQ ID NO: 84:

TGTTACCAAT CTGAAGTGGG AGCGGCCGCA ATTTTTTTTT TTTTTTTTT                        49

(2) INFORMATION FOR SEQ ID NO: 85:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC OLIGO"

(iii) HYPOTHETICAL: NO (iv) ANTI-SENSE: NO (xi) SEQUENCE DESCRIPTION: SEQ ID NO: 85:

CTTTTGAGCA AGTTCAGCCT GGTTAAGT                                              28

(2) INFORMATION FOR SEQ ID NO: 86:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC OLIGO"

(iii) HYPOTHETICAL: NO (iv) ANTI-SENSE: NO (xi) SEQUENCE DESCRIPTION: SEQ ID NO: 86:

GAGGTGGCTT ATGAGTATTT CTTCCAGGGT AA                                         32

(2) INFORMATION FOR SEQ ID NO: 87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "SYNTHETIC OLIGO"

(iii) HYPOTHETICAL: NO (iv) ANTI-SENSE: NO (xi) SEQUENCE DESCRIPTION: SEQ ID NO: 87:

GGGTAAAAAG CAAAAGAATT                                              20

(2) INFORMATION FOR SEQ ID NO: 88:

(i) SEQUENCE CHARACTERISTICS:
           (A) LENGTH: 49 base pairs
           (B) TYPE: nucleic acid
           (C) STRANDEDNESS: single
           (D) TOPOLOGY: linear (ii) MOLECULE TYPE: other nucleic acid
           (A) DESCRIPTION:   /desc = "SYNTHETIC OLIGO"

(iii) HYPOTHETICAL: NO (iv) ANTI-SENSE: NO (xi) SEQUENCE DESCRIPTION: SEQ ID NO: 88:

TGTTACCAAT CTGAAGTGGG AGGGCCGCAT TTTTTTTTTT TTTTTTTT               49

(2) INFORMATION FOR SEQ ID NO: 89:

(i) SEQUENCE CHARACTERISTICS:
           (A) LENGTH: 41 base pairs
           (B) TYPE: nucleic acid
           (C) STRANDEDNESS: single
           (D) TOPOLOGY: linear (ii) MOLECULE TYPE: other nucleic acid
           (A) DESCRIPTION:   /desc = "SYNTHETIC OLIGO"

(iii) HYPOTHETICAL: NO (iv) ANTI-SENSE: NO (xi) SEQUENCE DESCRIPTION: SEQ ID NO: 89:

AACTGGAAGA ATTCGCGGCC GCCTTTTTTT TTTTTTTTTT T                      41

(2) INFORMATION FOR SEQ ID NO: 90:

(i) SEQUENCE CHARACTERISTICS:
           (A) LENGTH: 58 base pairs
           (B) TYPE: nucleic acid
           (C) STRANDEDNESS: single
           (D) TOPOLOGY: linear (ii) MOLECULE TYPE: other nucleic acid
           (A) DESCRIPTION:   /desc = "SYNTHETIC OLIGO"

(iii) HYPOTHETICAL: NO (iv) ANTI-SENSE: NO (xi) SEQUENCE DESCRIPTION: SEQ ID NO: 90:

TGTTACCAAT CTGAAGTGGG AGCGGCCGCA CCAATTTTTT TTTTTTTTTT TTTTTTTT    58

(2) INFORMATION FOR SEQ ID NO: 91:

(i) SEQUENCE CHARACTERISTICS:
           (A) LENGTH: 50 base pairs
           (B) TYPE: nucleic acid
           (C) STRANDEDNESS: single
           (D) TOPOLOGY: linear (ii) MOLECULE TYPE: other nucleic acid
           (A) DESCRIPTION:   /desc = "SYNTHETIC OLIGO"

```
      (iii) HYPOTHETICAL: NO (iv) ANTI-SENSE: NO (xi) SEQUENCE DESCRIPTION: SEQ ID NO: 91:

TGTTACCAAT CTGAAGTGGG AGCGGCCGCA TTTTTTTTTT TTTTTTTTTT                  50

(2) INFORMATION FOR SEQ ID NO: 92:

(i) SEQUENCE CHARACTERISTICS:
           (A) LENGTH: 50 base pairs
           (B) TYPE: nucleic acid
           (C) STRANDEDNESS: single
           (D) TOPOLOGY: linear (ii) MOLECULE TYPE: other nucleic acid
           (A) DESCRIPTION:    /desc = "SYNTHETIC OLIGO"

(iii) HYPOTHETICAL: NO (iv) ANTI-SENSE: NO (xi) SEQUENCE DESCRIPTION: SEQ ID NO: 92:

TGTTACCAAT CTGAAGTGGG AGCGGCCGCG CTTTTTTTTT TTTTTTTTTT                  50

(2) INFORMATION FOR SEQ ID NO: 93:

(i) SEQUENCE CHARACTERISTICS:
           (A) LENGTH: 51 base pairs
           (B) TYPE: nucleic acid
           (C) STRANDEDNESS: single
           (D) TOPOLOGY: linear (ii) MOLECULE TYPE: other nucleic acid
           (A) DESCRIPTION:    /desc = "SYNTHETIC OLIGO"

(iii) HYPOTHETICAL: NO (iv) ANTI-SENSE: NO (xi) SEQUENCE DESCRIPTION: SEQ ID NO: 93:

TGTTACCAAT CTGAAGTGGG AGCGGCCGCG GTTTTTTTTT TTTTTTTTTT T                51

(2) INFORMATION FOR SEQ ID NO: 94:

(i) SEQUENCE CHARACTERISTICS:
           (A) LENGTH: 15 base pairs
           (B) TYPE: nucleic acid
           (C) STRANDEDNESS: single
           (D) TOPOLOGY: linear (ii) MOLECULE TYPE: other nucleic acid
           (A) DESCRIPTION:    /desc = "SYNTHETIC OLIGO"

(iii) HYPOTHETICAL: NO (iv) ANTI-SENSE: NO (xi) SEQUENCE DESCRIPTION: SEQ ID NO: 94:

GAATTCGGCA CAGAG                                                        15
```

DIAGNOSIS OF SUSCEPTIBILITY TO CANCER AND TREATMENT THEREOF

This Application claims priority to Provisional Application No. 60/042,655, filed Apr. 2, 1997 and No. 60/033,147, filed Dec. 13, 1996. Priority is also claimed to PCT/96GB/02588, filed Oct. 22, 1996, which claims priority to Provisional Application No. 60/005,840, filed Oct. 23, 1995.

The present invention relates to methods of determining whether a patient has cancer or is susceptible to cancer, and it relates to methods of treating cancer, particularly prostate cancer.

Carcinoma of the prostate has become a most significant disease in many countries. Over the last 20 years the mortality rates have doubled and it is now the second commonest cause of male cancer deaths in England and Wales (Mortality Statistics: Cause England and Wales. OPCS DH2 19, 1993, Her Majesty's Stationery Office). The prevalence of prostate cancer has increased by 28% in the last decade and this disease now accounts for 12% of the total cancers of men in England and Wales (Cancer Statistics: Registrations England and Wales. OPCS MBI No 22, 1994, Her Majesty's Stationery Office). This increase and the recent deaths of many public figures from prostatic cancer have served to highlight the need to do something about this cancer. It has been suggested that the wider availability of screening may limit mortality from prostate cancer.

Prostate cancer screening currently consists of a rectal examination and measurement of prostate specific antigen (PSA) levels. These methods lack specificity as digital rectal examination has considerable inter-examiner variability (Smith & Catalona (1995) *Urology* 45, 70–74) and PSA levels may be elevated in benign prostatic hyperplasia (BPH), prostatic inflammation and other conditions. The comparative failure of PSA as a diagnostic test was shown in 366 men who developed prostate cancer while being included in the Physicians Health Study, a prospective study of over 22,000 men. PSA levels were measured in serum, which was stored at the start of the study, and elevated levels were found in only 47% of men developing prostate cancer within the subsequent four years (Gann et al (1995) *JAMA* 273, 289–294).

Present screening methods are therefore unsatisfactory.

Cytogenetic and allele loss studies have pointed to a number of chromosomal regions of potential involvement in prostate cancer. Cannon-Albright & Eeles (1995) *Nature Genetics* 9, 336–338 (Reference 1) discuss candidate regions for tumour suppressor prostate cancer susceptibility loci from loss-of-heterozygosity (LOH) studies which occur on human chromosome regions 3p, 7q, 8p, 9q, 10p, 10q, 11p, 13q, 16q, 17p, 18q and Y; whereas Broilman et al 1990) *Cancer Res.* 50 3795–3803 surveyed cytogenetic information on human prostate adenocarcinoma which indicated loss of chromosomes 1, 2, 5 and Y and gain of 7, 14, 20 and 22, with rearrangements involving chromosome arms 2p, 7q and 10q being most common. Studies by Gao et al 1994) *Oncogene* 9, 2999–3003 indicate that a positive mutator phenotype in at least one of chromosomes 3p, 5q, 6p, 7p, 8p, 10q, 11p, 13q, 16q, 17p, 18q and Xq is found in prostate adenocarcinoma; and Massenkeil et al (1994) *Anticancer Res.* 14(6B), 2785–2790 indicates that LOH was observed at 8p, 17p, 18q in various prostate tumour samples but no deletions were observed on 10q in fourteen informative prostate tumours. Zenklusen et al (1994) *Cancer Res.* 54, 6370–6373 suggests that there is a possible tumour suppressor gene at 7q31.1. In addition, there have been other reports which describe other chromosome loss or abnormalities.

Thus, loss of, or abberations in, most human chromosomes has been implicated in prostate cancer by one research group or another.

A number of tumours exhibit precise loss of the region 10q23-q25 (2, 3), suggesting the presence of a tumour suppressor gene in this area. Mxil, which encodes a negative regulator of the Myc oncoprotein and resides at 10q25, has been proposed as a candidate for the tumour suppressor gene (4); potentially disabling mutations of Mxil in a number of prostate tumours have recently been described. Mxil displays allelic loss and mutation in some cases of prostate cancer and it has been concluded that it may contribute to the pathogenesis or neoplastic evolution of this common malignancy (5).

Objects of the invention are to provide better methods for the diagnosis of cancer and for determining susceptibility to cancer, especially prostate cancer; to provide nucleic acids which are useful in such methods; and to provide a tumour suppressor gene associated with prostate cancer.

SUMMARY OF THE INVENTION

Using fluorescence based allelotyping with highly informative microsatellite CA repeat markers, we have generated a detailed deletion map spanning 10q23-q25, allowing stricter definition of the region of 10q loss likely to be involved in tumour advancement. In addition, we have assessed the frequency of loss and mutation of Mxil in prostate tumours in order to clarify the role of this gene in prostate tamour progression.

Our data indicate the presence of a prostate tumour suppressor gene (or genes) near the 10q23-q24 boundary, which was deleted in the overwhelming majority (22/23) of tumours showing loss. In contrast, specific loss of Mxil, as opposed to loss of other 10q23-q25 regions or of the entire region, was observed in only 1/23 tumours, and was accompanied by loss of markers at the 10q23-q24 boundary.

Furthermore, we failed to detect any mutations in Mxil in those tumours showing Mxil-associated marker loss by either single-strand conformation polymorphism (SSCP) analysis or direct DNA sequencing, and our data indicate that AMril is 20 centiMorgans away from the area of chromosome 10 that we have identified. We have found that all tumours which have a loss of 10q have loss of the region specified below.

A first aspect of the invention provides a nucleic acid capable of selectively hybridising to the region of human chromosome 10 which region is bounded by DNA defined by the markers D10S541 and D10S215 provided that the nucleic acid is not any one of the yeast artificial chromosomes (YACs) 746-H-8, 821-D-2, 831-E-5, 921-F-8, 738-B-12, 796-D-5, 829-E-1, 678-F-1, 839-B-1, 734-B-4, 7B-F12, 757-D-8, 773-C2, 787-D-7, 831-E-9, 855-D-2, 855-G-4, 876-G-11, 894-H-5, 922-E-6, 934-D-3, 964-A-8, 968-E-6 or 24G-A10 and is not any one of the expressed sequence tags (ESTs) as described in Tables 3 to 22, and is not any one of the bacterial artificial chromosomes (BACs) or P1-derived artificial chromosomes (PACs) B2F20, P40F10, P72G8, P74N2, P274D21, B76I10, B79A19, B7901, B93F12, B122L22, P201J8, P201P5, P209K3, P316N14, B46B12, B60C5, B145C22, B150K4, B150N3, B181F15, and 188L22.

It is also preferred if the nucleic acid is not any one of the expressed sequence tags (ESTs) as described in Tables 23 to 37.

The position of various markers on human chromosome 10, including D10S541 and D10S215 (541 and 215, respectively), is as defined in FIG. 5. When we refer to these ESTs we mean the sequence that is disclosed in the referenced Tables, and more particularly the specific cDNA clones from which the sequence is derived.

By "selectively hybridising" we mean that the nucleic acid has sufficient nucleotide sequence similarity with the said chromosome 10 DNA that it can hybridise under moderately or highly stringent conditions. As is well known in the art, the stringency of nucleic acid hybridization depends on factors such as length of nucleic acid over which hybridisation occurs, degree of identity of the hybridizing sequences and on factors such as temperature, ionic strength and CG or AT content of the sequence.

Nucleic acids which can selectively hybridise to the said chromosome 10 DNA include nucleic acids which have >95% sequence identity, preferably those with >98%, more preferably those with >99% sequence identity, over at least a portion of the nucleic acid with the said chromosome 10 DNA. As is well known, human genes usually contain introns such that, for example, a MRNA or cDNA derived from a gene within the said chromosome 10 DNA would not match perfectly along its entire length with the said chromosome 10 DNA but would nevertheless be a nucleic acid capable of selectively hybridising to the said region of chromosome 10.

Typical moderately or highly stringent hybridisation conditions which lead to selective hybridisation are known in the art, for example those described in *Molecular Cloning, a laboratory manual*, 2nd edition, Sambrook et al (eds), Cold Spring Harbor Laboratory Press, Cold Spring Harbor, N.Y., USA.

An example of a typical hybridisation solution when a nucleic acid is immobilised on a nylon membrane and the probe nucleic acid is >500 bases or base pairs is:

6×SSC (saline sodium citrate)

0.5% sodium dodecyl sulphate (SDS)

100 μg/ml denatured, fragmented salmon sperm DNA

The hybridisation is performed at 68° C. The nylon membrane, with the nucleic acid immobilised, may be washed at 68% in 1×SSC or, for high stringency, 0.1×SSC.

20×SSC may be prepared in the following way. Dissolve 175.3 g of NaCl and 88.2 g of sodium citrate in 800 ml of H$_2$O. Adjust the pH to 7.0 with a few drops of a 10 N solution of NaOH. Adjust the volume to 1 litre with H$_2$O. Dispense into aliquots. Sterilize by autoclaving.

An example of a typical hybridisation solution when a nucleic acid is immobilised on a nylon membrane and the probe is an oligonucleotide of between 15 and 50 bases is:

3.0 M trimethylammonium chloride (TMACl)

0.01 M sodium phosphate (pH 6.8)

1 mm EDTA (pH 7.6)

0.5% SDS

100 μg/ml denatured, fragmented salmon sperm DNA 0.1% nonfat dried milk

The optimal temperature for hybridization is usually chosen to be 5° C. below the $T_i$ for the given chain length. $T_i$ is the irreversible melting temperature of the hybrid formed between the probe and its target sequence. Jacobs et al (1988) *Nucl. Acids Res.* 16, 4637 discusses the determination of $T_i$s. The recommended hybridization temperature for 17-mers in 3 M TMACl is 48–50° C.; for 19-mers, it is 55–57° C.; and for 20-mers, it is 58–66° C.

By "nucleic acid capable of selectively hybridising" we also include nucleic acids which will amplify DNA from the said region of chromosome 10 by any of the well known amplification systems such as those described in more detail below, in particular the polymerase chain reaction (PCR). Suitable conditions for PCR amplification include amplification in a suitable 1×amplification buffer:

10×amplification buffer is 500 mM KCl; 100 mM Tris.Cl (pH 8.3 at room temperature); 15 mM MgCl$_2$; 0.1% gelatin.

Suitably, the annealing part of the amplification is between 37° C. and 60° C., preferably 50° C.

The markers D10S541 and DS10S215 define regions on chromosome 10 which are indicated, for example, on the 1993–1994 Genethon human genetic linkage map which is described by Gyapay et al (1994) *Nature Genetics* 7, special issue No. 2, 246–339.

The aforementioned YACs are all publicly available from the CEPH mega-YAC library or the ICI YAC library (7B-F12 and 24G-A10), or from the Human Genome Mapping Project Resource Centre, Hinxton Hall, Hinxton, Cambridgeshire, CB10 1RQ, UK. YAC clone 821D2 has been deposited Sep. 17, 1998, under conditions of the Budapest Treaty with NCIMB, Ltd., 23 St. Machar Drive, Aberdeen, AH24 3RY, Scotland and given Accession No. NCIMB 40973. The position of the YACs on the genetic linkage map is made by reference to the CEPH-Genethon Quickmap database (Cohen et al (1993) *Nature* 366, 698–701). Sequences of the aforementioned expressed sequence tags (ESTs) are given in Tables 3 to 22 and these are publicly available from GenBank, National Center for Biotechnology Information, National Library of Medicine, Bldg 38A, National Institutes of Health, Rockville Pike, Bethesda, Md. 20894, USA. Similarly, sequences of the aforementioned ESTs given in Tables 23 to 37 are publicly available. As is described in more detail below, an especially preferred nucleic acid of the invention is a nucleic acid capable of hybridising to the gene corresponding to the cDNA insert of clone IMAGE 264611.

IMAGE clone 264611 is publicly available from Research Genetics, Inc (2130 Memorial Parkway, SW Huntsville, Ala. 35801, USA) and other IMAGE sources eg American Type Culture Collection, 10810 University Boulevard, Manassas, Va. 20110-2209, USA; Genome Systems Inc, 8629 Pennell Drive, St Louis, Mo., MO 63114, USA, UK-HGMP Resource Centre, Hinxton, Cambridge CB10 1SB. The clone was obtained as described in the enclosed information for the ESTs N29304 and N20238 (see Tables 9 and 10). The clone is in a modified Pharmacia pT7T3 vector.

NAME: pT7T3D-Pac (ampicillin resistant; 50 μg/ml)

HOST: DH10B

V_TYPE: plasmid

POLYLINKER SEQUENCE: (modified)(SEQ ID NO: 21)

tttaatacgactcactatagggaatttg-gccctcgaggccaagaattcccgactacgtag tcggggatccgtcttaattaagcggccg-caagcttattccctttagtgagggtaatttt agcttggcactggccgtcgtta-caacgtcgtgactgggaaaaccctggcgttacccaa cttaatcgccttgcagcacatcccctcgccagctggcgtaatagcgaagag The sequence of the insert of IMAGE clone 264611 is given in FIG. 6.

The following clones contain sequence that is part of the same gene as IMAGE clone 264611 since they overlap to form a largely contiguous sequence. All clones are freely available as physical entities unless otherwise noted. For each clone, some sequence, usually from the 5' or 3' ends, is available as ESTs which can be used to produce probes as described below.

The clones and their ESTs are listed on GenBank and the EMBL databases.

| EST | cDNA clone | Table No |
|---|---|---|
| AA009519 | IMAGE 365465 (5') | 3 (SEQ ID NO: 22) |
| AA009520 | IMAGE 365465 (3') | 4 (SEQ ID NO: 23) |
| AA017563 | IMAGE 361374 (3') | 5 (SEQ ID NO: 24) |
| C01084 | — | 6 (SEQ ID NO: 25) |
| H92038 | IMAGE 221326 (5') | 7 (SEQ ID NO: 26) |
| H92039 | IMAGE 221326 (3') | 8 (SEQ ID NO: 27) |
| N20238 | IMAGE 264611 (3') | 9 (SEQ ID NO: 28) |
| N29304 | IMAGE 264611 (5') | 10 (SEQ ID NO: 29) |
| N35389 | IMAGE 272092 (3') | 11 (SEQ ID NO: 30) |
| N48030 | IMAGE 272092 (5') | 12 (SEQ ID NO: 31) |
| R06763 | IMAGE 126556 (3') | 13 (SEQ ID NO: 32) |
| R06814 | IMAGE 126556 (5') | 14 (SEQ ID NO: 33) |
| R29457 | F1-578D (5') | 15 (SEQ ID NO: 34) |
| T05157 | HFBCS42 | 16 (SEQ ID NO: 35) |
| T60214 | IMAGE 81420 (5') | 17 (SEQ ID NO: 36) |
| W23656 | IMAGE 306632 | 18 (SEQ ID NO: 37) |
| W27533 | — | 19 (SEQ ID NO: 38) |
| W30684 | IMAGE 309597 (5') | 20 (SEQ ID NO: 39) |
| W81026 | IMAGE 347316 (5') | 21 (SEQ ID NO: 40) |
| W81062 | IMAGE 347316 (3') | 22 (SEQ ID NO: 41) |
| AA039223 | IMAGE 486093 (5') | 23 (SEQ ID NO: 42) |
| C17744 | 552A05 | 24 (SEQ ID NO: 43) |
| W37864 | IMAGE 322160 (3') | 25 (SEQ ID NO: 44) |
| W37855 | IMAGE 322160 (5') | 26 (SEQ ID NO: 45) |
| M78282 | HFBBA34 | 27 (SEQ ID NO: 46) |
| N98421 | IMAGE 309597 (3') | 28 (SEQ ID NO: 47) |
| AA017584 | IMAGE 361374 (3') | 29 (SEQ ID NO: 48) |
| AA017563 | IMAGE 361374 (3') | 30 (SEQ ID NO: 49) |
| H84024 | IMAGE 249810 (5') | 31 (SEQ ID NO: 50) |
| T60154 | IMAGE 81420 (3') | 32 (SEQ ID NO: 51) |
| T60214 | IMAGE 81420 (5') | 33 (SEQ ID NO: 52) |
| R29457 | F1-578D (5') | 34 (SEQ ID NO: 53) |
| C01610 | — | 35 (SEQ ID NO: 54) |
| AA001098 | IMAGE 362171 (5') | 36 (SEQ ID NO: 55) |
| R58391 | G3334 (5') | 37 (SEQ ID NO: 56) |

Further information on certan of these clones is given in the following Table 38.

| EST | Match to gene | Clone | Date of Publication | Species |
|---|---|---|---|---|
| • W37864 | 3' UTR | 322160 3' | 11 May 1996 | human |
| • W37855 | 3' UTR | 322160 5' | 15 May 1996 | human |
| • M78282 | 3' UTR | HFBBA34 | 26 May 1992 | human |
| • N98421 | 3' UTR | 309597 3' | 20 Aug 1996 | human |
| • H84024 | 3' UTR | 249810 5' | 13 Nov 1995 | human |
| • AA017584 | 3' UTR, 3152–2963 | 361374 5' | 02 Aug 1996 | human |
| • AA017563 | 5' UTR, 566–782 | 361374 3' | 02 Aug 1996 | human |
| • T60154 | 3' UTR, 3152–2900 | 81420 3' | 09 Feb 1995 | human |
| • T60214 | exon 8, 9 | 81420 5' | 09 Feb 1995 | human |
| • R29457 | 5' UTR v. close to start | F1-578D 5' | 25 April 1995 | human |
| • C01610 | 3' UTR | HUMGS-0008618 | 11 Jul 1996 | human |
| • AA001098 | 3' UTR, no end | 362171 5' | 18 Jul 1996 | human |
| • R58391 | exon 8, 9, 3' UTR | G3334 5' | 02 May 1996 | human |

It is preferred if the nucleic acid is capable of selectively hybridising to the region of chromosome 10 bounded by DNA defined by the markers D10S541 and AFM337xf9. Information on the marker AFM337xf9 is freely available from Genethon, 1 rue de L'Internationale, 91000 Evry, France. AFM337xf9 is now known as D10S1765.

It is particularly preferred if the nucleic acid is capable of selectively hybridising to the human-derived DNA of any one of the YACs 746-H-8, 821-D-2, 831-E-5, 921-F-8, 796-D-5, 829-E-1, 839-B-1, 734-B-4 or 24G-A10; and it is still more preferred if the nucleic acid is capable of selectively hybridising to the human-derived DNA of any one of the YACs 746-H-8, 921-F-8, 821-D-2, 831-E-5, 796-D-5, 24G-A-10 or 734-B-4. It will be appreciated that a YAC contains DNA which is required for propagation and maintenance in yeast. The preferred nucleic acids of the invention are those that selectively hybridise to the human-derived DNA present in the YAC and not other DNA in the YAC, such as yeast DNA.

The human-derived cDNA insert of IMAGE clone 264611 hybridises to at least YAC clones 921F8, 746H8, 821D2, 831E5, 796D5 and 24GA10.

The human-derived cDNA insert of IMAGE clone 264611 hybridises to at least BAC (bacterial artificial chromosome) clones B2F20, B46B12, B60C5, B150K4, B150N3, B145C22, B181F15, and B188L22, but not to B76I10, B79A19, B7901, B93F12 and B122L22.

BAC clones are publicly available from Research Genetics, 2130 Memorial Parkway, SW Huntsville, Ala. 35801, USA and Genome Systems Inc, 8629 Pennell Drive, St Louis; Mo., MO 63114, USA.

The human-derived cDNA insert of IMAGE clone 264611 hybridises to at least PAC (Pl-derived artificial chromosome) clones P40F10 and P274D21, but not to P72G8, P74N2, P201J8 , P201P5, P209K3 and P16N14.

The PAC clones are publicly available from the Sanger Centre, Wellcome Trust Genome Campus, Hinxton, Cambridge CB10 1SA, UK.

Although the nucleic acid of the invention may be RNA or DNA, DNA is preferred. Although the nucleic acid of the invention may be double-stranded or single-stranded, single-stranded nucleic acid is preferred.

The nucleic acid of the invention may be very large, such as 100 kb, if it is double stranded. Indeed genes, such as a tumour suppressor gene, are often this large. However, for diagnostic, probing or amplifying purposes, it is preferred if the nucleic acid has fewer than 10 000, more preferably fewer than 1000, more preferably still from 10 to 100, and in further preference from 15 to 30 base pairs (if the nucleic acid is double-stranded) or bases (if the nucleic acid is single stranded). As is described more fully below, single-stranded DNA primers, suitable for use in a polymerase chain reaction, are particularly preferred.

An especially preferred nucleic acid of the invention is a nucleic acid capable of hybridising to the gene corresponding to the cDNA insert of clone IMAGE 264611 from which EST sequences N29304 and N20238 are derived. The sequence and information for N48030 and N20238 are recorded in the GenBank and EMBL databases (see Tables 9 and 12). Fragments and variants of this gene, and cDNAs derivable from the mRNA encoded by the gene are also preferred nucleic acids of the invention. By "gene corresponding to the cDNA insert clone IMAGE 264611" we mean the gene which encodes MRNA which, when copied in part, produced the cDNA insert in said clone.

Clearly the gene itself and variants and fragments thereof are a preferred nucleic acid of the invention. By "gene" we include not only the introns and exons but also regulatory regions associated with, and physically close to, the introns and exons, particularly those 5' to the 5'-most exon.

By "fragment" of a gene we include any portion of the gene of at least 15 nucleotides in length (whether single stranded or double stranded) but more preferably the fragment is at least 20 nucleotides in length, most preferably at least 50 nucleotides in length and may be at least 100 nucleotides in length or may be at least 500 nucleotides in length. Preferably the fragment is no more than 50 kb and, more preferably, no more than 100 kb.

By "variant" of a gene we include specifically a cDNA, whether partial or full length, or whether copied from any splice variants of mRNA. We also include specifically a nucleic acid wherein, compared to the natural gene, nucleotide substitutions (including inversions), insertions and deletions are present whether in the gene or a fragment thereof or in a cDNA. Both variants and fragments will be selected according to their intended purposes; for probing, amplifying or diagnostic purposes, shorter fragments but a greater degree of sequence identity (eg at least 80%, 90%, 95% or 99%) will generally be required than for the purposes of expressing a therapeutically useful product, where longer fragments will generally be needed but advantage can be taken of the redundancy in the genetic code, if desired.

It is particularly preferred if the nucleic acid of the invention is an oligonucleotide primer which can be used to amplify a portion of the gene corresponding to the cDNA insert of clone IMAGE 264611.

It is also preferred if the nucleic acid of the invention comprises all or part of the gene and can be used as a probe for hybridisation.

The gene and further cDNAs derivable from the gene are readily obtained using methods well known in the art. For example, further cDNAs can be isolated from a prostate cDNA library using standard methods and the IMAGE 264611 clone as a probe or other probes readily derived from the sequences given in Tables 3 to 37 and the Figures. The sequence is readily determined using standard methods. Similarly, the gene can be isolated from a human genomic DNA library, using the IMAGE 264611 clone as a probe using standard methods or other probes readily derived from the sequences in Tables 3 to 37 and the Figures.

A prostate cDNA library may be obtained using standard molecular biology methods or may be obtained from Clontech Laboratories, Inc, 1020 East Meadow Circle, Palo Alto, Calif. 94303-4230, USA.

Standard methods of screening DNA libraries, isolating and manipulating cloned DNA and sequencing DNA are described in Sambrook et al (1989) "Molecular cloning, a laboratory manual", 2nd Edition, Ed Sambrook et al, Cold Spring Harbor Press, Cold Spring Harbor, N.Y.

The predicted amino acid sequence encoded by the IMAGE clone 264611 or the nucleotide sequences shown in Tables 3 to 22 or 23 to 37 may be used to make peptides which can, in turn, be used to make antibodies. The antibodies can be used to screen a cDNA expression library or can be used to isolate the polypeptide encoded by the gene. Once the polypeptide is isolated its N-terminal sequence can be obtained using methods well known in the art. The amino acid sequence is then used to design an oligonucleotide probe which identifies the 5' coding region of a cDNA.

It will be appreciated that the 5' ends of cDNAs can be isolated by RACE (Rapid Amplification of cDNA Ends; Schaefer (1995) *Anal. Biochem.* 227, 255–273), a technique well known in the art. This approach, and related approaches, involve reverse transcription from MRNA using a primer based on the presently known 5' sequence which works back towards the 5' end of the mRNA transcript followed by PCR using random primers to prime from the "unknown" 5' end. Messenger RNA-based RACE can also be used for obtaining 5' ends by isolating MnRNA, removing the 5' cap and then the 5' end is ligated to an adaptor sequence and PCR follows using one primer against the adaptor and one primer specific to the cDNA of interest.

Methods for isolating genes and parts of genes are described in *Current Protocols in Human Genetics,* 1996, Dracopoli et al (ed), John Wiley & Sons, incorporated herein by reference. One useful technique is "vectorette" PCR.

Vectorette PCR can be used for the identification of novel genes, or for the identification of additional sequence when part of the sequence of a gene is already known. The vectorette itself is a double stranded piece of synthetic DNA, with a mismatched central region and one end suitable for ligation to DNA cut by a restriction enzyme (described in *Current Protocols in Human Genetics* 1995 (see pages 5.9.15–5.9.21) and in Valdes et al (1994) *Proc. Natl. Acad. Sci. USA* 91, 5377–5381 and Allen et al *PCR Methods and Applications* 4, 71–75). Following ligation of the vectorette to restriction fragments derived from an appropriate DNA source (usually a large genomic DNA fragment such as a YAC clone), PCR amplification is performed using a primer derived from the target DNA in conjunction with a primer derived from the mismatched region of the vectorette. This vectorette primer has the same sequence as the bottom strand of this mismatched region and therefore has no complementary sequence to anneal to in the first cycle of PCR. The first round of amplification is unidirectional, as priming can only occur from the primer within the target DNA. This produces a complementary strand for the vectorette PCR primer to anneal to in the second PCR cycle. In the second and subsequent cycles of PCR, both primers can prime DNA synthesis with the end result being that the only fragment amplified contains the sequence of interest.

This technique can be used for the identification of intronic sequences within a gene based on a knowledge of the cDNA sequence for that gene. Following restriction digestion of a genomic DNA fragment bearing the gene of interest (such as a YAC clone) and subsequent ligation to the vectorette, a primer designed from the cDNA sequence is used in conjunction with the vectorette primer to PCR amplify a specific fragment of the gene. Exon/intron boundaries can be identified by comparison of the sequence of this fragment to that of the cDNA. This method has been used in combination with primers derived from cDNA clone 264611 to identify intron sequences (see FIGS. 8–15).

Similarly, a vectorette approach can be used to identify the missing 5' end of a gene by using a primer derived from the 5' end of the known cDNA sequence to generate further 5' sequence data.

Vectorettes can also be used for the identification of completely novel gene sequences in a technique known as 'island rescue'. This approach exploits the fact that CpG-rich 'islands' exist within mammalian genomes and that such islands are associated with the 5' ends of genes. Certain restriction enzymes cut within CpG islands, for example, the enzyme NotI. Following NotI digestion of a genomic DNA fragment, a vectorette with a NotI-compatible sticky end is ligated to the resulting subfragments. PCR amplification is then performed using the vectorette primer in conjunction with a primer derived from an Alu repeat element. Such elements occur at frequent intervals in the human genome, therefore it is likely that one or more will lie adjacent to the CpG island of interest and facilitate the generation of a PCR product. As a control, a second PCR reaction is executed, excluding the vectorette primer. Any fragments generated in the Alu/vectorette primed reaction but absent from the Alu only control should represent part of the CpG island and can be gel-purified and analysed for coding sequences using standard methods.

The polypeptide encoded by the gene corresponding to the cDNA clone IMAGE 264611 or the nucleotide sequences shown in Tables 3 to 22 or 23 to 37 has some sequence similarity to the polypeptide tensin, a protein involved in cytoskeletal/extracellular matrix interactions; similarity is also observed, at least at the nucleotide sequence level, with auxilin, a protein involved in protein transport to the cell membrane via clathrin coated vesicles. Sequence similarity between tensin and auxilin has also been noted previously.

A preferred nucleic acid of the invention is one comprising a tamour suppressor gene or fragment or variant thereof. The tumour suppressor gene is one which is involved in the origin or development of a cancer such as prostate cancer, melanoma, glioma or non-Hodgkin's lymphoma. Suitably, the tumour suppressor is involved in the origin or development of prostate cancer, particularly prostate adenocarcinoma.

A nucleic acid of the invention comprising a tumour suppressor gene or fragment or derivative thereof is readily identified; for example, the gene may be identified by screening a panel of RNAs from prostate and other tumour cell lines in order to identify a reduced level of transcript. The transcript may be large, as it will probably have a complex function and several sites for disabling mutation 'hits' (as is the case with the tumour suppressor genes BRCA1, RB). Cross-species conservation indicates that the gene has a basic cell 'housekeeping' function, the loss of which may lead to loss of growth control and tumour formation.

By "tumour suppressor gene" we include any gene for which loss or some reduction in any of its function or activities can contribute to neoplasia.

Analysis of the entire coding region of the tumour suppressor gene in tumours indicates that the gene is a tumour suppressor gene when the gene has been altered compared to the gene in non-tumour tissue or to the gene in an individual who does not have, and who is not prone to, prostate cancer, and that it is involved in the cancer, such as prostate cancer. Suitable methods for mutation analysis include single-stranded conformation polymorphism (SSCP) analysis (or variations of this technique) and direct DNA sequencing. These are well known to the person skilled in the art, and SSCP, for example, is described in *Current Protocols in Human Genetics*, 1995, pp 7.4.1–7.4.6.

Any tumour suppressor gene of the invention almost certainly contains introns (as does the gene corresponding to IMAGE clone 264611) and almost certainly is >0.5 kb, more likely >1.0 kb and most likely between 1.0 kb and 500 kb. The cDNA insert in IMAGE clone 264611 is about 1.7 kbp. Any tumour suppressor gene of the invention almost certainly is polymorphic in its DNA sequence. Thus, fragments (such as restriction fragments or fragments derived by enzymatic amplification) and variants (such as natural variats, eg allelic variants) or variants created by in vitro manipulation are part of the invention. Suitable such fragments include fragments which are useful as a hybridisation probe or fragments which are useful as an amplification primer. Suitable such variants include variants in which the coding sense of the gene is unaltered or variants in which the coding sequence is modified so as to alter the properties of the encoded polypeptide.

Although any tumour suppressor gene of the invention almost certainly ultimately encodes a polypeptide, it may encode an RNA species which RNA species does not encode a polypeptide.

It is further preferred if the nucleic acid comprises a nucleic acid productof a tumour suppressor gene or derivative or fragment or variant thereof. Such nucleic acids include mRNA transcribed from the tumour suppressor gene.

It is particularly preferred if the nucleic acid is a cDNA (copy DNA) derived from a mRNA transcribed from the tumour suppressor gene. Libraries of cDNA derived from selected tissues, such as prostate or prostate tumour tissue, are known in the art and can be prepared from suitable MRNA using methods known in the art for example as described in *Molecular cloning, a laboratory manual* (supra).

The nucleotide sequences described in Tables 3 to 22 or 23 to 37 are partial sequences of partial cDNAs the said cDNAs being derived from mRNAs which are related to, selectively hybridise to, and are almost certainly transcribed from a gene or genes found in the region of human chromosome 10 which region is bounded by DNA defined by the markers D10S541 and D10S215. The mncleotide sequences shown in FIGS. 8 to 15 and 16 to 24 include sequences from introns in the gene corresponding to IMAGE clone 264611. More particularly, we have found that polynucleotides comprising the sequences of any of Tables 3 to 22 or 23 to 37 and FIGS. 6 and 8 to 15 and 16 to 24 hybridise to at least one of the aforementioned YAC, BAC and PAC clones. Thus, the nucleotide sequences of Tables 3 to 22 and 23 to 37 and FIG. 6 represent the MRNA products of at least one gene which is found within the region of human chromosome 10 which region is bounded by DNA defined by the markers D10S541 and D10S215; more particularly in the sub-region A defined by the YAC clones. A particularly preferred embodiment comprises a nucleic acid capable of selectively hybridising to the region of human chromosome 10 which region is bounded by DNA defined by the markers D10S541 and D10S215 and capable of selectively hybridising to the human-derived sequence as described in any one of Tables 3 to 22 and FIGS. 6 and 8 to 15 provided that the nucleic acid is not any one of the yeast artificial chromosomes (YACs) 746-H-8, 821-D-2, 831-E-5, 921-F-8, 738-B-12, 796-D-5, 829-E-1, 678-F-1, 839-B-1, 734-B-4, 7B-F12, 757-D-8, 773-C-2, 787-D-7, 829-E-1, 831-E-9, 855-D-2, 855-G-4, 876-G-11, 894-H-5, 921-F-8, 922-E-6, 934-D-3, 964-A-8, 968-E-6 or 24G-A10 and is not any one of the polynucleotides as described in Tables 3 to 22 and is not any one of the BACs or PACs B2F20, P40F10, P72G8, P74N2, P274D21, B76I10, B79A19, B7901, B93F12, B122L22, P201J8 , P201P5, P209K3, P316N14, 46B12, B60C5, B145C22, B150K4, B150N3, B181F15, and B188L22.

It will readily be appreciated that a person skilled in the art can identify a gene or genes which correspond to IMAGE clone 264611 by making use of the sequence information presented in Tables 3 to 22 or 23 to 37 and FIGS. 6 and 8 to 15 or 16 to 24.

In particular, it is preferred if the nucleic acid comprises the gene or genes from which the sequence of any one of Tables 3 to 22 or 23 to 37 and FIGS. 6 and 8 to 15 and 16 to 24 is derived or a fragment or variant thereof. It is also preferred if the nucleic acid comprises a full length cDNA or a cDNA which is at least 50% of the length of a mRNA transcript; more preferably greater than 75% of the length; more preferably greater than 95% of the length.

It may be desirable to subclone the nucleic acid, particularly if all or part of the protein coding sequence is to be expressed.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example Aspergillus), plant cells, animal cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps)

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endomiclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

Particularly preferred nucleic acids of the first aspect of the invention are those selected from the group consisting of primers suitable for amplifying nucleic acid. Suitably, the nucleic acids are selected from the group consisting of primers which hybridise to the nucleotide sequences as described in any one of Tables 3 to 22 and FIGS. 6 and 8 to 15, or their complement.

It is particularly preferred if the amplification primers hybridise to the introns of a gene. They are particularly useful if processed pseudogenes are present. Thus, it is preferred if the nucleic acids are selected from the group consisting of primers which hybridise to the sequences given in FIGS. 6 and 8 to 15, or their complement.

Primers which are suitable for use in a polymerase chain reaction (PCR; Saiki et al (1988) *Science* 239, 487–491) are preferred. Suitable PCR primers may have the following properties:

It is well known that the sequence at the 5' end of the oligonucleotide need not match the target sequence to be amplified.

It is usual that the PCR primers do not contain any complementary structures with each other longer than 2 bases, especially at their 3' ends, as this feature may promote the formation of an artifactual product called "primer dimer". When the 3' ends of the two primers hybridize, they form a "primed template" complex, and primer extension results in a short duplex product called "primer dimer".

Internal secondary structure should be avoided in primers. For symmetric PCR, a 40–60% G+C content is often recommended for both primers, with no long stretches of any one base. The classical melting temperature calculations used in conjunction with DNA probe hybridization studies often predict that a given primer should anneal at a specific temperature or that the 72° C. extension temperature will dissociate the primer/template hybrid prematurely. In practice, the hybrids are more effective in the PCR process than generally predicted by simple $T_m$ calculations.

Optimum annealing temperatures may be determined empirically and may be higher than predicted. Taq DNA polymerase does have activity in the 37–55° C. region, so primer extension will occur during the annealing step and the hybrid will be stabilized. The concentrations of the primers are equal in conventional (symmetric) PCR and, typically, within 0.1- to 1-$\mu$M range.

Any of the nucleic acid amplification protocols can be used in the method of the invention including the polymerase chain reaction, QB replicase and ligase chain reaction. Also, NASBA (nucleic acid sequence based amplification), also called 3SR, can be used as described in Compton (1991) *Nature* 350, 91–92 and *AIDS* (1993), Vol 7 (Suppl 2), S108 or SDA (strand displacement amplification) can be used as described in Walker et al (1992) *Nuci. Acids Res.* 20, 1691–1696. The polymerase chain reaction is particularly preferred because of its simplicity.

When a pair of suitable nucleic acids of the invention are used in a PCR it is convenient to detect the product by gel electrophoresis and ethidium bromide staining. As an alternative to detecting the product of DNA amplification using agarose gel electrophoresis and ethidium bromide staining of the DNA, it is convenient to use a labelled oligonucleotide capable of hybridising to the amplified DNA as a probe. When the amplification is by a PCR the oligonucleotide probe hybridises to the interprimer sequence as defined by the two primers. The oligonucleotide probe is preferably between 10 and 50 nucleotides long, more preferably between 15 and 30 nucleotides long. The probe may be labelled with a radionuclide such as $^{32}P$, $^{33}P$ and $^{35}S$ using standard techniques, or may be labelled with a fluorescent dye. When the oligonucleotide probe is fluorescently labelled, the amplified DNA product may be detected in solution (see for example Balaguer et at (1991) "Quantification of DNA sequences obtained by polymerase chain reaction using a bioluminescence adsorbent" *Anal. Biochem.* 195, 105–110 and Dilesare et al (1993) "A high-sensitivity electrochemiluminescence-based detection system for automated PCR product quantitation" *BioTechniques* 15, 152–157.

PCR products can also be detected using a probe which may have a fluorophore-quencher pair or may be attached to a solid support or may have a biotin tag or they may be detected using a combination of a capture probe and a detector probe.

Fluorophorequencher pairs are particularly suited to quantitative measurements of PCR reactions (eg RT-PCR). Fluorescence polarisation using a suitable probe may also be used to detect PCR products.

Further particularly preferred nucleic acids are those which will act as PCR primers which primers can be selected by reference to the sequence shown in FIGS. 6 and 8 to 15. These primers are useful in amplifying DNA derived from the gene corresponding to the cDNA clone IMAGE 264611. These primers include, but are not limited to, the sequences which are given on FIGS. 8 to 15 in bold (see Figure legends). The downstream (3') primers are the reverse complement of the sequences indicated in bold.

Oligonucleotide primers can be synthesised using methods well known in the art, for example using solid-phase phosphoramidite chemistry.

A second aspect of the invention provides a nucleic acid capable of selectively hybridising to the region of human chromosome 10 which region is bounded by DNA defined by the markers D10S541 and D10S215, further comprising a detectable label.

By "detectable label" we include any convenient radioactive label such as $^{32}P$, $^{33}P$ or $^{35}S$ which can readily be incorporated into a nucleic acid molecule using well known methods; we also include any convenient fluorescent or chemiluminescent label which can readily be incorporated into a nucleic acid. In addition the term "detectable label" also includes a moiety which can be detected by virtue of binding to another moiety (such as biotin which can be detected by binding to streptavidin); and a moiety, such as an enzyme, which can be detected by virtue of its ability to convert a colourless compound into a coloured compound, or vice versa (for example, alkaline phosphatase can convert colourless o-nitrophenylphosphate into coloured o-nitrophenol). Conveniently, the nucleic acid probe may occupy a certain position in a fixed assay and whether the nucleic acid hybridises to the said region of human chromosome 10 can be determined by reference to the position of hybridisation in the fixed assay. The detectable label may also be a fluorophore-quencher pair as described in Tyagi & Kramer (1996) *Nature Biotechnology* 14, 303–308.

It is preferred if the nucleic acid comprises the human-derived sequence in any one of the expressed sequence tags (ESTs) as described in Tables 3 to 22 or 23 to 37 or the cDNA described in FIG. 6 or the intron sequences shown in FIGS. 8 to 15 or 16 to 24 further comprising a detectable label; or if the nucleic acid comprises the human-derived sequence in any one of the yeast artificial chromosomes (YACs) 921-F-8, 746-H-8, 821-D-2, 831-E-5, 796-D-5, 24G-A-10 or 734-B-4 or BAC clones B2F20, B46B12, B60C5, B150K4, B150N3, B145C22, B181F15, B188L22, or PAC clones P40F10, and P274D21.

Particularly preferred nucleic acids are those of the first aspect of the invention further comprising a detectable label.

A third aspect of the invention provides a method for determining the susceptibility of a patient to cancer comprising the steps (i) obtaining a sample containing nucleic acid derived from the patient; and (ii) contacting the said nucleic acid with a nucleic acid capable of selectively hybridising to the region of human chromosome 10 which region is bounded by DNA defined by the markers D10S541 and D10S215.

The method is suitable for determining the susceptibility of a patient to any cancer but it is preferred if the cancer for which susceptibility is determined is prostate cancer, melanoma, glioma or non-Hodgkin's lymphoma. The method is most suited for determining the susceptibility of a patient to prostate cancer. Accordingly, at least for the determination of susceptibility to prostate cancer, the patient is male.

The presence or absence of a portion of human chromosome 10 may be determined by the methods of the third, fourth and fifth aspects of the invention, and in a preferred embodiment of the third, fourth and fifth aspects of the invention the nucleic acid capable of selectively hybridising to the said region of human chromosome 10 is a nucleic acid suitable for amplification of a portion of the said region of chromosome 10.

A fourth aspect of the invention provides a method of diagnosing cancer in a patient comprising the steps of (i) obtaining a sample containing nucleic acid derived from the patient; and (ii) contacting the said nucleic acid with a nucleic acid capable of selectively hybridising to the region of human chromosome 10 which region is bounded by DNA defined by the markers D10S541 and D10S215.

The method is particularly suited for distinguishing between neoplasia and hyperplasia of the prostate. Because all tumours which have a loss of 10q have also been found to lack the region specified herein, a differential diagnostic test can be performed, using the markers of the invention and other markers (including markers on other chromosomes).

A fifth aspect of the invention provides a method of predicting the relative prospects of a particular outcome of a cancer in a patient comprising the steps of (i) obtaining a sample containing nucleic acid derived from the patient; and (ii) contacting the said nucleic acid with a nucleic acid capable of selectively hybridising to the region of human chromosome 10 which region is bounded by DNA defined by the markers D10S541 and D10S215.

Although any sample containing nucleic acid derived from the patient is useful in the methods of the third, fourth and fifth aspects of the invention, it is preferred if the sample is selected from the group consisting of prostate tissue, blood, urine or semen. Prostate tissue can be obtained from a patient using standard surgical techniques. Cells derived from the prostate are found in small numbers in the urine and in the blood. Although it is preferred that the sample containing nucleic acid from the patient is, or is derived directly from, a cell of the patient, such as a prostate cell, a sample indirectly derived from a patient, such as a cell grown in culture, is also included within the invention. Equally, although the nucleic acid derived from the patient may have been physically within the patient, it may alternatively have been copied from nucleic acid which was physically within the patient. The tumour tissue may be taken from the primary tumour or from metastases, and particularly may be taken from the margins of the tumour.

Conveniently, the nucleic acid capable of selectively hybridising to the region of human chromosome 10 which region is bounded by DNA defined by the markers D10S541 and D10S215 further comprises a detectable label. The detectable label includes the labels described above in relation to the second aspect of the invention.

It will be appreciated that the aforementioned methods may be used for presymptomatic screening of a patient who is in a risk group for cancer. For example, men older than about 60 years are at greater risk of prostate cancer than men below the age of 35. Similarly, the methods may be used for the pathological classification of tumours such as prostate tumours.

Conveniently, in the methods of the third, fourth and fifth aspects of the invention the nucleic acid which is capable of the said selective hybridisation (whether labelled with a detectable label or not) is contacted with a nucleic acid derived from the patient under hybridising conditions. Suitable hybridising conditions include those described in relation to the first aspect of the invention.

It is preferred that if blood, semen or urine is the source of the said sample containing nucleic acid derived from the patient that the sample is enriched for prostate-derived tissue or cells. Enrichment for prostate cells may be achieved using, for example, cell sorting methods such as fluorescent activated cell sorting (FACS) using a prostate-selective antibody such as one directed to prostate-specific antigen (PSA). The source of the said sample also includes biopsy material and tumour samples, also including fixed paraffin mounted specimens as well as fresh or frozen tissue.

The methods of the third, fourth or fifth aspect of the invention may involve sequencing of DNA at one or more of the relevant positions within the relevant region, including direct sequencing; direct sequencing of PCR-amplified exons; differential hybridisation of an oligonucleotide probe designed to hybridise at the relevant positions within the relevant region (conveniently this uses immobilised oligonucleotide probes in, so-called, "chip" systems which are well known in the art); denaturing gel electrophoresis following digestion with an appropriate restriction enzyme, preferably following amplification of the relevant DNA regions; S1 nuclease sequence analysis; non-denaturing gel electrophoresis, preferably following amplification of the relevant DNA regions; conventional RFLP (restriction fragment length polymorphism) assays; heteroduplex analysis; selective DNA amplification using oligonucleotides; fluorescent in-situ hybridisation of interphase chromosomes; ARMS-PCR (Amplification Refractory Mutation System-PCR) for specific mutations; cleavage at mismatch sites in hybridised nucleic acids (the cleavage being chemical or enzymic); SSCP single strand conformational polymorphism or DGGE (discontinuous or denaturing gradient gel electrophoresis); analysis to detect mismatch in annealed normal/mutant PCR-amplified DNA; and protein truncation assay (translation and transcription of exons—if a mutation introduces a stop codon a truncated protein product will result). Other methods may be employed such as detecting changes in the secondary structure of single-stranded DNA resulting from changes in the primary sequence, for example, using the cleavage I enzyme. This system is commercially available from GibcoBRL, Life Technologies, 3 Fountain Drive, Inchinnan Business Park, Paisley PA4 9RF, Scotland.

Detailed methods of mutation detection are described in "Laboratory Protocols for Mutation Detection" 1996, ed. Landegren, Oxford University Press on behalf of HUGO (Human Genome Organisation).

It is preferred if RFLP is used for the detection of fairly large ($\geq 500$ bp) deletions or insertions. Southern blots may be used for this method of the invention.

PCR amplification of smaller regions (maximum 300 bp) to detect small changes greater than 3–4 bp insertions or deletions may be preferred. Amplified sequence may be analysed on a sequencing gel, and small changes (minimum size 3–4 bp) can be visualised. Suitable primers are designed as herein described.

In addition, using either Southern blot analysis or PCR restriction enzyme variant sites may be detected.

For example, for genomic DNA: restriction enzyme digestion, gel electrophoresis, Southern blotting, and hybridisation specific probe (any of the YACs, BACs, in the region as described herein, or a suitable fragment derived therefrom).

For example for PCR: amplify DNA, restriction enzyme digestion, gel detection by ethidium bromide, silver staining or incorporation of radionucleotide or fluorescent primer in the PCR.

Other suitable methods include the development of allele specific oligonucleotides (ASOs) for specific mutational events. Similar methods are used on RNA and cDNA for prostate specific tissue.

The method also includes checking for loss-of-heterozygosity (LOH; shows one copy lost) and then look for loss of function of RNA by failing to detect a mRNA on Northern blots or by PCR or in RNA/cDNA (shows other copy non-active). LOH on a tumour cell, from whatever source, compared to blood is useful as a diagnostic tool, eg show that the tumour has progressed and requires more stringent treatment.

Preferably, in the third, fourth and fifth aspects of the invention, the nucleic acid is capable of selectively hybridising to the region of human chromosome 10 which region is bounded by the markers D10S541 and D10S215; more preferably the said nucleic acid comprises or is capable of selectively hybridising to the human-derived DNA of any one of YACs 746-H-8, 821-D-2, 831-E-5, 921-F-8, 796-D-5, 829-E-1, 839-B-1, 734-B-4 or 24G-A10; more preferably still the nucleic acid comprises or is capable of selectively hybridising to the humanerived DNA of any one of the YACs 821-D-2, 831-E-5, 796-D-5, 24G-A-10 or 734-B-4.

It is also preferred if the nucleic acid comprises or is capable of selectively hybridising to the human-derived DNA of any of the BACs or PACs B2F20, P40F10, P72G8, P74N2, P274D21, B76I10, B79A19, B7901, B93F12, B122L22, P201J8, P201P5, P209K3, P316N14, B46B12, B60C5, B145C22, B150K4, B150N3, B181F15, and B188L22.

It is also preferred if the nucleic acid is a primer for the microsatellite markers D10S541, D10S215 and AFM337xf9 (D10S1765), namely:

| | |
|---|---|
| 5'-AAGCAAGTGAAGTCTTAGAACCACC-3' | (SEQ ID NO:1) |
| 5'-CCACAAGTAACAGAAAGCCTGTCTC-3' | (SEQ ID NO:2) |
| 5'-TGGCATCATTCTGGGGA-3' | (SEQ ID NO:3) |
| 5'-GCTTTACGTTTCTTCACATGGT-3' | (SEQ ID NO:4) |
| 5'-ACACTTACATAGTGCTTTCTGCG-3' | (SEQ ID NO:5) | and

| | |
|---|---|
| 5'-CAGCCTCCCAAAGTTGC-3' | (SEQ ID NO:6). |

It is particularly preferred if the nucleic acid is capable of selectively hybridising to the gene corresponding to the cDNA insert of the clone IMAGE 264611.

Thus, the present invention provides a use of a nucleic acid which is capable of selectively hybridising to the said region of human chromosome 10 in diagnosing cancer or diagnosing susceptibility to cancer.

Also, the present invention provides a method of determining the presence or absence, or a mutation in, the said region of human chromosome 10.

Preferably, the said nucleic acid capable of selectively hybridising is DNA, and also preferably the said nucleic acid is single-stranded.

It is particularly preferred if the said nucleic acid capable of selectively hybridising has fewer than 10 000 base pairs when the nucleic acid is double-stranded or bases when the nucleic acid is single-stranded; more preferably if the said nucleic acid has fewer than 1000 base pairs when the nucleic acid is double-stranded or bases when the nucleic acid is single-stranded; more preferably still if the said nucleic acid has from 10 to 100 base pairs when the nucleic acid is double-stranded or bases when the nucleic acid is single-stranded; and even more preferably if the said nucleic acid has from 15 to 30 base pairs when the nucleic acid is double-stranded or bases when the nucleic acid is single-stranded.

It is preferred if the said nucleic acid capable of selectively hybridising comprises a tamour suppressor gene or fragment or variant thereof, or a nucleic acid which selectively hybridises thereto.

It is preferred if the said nucleic acid capable of selectively hybridising is suitable as a primer for nucleic acid amplification. Suitable primers include those described in relation to the first and second aspects of the invention.

In a preferred embodiment, reverse transcriptase PCR is used to detect micrometastases in blood samples from the patient. A blood sample is taken and RNA prepared from the nucleated cells in the sample. This is used in PCR amplification with oligonucleotide primers detecting the presence or absence, or mutations in prostate tumour suppressor mRNA. This is a relatively sensitive method that can detect one cell in a mix of more than a million normal cells and it is possible to detect prostate tumour suppressor mRNA products present in circulating metastatic cells mixed with normal blood cells that do not express these genes. The gene products of those genes present in the region of chromosome 10 which region is bounded by DNA defined by the markers D10S541 and D10S215, are useful markers detecting circulating prostate cells.

It will be appreciated that it is also possible to detect micrometastases by looking for mutations in the DNA of cells in the blood sample directly, or by using the protein truncation test or by using microsatellite markers; in this case the suspected tumour cells should be purified from the blood.

It is also preferred if the said nucleic acid capable of selectively hybridising is, or is capable of hybridising to, the human derived sequence as described in Tables 3 to 22 or 23 to 37 or FIGS. 6 and 8 to 15 or 16 to 24; conveniently the said nucleic acid is selected from the group consisting of primers which hybridise to DNA from the sequences as described in Tables 3 to 22 or 23 to 37 or FIGS. 6 and 8 to 15 or 16 to 24.

The methods of the invention include the detection of mutations in the region of chromosome 10 bounded by DNA defined by the markers D10S541 and D10S215; especially in the tumour suppressor gene.

The methods of the invention may make use of a difference in restriction enzyme cleavage sites caused by mutation. A non-denaturing gel may be used to detect differing lengths of fragments resulting from digestion with an appropriate restriction enzyme. The DNA is usually amplified before digestion, for example using the polymerase chain reaction (PCR) method and modifications thereof. Otherwise 10–100 times more DNA would need to be obtained in the first place, and even then the assay would work only if the restriction enzyme cuts DNA infrequently.

Amplification of DNA may be achieved by the established PCR method as disclosed by Saiki et al (1988) *Science* 239, 487–491 or by developments thereof or alternatives such as the ligase chain reaction, QB replicase and nucleic acid sequence-based amplification or other known amplification methods, some of which are described herein.

An "appropriate restriction enzyme" is one which will recognise and cut the wild-type sequence and not the mutated sequence or vice versa. The sequence which is recognised and cut by the restriction enzyme (or not, as the case may be) can be present as a consequence of the mutation or it can be introduced into the normal or mutant allele using mismatched oligonucleotides in the PCR reaction. It is convenient if the enzyme cuts DNA only infrequently, in other words if it recognises a sequence which occurs only rarely.

In another method, a pair of PCR primers are used which match (ie hybridise to) either the wild-type genotype or the mutant genotype but not both. Whether amplified DNA is produced will then indicate the wild-type or mutant genotype (and hence phenotype). However, this method relies partly on a negative result (i.e.the absence of amplified DNA) which could be due to a technical failure. It is therefore less reliable and/or requires additional control experiments.

A preferable method employs similar PCR primers but, as well as hybridising to only one of the wild-type or mutant sequences, they introduce a restriction site which is not otherwise there in either the wild-type or mutant sequences.

The nucleic acids provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the tumour suppressor gene or mRNA using other techniques. Mismatches can be detected using either enzymes (e.g. S1 nuclease or resolvase), chemicals (e.g. hydroxylamine or osmium tetroxide and piperidine), or changes in electrophoretic mobility of mismatched hybrids as compared to totally matched hybrids. These techniques are known in the art. Generally, the probes are complementary to the tumour suppressor gene coding sequences, although probes to certain introns are also contemplated. An entire battery of nucleic acid probes may be used to compose a kit for detecting loss of or mutation in wild-type tumour suppressor genes. The kit allows for hybridization to the entire tumour suppressor gene. The probes may overlap with each other or be contiguous.

If a riboprobe is used to detect mismatches with mRNA, it is complementary to the mRNA of the human wild-type tumour suppressor gene. The riboprobe thus is an anti-sense probe in that it does not code for the protein encoded by the tumour suppressor gene because it is of the opposite polarity to the sense strand. The riboprobe generally will be labelled, for example, radioactively labelled which can be accomplished by any means known in the art. If the nboprobe is used to detect mismatches with DNA it can be of either polarity, sense or anti-sense. Similarly, DNA probes also may be used to detect mismatches.

Nucleic acid probes may also be complementary to mutant alleles of the tumour suppressor gene. These are useful to detect similar mutations in other patients on the basis of hybridization rather than mismatches. As mentioned above, the tumour suppressor gene probes can also be used in Southern hybridizations to genomic DNA to detect gross chromosomal changes such as deletions and insertions. The probes can also be used to select cDNA clones of tumour suppressor genes from tumour and normal tissues. In addition, the probes can be used to detect tumour suppressor gene mRNA in tissue to determine if expression is altered, for example diminished, as a result of loss of wild-type tumour suppressor genes.

According to the diagnostic and prognostic method of the present invention, loss of the wild-type gene is detected. The loss may be due to either insertional, deletional or point mutational events. If only a single allele is mutated, an early neoplastic state may be indicated. However, if both alleles are mutated then a malignant state is indicated or an increased probability of malignancy is indicated. The finding of such mutations thus provides both diagnostic and prognostic information. A tumour suppressor gene allele which is not deleted (e.g. that on the sister chromosome to a chromosome carrying a gene deletion) can be screened for other mutations, such as insertions, small deletions, and point mutations. It is believed that most mutations found in tumour tissues will be those leading to greatly altered expression of the tumour suppressor gene product. However, mutations leading to non-functional gene products would also lead to a malignant state or an increased probability of malignancy. Mutational events (such as point mutations, deletions, insertions and the like) may occur in regulatory regions, such as in the promoter of the gene, leading to loss or diminution of expression of the mRNA. Point mutations may also abolish proper RNA processing, leading to loss of expression of the tumour suppressor gene product.

The invention also includes the following methods: in vitro transcription and translation of tumour suppressor gene to identify truncated gene products, or altered properties such as substrate binding; immunohistochemistry of tissue sections to identify cells in which expression of the protein is reduced/lost, or its distribution is altered within cells or on their surface; and the use of RT-PCR using random primers, prior to detection of mutations in the region as described above.

A sixth aspect of the invention provides a system (or it could also be termed a kit of parts) for detecting the presence or absence of, or mutation in, the region of human chromosome 10 which region is bounded by DNA defined by the markers D10S541 and D10S215, the system comprising a nucleic acid capable of selectively hybridising to the region of human chromosome 10 which region is bounded by DNA defined by the markers D10S541 and D10S215 and a nucleoside triphosphate or deoxynucleoside triphosphate or derivative thereof. Preferred nucleic acids capable of selectively hybridising to the region of human chromosome 10 which region is bounded by DNA defined by markers D10S541 and D10S215 are the same as those preferred in the third, fourth and fifth aspects of the invention.

By "mutation" we include insertions, substitutions and deletions.

By "nucleoside triphosphate or deoxynucleoside triphosphate or derivative thereof" we include any naturally occurring nucleoside triphosphate or deoxynucleoside triophosphate such as ATP, GTP, CTP, and UTP, dATP dGTP, dCTP, TTP as well as non-naturally derivatives such as those that include a phosphorothioate linkage (for example αS derivatives).

Conveniently the nucleoside triphosphate or deoxynucleoside triphosphosphate is radioactively labelled or derivative thereof, for example with $^{32}P$, $^{33}P$ or $^{35}S$, or is fluorescently labelled or labelled with a chemiluminescence compound or with digoxygenin.

Conveniently deoxynucleotides are at a concentration suitable for dilution to use in a PCR.

Thus, the invention includes a kit of parts which includes a nucleic acid capable of selectively hybridising to the said region of human chromosome 10 and means for detecting the presence or absence of, or a mutation in, the said region.

A seventh aspect of the invention provides a system for detecting the presence or absence of, or mutation in, the region of human chromosome 10 which region is bounded by DNA defined by the markers D10S541 and D10S215, the system comprising a nucleic acid capable of selectively hybridising to the region of human chromosome 10 which region is bounded by DNA defined by the markers D10S541 and D10S215 and a nucleic acid modifying enzyme. Preferred nucleic acids capable of selectively hybridising to the region of human chromosome 10 which region is bounded by DNA defined by markers D10S541 and D10S215 are the same as those preferred in the third, fourth and fifth aspects of the invention.

By "mutation" we include insertions, substitutions (including transversions) and deletions.

By "nucleic acid modifying enzyme" we include any enzyme capable of modifying an RNA or DNA molecule. Preferred enzymes are selected from the group consisting of DNA polymerases, DNA ligases, polynucleotide kinases or restriction endonucleases. A particularly preferred enzyme is a thermostable DNA polymerase such as Taq DNA polymerase. Nucleases such as Cleavase I which recognise secondary structure, for example mismatches, may also be useful.

An eighth aspect of the invention provides a polypeptide capable of being encoded by the tumour suppressor gene of the invention or a fragment or variant thereof. The polypeptide preferably has tumour suppressor activity, especially in the prostate, or cross-reacts with an antibody which is specific for the native polypeptide.

A ninth aspect of the invention comprises a molecule capable of specifically binding with a polypeptide of the eighth aspect of the invention. Suitably, the molecule is an antibody-like molecule comprising complementarity-determining regions specific for the said polypeptide.

Monoclonal antibodies which will bind to many of these antigens are already known but in any case, with today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982).

Chimaeric antibodies are discussed by Neuberger et al (1988, 8th *International Biotechnology Symposium* Part 2, 792–799).

Suitably prepared non-human antibodies can be "humanized" in known ways, for example by inserting the CDR regions of mouse antibodies into the framework of human antibodies.

Further aspects of the invention provide methods (a) for determining the susceptibility of a patient to cancer comprising the steps of (i) obtaining a sample containing protein derived from the patient; and (ii) determining the relative amount or size in the said sample of the polypeptide according to the eighth aspect of the invention or determining whether there is a truncation of, or loss of function of, a polypeptide according to the eighth aspect of the invention; (b) of diagnosing cancer in a patient comprising the steps of (i) obtaining a sample containing protein derived from the patient; and (ii) determining the relative amount or size in the said sample of the polypeptide according to the eighth aspect of the invention; and (c) of predicting the relative prospects of a particular outcome of a cancer in a patient comprising the steps of (i) obtaining a sample containing protein derived from the patient; and (ii) determining the relative amount in the said sample of the polypeptide according to the seventh aspect of the invention.

Typically, compared to a normal cell, the protein in the cancer cell is truncated or the amount of protein product is decreased.

By "derived from the patient" we include a sample directly derived from the patient or indirectly derived from, for example the protein may be produced from isolated DNA from the patient by in vitro transcription and translation. The sample may be any suitable sample and includes biopsy material, tumour samples (for example, those on fixed paraffin mounts and fresh and frozen tissue) and cells shed from tumour samples.

These methods are suited to determining the susceptibility of a patient to any cancer but are particularly suited to prostate cancer, melanoma, glioma or non-Hodgkin's lymphoma. Accordingly, at least for the determination of susceptibility to prostate cancer, the patient is male. Prostate cancer is particularly relevant.

Conveniently, the said polypeptide is detected using a molecule as defined in the ninth aspect of the invention. Preferably, the molecule is an antibody-like molecule comprising complementarity-determining regions specific for the polypeptide. Suitably, the molecule, such as a monoclonal antibody, comprises a detectable label. Suitable detectable labels include radioactive labels such as $^{125}$I and $^{131}$I and other radionuclides such as those used in diagnostic imaging, as well as any convenient fluorescent or chemiluminescent label which can readily be incorporated into the molecule, such as an antibody. In addition the term "detectable label" also includes a moiety which can be detected by virtue of binding to another moiety (such as biotin which can be detected by binding to streptavidin); and a moiety, such as an enzyme, which can be detected by virtue of its ability to convert a colourless compound into a coloured compound, or vice versa (for example, alkaline phosphalase can convert colourless o-nitrophenylphosphate into coloured o-nitrophenol).

Conveniently, the antibodies are raised to peptides encoded by different exons of the said polypeptide. These can be used to detect truncated proteins, for example in tissue sections, as well as in protein truncation assays, and can also be used to detect changes in the level of proteins.

A further aspect of the invention provides the use of a nucleic acid capable of selectively hybridising to the region of human chromosome 10 which region is bounded by DNA defined by the markers D10S541 and D10S215 in the manufacture of a reagent for diagnosing cancer, especially prostate cancer; and in the manufacture of a medicament for treating cancer.

A still further aspect of the invention provides a method of treating cancer comprising the step of administering to the patient a nucleic acid capable of selectively hybridising to the region of human chromosome 10 which region is bounded by DNA defined by the markers D10S541 and D10S215, the nucleic acid encoding, optionally when inserted into the patient, a tumour-suppressing molecule. Tumour suppression may be identified by transfecting a (preferably prostate) tumour cell line with an expression vector comprising the polynucleotide and comparing the tumorigenic properties of the transfected cell line with the parental line in a xenograft model (e.g. nude mice).

Preferably, the method is for treating prostate cancer. More preferably, the nucleic acid is a tumour suppressor gene which, in this context, is a therapeutic gene. The wild-type tumour suppressor gene is preferred. Still more preferably the nucleic acid comprises a suitable delivery system.

Although adenovirus derived vectors are suited for the repair of gene defects in resting or slowly dividing tissue cells, retrovirus derived vectors specifically target rapidly dividing cells (e.g. tumour cells) and are therefore suited for the in vivo treatment of cancer therapies.

Both the amount of therapeutic protein produced and the duration of production are important issues in gene therapy. Consequently, the use of viral vectors capable of cellular gene integration (e.g. retroviral vectors) may be more beneficial than non-integrating alternatives (e.g. adenovirus derived vectors) when repeated therapy is undesirable for immunogenicity reasons.

Where the therapeutic gene is maintained extrachromosomally, the highest level of expression is likely to be achieved using viral promoters, for example, the Rous sarcoma virus long terminal repeat (Ragot et al (1993) *Nature* 361, 647–650; Hyde et al (1993) *Nature* 362, 250–255) and the adenovirus major late promoter. The latter has been used successfully to drive the expression of a cystic fibrosis transmembrane conductance regulator (CFTR) gene in lung epithelium (Rosenfeld et al (1992) *Cell* 68, 143–155). Since these promoters function in a broad range of tissues they may not be suitable to direct cell-type-specific expression unless the delivery method can be adapted to provide the specificity. However, somatic enhancer sequences could be used to give cell-type-specific expression in an extrachromosomal setting.

Where withdrawal of the gene-vector construct is not possible, it may be necessary to add a suicide gene to the system to abort toxic reactions rapidly. The herpes simplex virus thymidine kinase gene, when transduced into cells, renders them sensitive to the drug ganciclovir, creating the option of killing the cells quickly.

The use of ectotropic viruses, which are species specific, may provide a safer alternative to the use of amphotropic viruses as vectors in gene therapy. In this approach, a human homologue of the non-human, ectotropic viral receptor is modified in such a way so as to allow recognition by the virus. The modified receptor is then delivered to cells by constructing a molecule, the front end of which is specified for the targeted cells and the tail part being the altered receptor. Following delivery of the receptor to its target, the genetically engineered ectotropic virus, carrying the therapeutic gene, can be injected and will only integrate into the targeted cells.

Virus-derived gene transfer vectors can be adapted to recognize only specific cells so it may be possible to target the cancer cell, such as prostate tumour cell. Similarly, it is possible to target expression of the therapeutic gene to the cancer cell, particularly prostate cell, using a prostate-specific promoter such as that for the PSA gene.

A further aspect of the invention provides a method of treating cancer comprising the step of administering a molecule according to the ninth aspect of the invention to the patient, the said molecule further comprising a cytotoxic moiety. The cytotoxic moiety may be directly cytotoxic (such as ricin, a suitable drug or suitable radionuclide) or it may be indirectly cytotoxic (such as an enzyme which is capable of converting a relatively non-toxic pro-drug into a relatively toxic drug; see for example WO 88/07378 and WO 91/11201).

Suitably, the molecule according to the ninth aspect of the invention is an antibody, preferably monoclonal antibody, or fragment thereof.

The aforementioned compounds of the invention or a formulation thereof may be administered by parenteral (e.g. subcutaneous or intramuscular) injection but preferably into the tumour. The treatment may consist of a single dose or a plurality of doses over a period of time.

Whilst it is possible for a compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline which will be sterile and pyrogen free.

Further aspects of the invention provides for the use of a molecule according to the ninth aspect of the invention for the manufacture of a medicament for treating cancer.

It is particularly preferred that for the diagnostic methods and uses of the invention that any nucleic acid used in such methods, is a nucleic acid capable of selectively hybridising to the gene corresponding to the cDNA insert of clone IMAGE 264611.

It is particularly preferred that for the methods of treatment of the invention which use a tumour suppressor gene that the gene is the gene corresponding to the cDNA insert of clone IMAGE 264611 or a suitable variant thereof, for example a truncated version or an intron-free version such as a cDNA. It is particularly preferred that the polypeptide capable of being encoded by a nucleic acid comprising a tumour gene which nucleic acid is capable of selectively hybridising to the said region of human chromosome 10 is a polypeptide capable of being encoded by the gene corresponding to the cDNA insert of clone IMAGE 264611.

Abbreviations used: SSCP, single-strand conformation polymorphism; PCR, polymerase chain reaction; YAC, yeast artificial chromosome; CEPH, Centre d'Etude du Polymorphisme Humain.

BRIEF DESCRIPTION OF THE FIGURES AND CERTAIN TABLES

FIG. 1(a) shows Examples of allele loss at microsatellite markers on 10q23-q25 in prostate tumours. The upper boxed figure beneath each peak gives the length of the allelic fragment; the lower figure is the relative peak height. 'Shoulder' peaks to the left of the main peaks are due to polymerase slippage during PCR.

FIG. 1(b) Microsatellite instability. Instability, thought to result from DNA mismatch repair errors (10), was seen in 1/37 tumours at 21/24 loci. Fragment lengths are given beneath each peak. The example shown here probably reflects deletion of the 207 bp allele in conjunction with expansion of the 213 bp allele.

FIG. 2 shows allele loss at 10q23-q25. Tumour numbers correspond to those in FIG. 4. Marker numbers in italics are D10S numbers (7). Markers denoted 'AFM' have yet to be assigned D numbers; the full marker names are AFMa051tb9, AFMa124wd9, AFMa064za5, AFMa301ex1 and AFMa273ye1. Tumours 8, 16, 24, 30 and 31 also show allele loss at markers D10S189 and/or D10S570 on the p-arm of chromosome 10, implying whole chromosome loss. The smaller numbers give the approximate genetic distance between markers in centiMorgans. There is a clearly defined common region of deletion between markers AFMa124wd9 and D10S583, a distance of approximately 9 centiMorgans. By contrast, only tumours 1 and 11 show specific loss of markers around Mxil and in both instances this is in conjunction with allele loss in the AFMa124wd9-D10S583 region.

FIG. 3 shows Mxil loss in prostate tumours: assessment of allele loss at the $(AAAAC)_n$ polymorphism in the 3' untranslated region of the Mxil gene in tumours 1 and 11, which show specific loss of adjacent microsatellite markers, by fluorescence based typing. The boxed numbers beneath each peak give the allele fragment length (upper) and relative peak height (lower). Tumour 1 shows clear loss of Mxil (peak height reduction 58%) whereas tumour 11 shows no apparent loss of Mxil, despite showing loss of adjacent microsatellite marker AFMa273ye1.

Table 2 shows the results of assessment of prostate tumours for 10q23-q25 loss.

Tables 3 to 37 describe the sequenced inserts of the expressed sequence tags (ESTs) which are derived from the gene corresponding to the cDNA insert of IMAGE clone 264611 (SEQ ID NO:S 22–56, 78–94 and 61 (PCR primers)).

FIG. 6 (SEQ ID No 11) shows the complete sequence of a cDNA of a particularly preferred nucleic acid molecule. Potential position of introns is shown (the "ss" above a dinucleotide denotes the splice site). The 3' untranslated sequence is in lower case.

FIG. 7 (SEQ ID No 12) shows the translation in one reading frame of the nucleotide sequence of FIG. 6.

FIGS. 8 to 15 (SEQ ID No 13 to 20 and 57(FIG. 9 exon 2B)) show the sequence of exons from the gene corresponding to IMAGE clone 264611 and flanking intronic sequences. Coding sequence is in upper case and intronic sequence is in lower case. PCR amplimers are in bold type.

Although the exons are numbered consecutively, there may be more upstream or downstream exons and each given "exon" may be subdivided into smaller exons. R=a purine.

FIGS. 16 to 24 (SEQ ID No 58 to 60 and 62 to 68) show revised sequence of exons from the gene corresponding to IMAGE clone 264611 and flanking intronic sequences. Coding sequence is in upper case and intronic sequence is in lower case. It may be more conventional to number the exons 1, 2, 3, 4, 5, 6, 7, 8 and 9 rather than exons 1, 2a, 2b, 3, 4, 5, 6, 7 and 8 as they are numbered. The sequence information in FIGS. 16 to 24 is almost identical to that in FIGS. 8 to 15 the difference being that a more accurate determination of the sequence has been made. The sequence information in FIGS. 8 to 15 is sufficient for the practice of the invention and, in any case, with the information given in FIGS. 8 to 15 the more accurate determination shown in FIGS. 16 to 24 can readily be achieved by the person skilled in the art without undue effort. FIG. 19 shows normal polymorphic variants surrounding exon 3.

Figure 25:
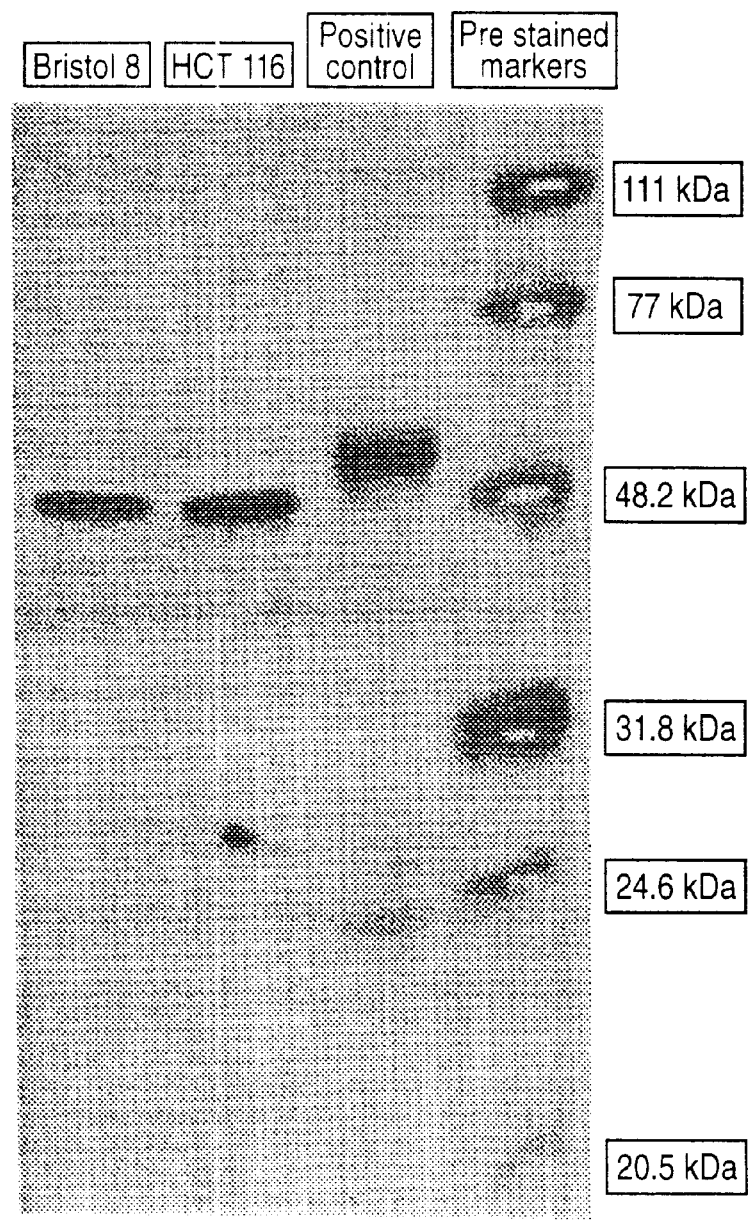

FIG. 25 shows a western blot using an antibody which recognises the polypeptide described in FIG. 7. The samples are from a human lymphoblastoid line (Bristol 8; BRI8) and a colorectal line (HCT 116).

EXAMPLE 1
Localization of a Prostate Tumour Suppressor Gene to the 10q23-q24 Boundary
Materials and Methods
DNA Preparation Tumours and venous blood samples were obtained from men undergoing transurethral resection of the prostate. Tumour tissue was microdissected away from normal tissue and tumour and blood DNA prepared as described previous (6).
PCR PCR was performed in 50 $\mu$l reactions containing 30 ng template DNA, 1×PCR buffer (Boehringer Mannheim), 20 pmol primter, 20 $\mu$M dNTPs (Boehringer Mannheim) and 1 unit of Taq polymerase (Boehringer Mannheim) on a Gene-Amp 9600 thermal cycler (Perkin-Elmer Cetus). For amplification of microsatellite CA repeat markers (7) one of the primers was tagged with a fluorescent label (JOE, FAM, HEX or TAMRA; Applied Biosystems). Microsatellite reaction mixtures were given 30 cycles of 30 seconds @ 94°, 30 seconds @ 55° and 30 seconds @ 72°, preceded by a 3 minute hot start at 95°. The annealing temperature was lowered to 50° for amplification of Mxil helix-loop-helix and leucine zipper exons (5), and increased to 60° for amplification of the 3' exon; primer sequences for 3' exon amplification are 5'-GAGATTGAAGTGGATGTTGAAAG-3' (SEQ ID No 7) (A) and 5'-AAATACAGGTCCTCTGACCC-3' (SEQ ID No 8) (B) and give a 319 or 324 bp product. To facilitate fluorescence based typing of the (CAAAA)$_n$ polymorphism, primer A was tagged with FAM.
Allele Typing Microsatellite allele sizes and loss of heterozygosity were determined by size separation of PCR products in a 6% denaturing polyacrylamide gel in the presence of a 2500-ROX size standard (Applied Biosystems) and detection with an 373A DNA sequencer running Genescan software (Applied Biosystems), following the manufacturer's guidelines. Up to 10 markers, distinguishable by size or fluorescent tag, were typed simultaneously. The resulting data were analysed using Genotyper software (Applied Biosystems).

It is also possible to detect LOH and to assess allele loss by staining the gel with ethidium bromide and visualizing the PCR products using a UV source, or transferring the products to a nylon or nitrocellulose membrane and hybridising with a radioactive probe derived from the marker DNA sequence (such as a radiolabelled oligonucleotide used as a primer in the initial PCR amplification). In this case the PCR products are detected by exposure of the filter to an X-ray film and allele loss may be assessed by eye or, alternatively, by densitometry.
SSCP Following amplification of Mxil introns, 10 $\mu$l of PCR products were mixed with 10 $\mu$l formamide and heated to 90° C. for 3 minutes. The denatured products were run in a 6% non-denaturing polyacrylamide gel at 25W for 4–6 hours with fan-assisted cooling to maintain a temperature of less than 25° C. (8). DNA was transferred to a nylon membrane (Hybond N+; Amersham) and hybridized at 68° C. for 3–4 hours with a mixture of both PCR primers following end labelling with 32P-dCTP (Amersham) using Terminal Transferase (Gibco-BRL). After washing in 2×SSC/0.1% SDS for 5–10 minutes, filters were exposed to X-ray film for 1–24 hours at −70° C.
DNA Sequencing Following purification by passage through a Centricon-100 column (Amicon), PCR-amplified Mxil exons were sequenced using a PRISM cycle sequencing kit (Applied Biosystems) and a 373A DNA sequencer running 373A collection and analysis software (Applied Biosystems) in accordance with the manufacturer's instructions. Each exon was sequenced twice (once from each end) from independent PCR reactions. Sequence electropherograms were aligned using Sequence Navigator software (Applied Biosystems) and compared by eye.
Results A total of 37 prostate tumours of various and histopathological grades and stages (Table 2) were typed for loss of heterozygosity at 24 CA repeat markers spanning 10q23-q25 (7). Tumour tissue was microdissected away from normal tissue prior to DNA extraction and tumour microsatellite profiles compared to those from lymphocyte DNA to determine allele loss. 8 samples of benign hyperplastic tissue were also studied. We considered a tumour DNA sample to be showing allele loss if a reproducible signal reduction of greater than 20% as compared to normal tissue was observed, although in practice the degree of reduction was frequently much greater and in some instances approached 100%. Examples of allele loss are shown in FIG. 1. A total of 23 tumours (62%) showed allelic loss at one or more markers on 10q23-q25 (Table 2). Of these, 8 showed loss at all informative markers typed, and of these 8 a further 5 also showed allele loss at markers on the p arm, suggesting absence of the entire chromosome, possibly through non-disjunction. The allele loss data are summarized in FIG. 2. No loss was seen in the benign hyperplastic tissue samples. One tamour showed microsatellite instability at the majority of loci (21/24; see FIG. 1), presumably due a defective DNA mismatch correction system (10). There is no clear correlation of loss of 10q with tumour stage or grade, suggesting that 10q losses may occur at any time during tumour progression.

The retinol binding protein 4 gene (RBP4 and the cytochrome P450IIC gene cluster (CYP2C) were positioned on the deletion map following the identification of yeast artificial chromosome (YAC) clones bearing both these loci and adjacent microsatellite markers D10S185 and D10S571 (11). The map clearly reveals a common region of deletion proximal to RBP4 and CYP2C which have been cytogenetically mapped to 10q23-24 and 10q24.1 respectively (12, 13)

(FIG. 2). This region is lost in all of the tumours showing 10q loss in our study, with the exception of tumour 37, which was not informative for the markers from this area. Tumours 1, 3, 6, 13, 14 and 15 define a minimal region of deletion between markers AFMa124wd9 and D10S583, a distance of approximately 9 centiMorgans.

Eagle et al have recently identified mutations in the Mxil gene at 10q25 in a small number of prostate tumours, leading to speculation that Mxil can act as a tumour suppressor (1, 5). We were able to place Mxil on the deletion map after confirming its presence on CEPH mega-YACs 936-h-5 and 966-h-9, which have been shown to overlap with YACs bearing the microsatellite marker D10S597 (14). Only two tumours, 1 and 11, showed specific loss of markers immediately flanking Mxil and in both cases this was in conjunction with allele loss in the AFMa124wd9-D10S583 region (FIG. 2).

In an attempt to further clarify the role of Mxil loss in tumour progression, we screened tumours 1 and 11, and those showing loss of the entire region, for Mxil mutations by PCR amplification of individual exons followed by SSCP analysis (8). Primers for PCR amplification of exons encoding helix-loop-helix and leucine zipper domains were taken from Eagle et al (5). For amplification of the final 3' exon, primers derived from the immediate 5' end of the exon and from within the 3' untranslated sequence were used (4, 5). These 3 pairs of primers give 66% coverage of the coding sequence of Mxil. The genomic structure of the 5' end of the Mxil gene has not yet been determined and we were therefore unable to analyse exons 5' to the helix-loop-helix domain. SSCP analysis failed to detect any mutations in the two-thirds of Mxil coding sequence covered.

Figure 3:
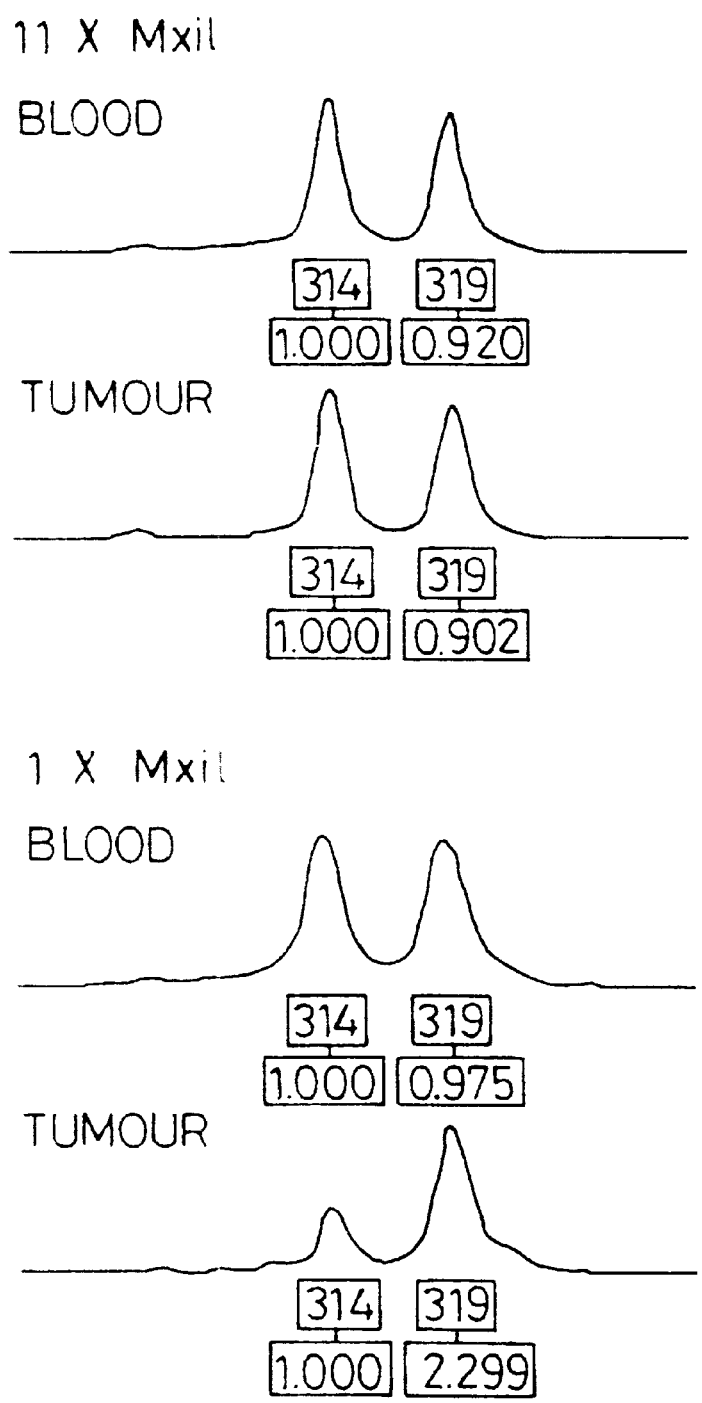

In addition to SSCP analysis we directly sequenced those exons which encode the helix-loop-helix and leucine zipper domains previously shown to be mutated in prostate tumours (5). Again no mutations were detected. Although we were unable to detect Mxil mutations in any of the tumours by either approach, we did detect a common polymorphism in the 3' untranslated region by SSCP which subsequent sequence analysis showed to result from length variation in a $(AAAAC)_n$ tandem repeat, giving two alleles, $(AAAAC)_4$ and $(AAAAC)_5$. Eight of the tumours showing loss of the entire 10q23-q25 region or allele loss at CA repeat markers in the vicinity of Mxil (Nos. 1, 8, 11, 16, 17, 21, 23 and 30) were heterozygous for this polymorphism, making it possible to assess these tumours for actual Mxil loss. 6 of the tumours (1, 8, 16, 17, 23 and 30) showing loss of adjacent markers also showed loss of Mxil as determined by fluorescence based typing (FIG. 3). Of these, 5 showed loss of the entire 10q24-q25 region (FIG. 2). Therefore, from a total of 23 tumours showing 10q23-q25 losses, we were able to identify only one tumour (No. 1) showing specific deletion of Mxil (as opposed to loss of other 10q23-q25 regions or of the entire region), and this was in conjunction with deletion of AFMa124wd9-D10S583.

We were also able to use this polymorphism to determine the effect of contaminating normal tissue on the efficiency of mutation detection in tumours by cycle sequencing. Exon 5 including the immediate 3' untranslated DNA was sequenced in those tumours showing Mxil loss (tumours 1, 8, 16, 17, 23 and 30). For tumour 8, which showed the greatest degree of loss of the deleted allele, the retained allele was clearly identified. The remaining tumours gave highly ambiguous sequence data following the (AAAAC)n repeat, resulting from combined termination products from the two alleles (not shown). It is therefore likely that any disabling mutations resulting from small deletion or insertion events in the retained copies of Mxil would have been detected by cycle sequencing.

Discussion

The data presented here indicate the presence of a prostate tumour suppressor gene (or genes) at the 10q23-q24 boundary, and more specifically between markers AFMa124wd9 and D10S583, a region spanning approximately 9 centiMorgans. This region was deleted in 22 of 23 prostate tumours showing 10q losses, with the 23rd being uninformative for the relevant markers. 10q loss may be an early event in some instances of prostate carcinogenesis; losses were observed in early as well as late stage tumours. Alternatively, 10q loss may be more important in progression of the established tumour rather than genesis given that losses were not observed in benign hyperplastic tissue samples. However, the relationship between benign prostatic hyperplasia and carcinogenesis is unclear at present and such lesions may not be a precursor to malignancy.

Although Mxil has been shown to be mutated in prostate tumours, only a small proportion of cells in each tumour were found to be carrying Mxil mutations (5). The authors offer two possible explanations. The first is that the tumours studied may have contained significant amounts of non-neoplastic tissue. The second is that mutated Mxil alleles are only present in a small number of neoplastic cells. Given that we were unable to detect Mxil mutations in microdissected tumours containing <30% contaminating normal tissue and showing a degree of 10q loss ranging from 25–79% (as estimated by microsatellite allele loss—see Table 2) the latter seems more likely. This also implies that mutation of the retained Mxil allele occurs after loss of the deleted allele. The combined evidence of no mutation detection, or detection in only a small percentage of tumour cells, coupled with the allele loss data indicates the presence of a tumour suppressor gene (or genes) at 10q23-q24 of greater significance than Mxil in prostate tumour progression.

Loss or rearrangement of 10q24-q25 is not restricted to prostate adenocarcinoma; it has also been observed in melanoma, glioma and non-Hodgkins lymphoma (15-21), suggesting the presence of a tumour suppressor gene or genes at this location of relevance to several tumour types.

EXAMPLE 2

Identification of DNA Containing a Tumour Suppressor Gene

Figure 4A:
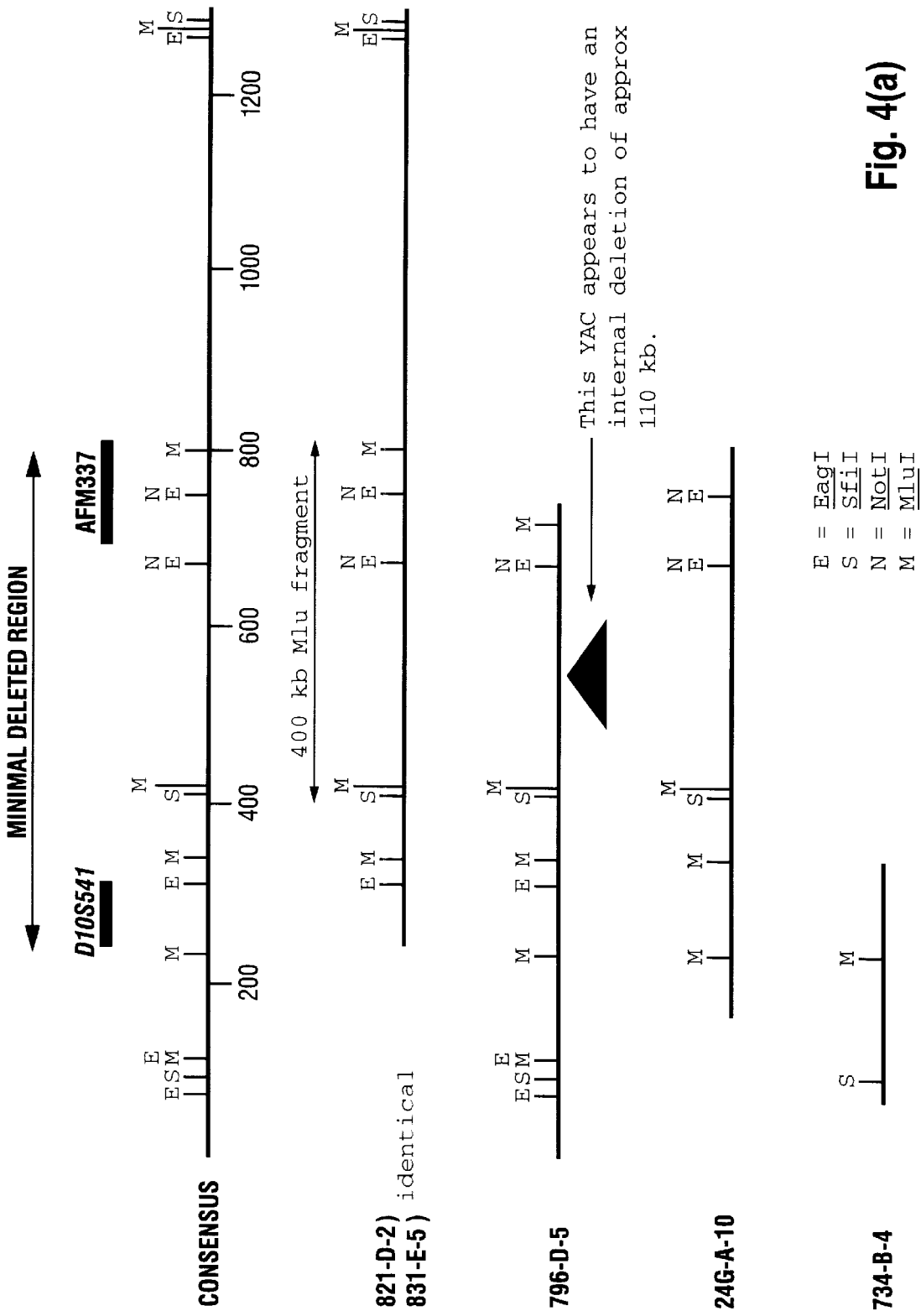
FIG. 4(a) is a physical map of the minimal region showing the position of the YAC clones and markers D10S541 and AFM337.
Figure 4B:
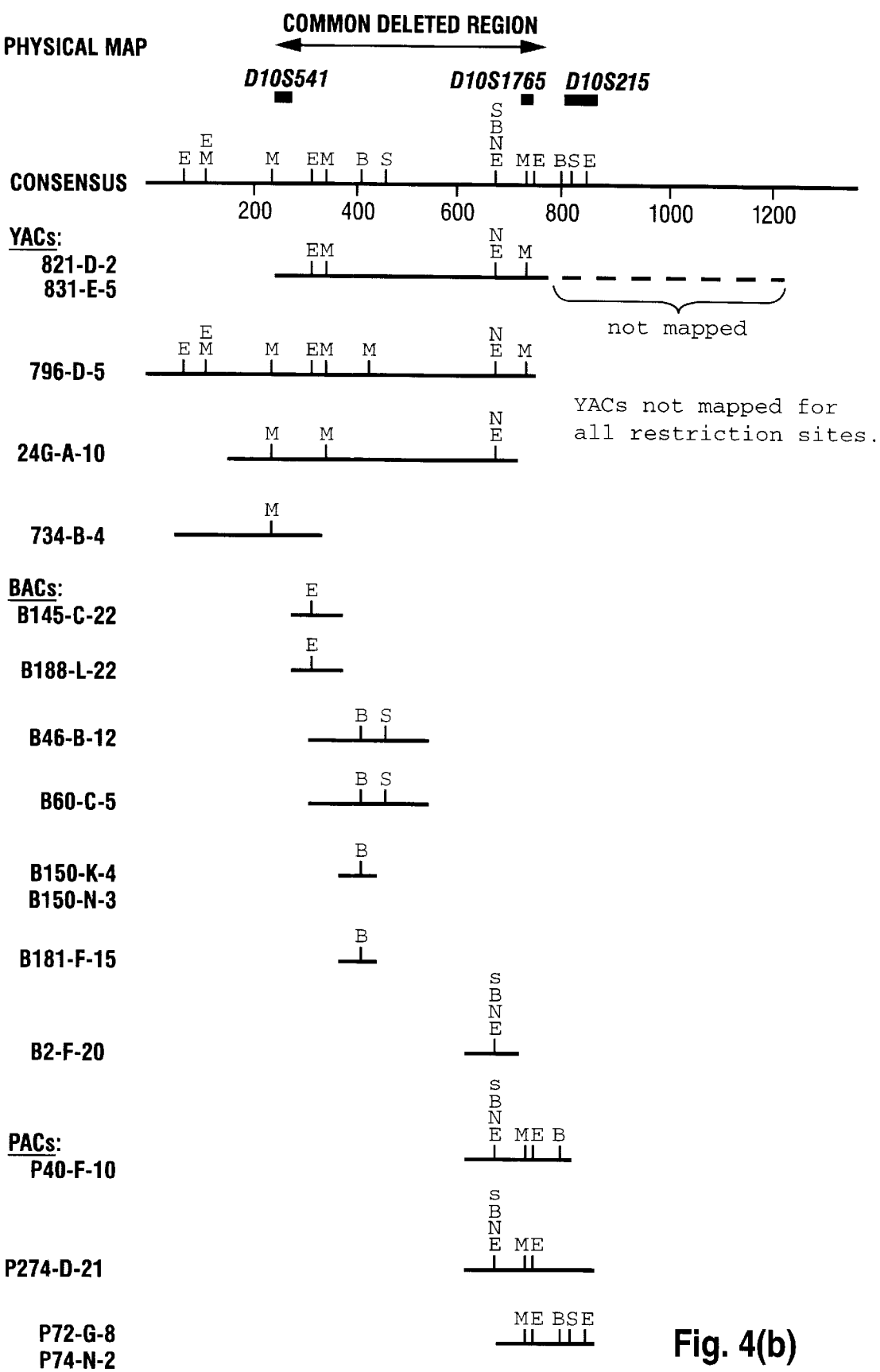
FIG. 4(b) is a more detailed map showing the position of BAC and PAC clones.
Figure 5:
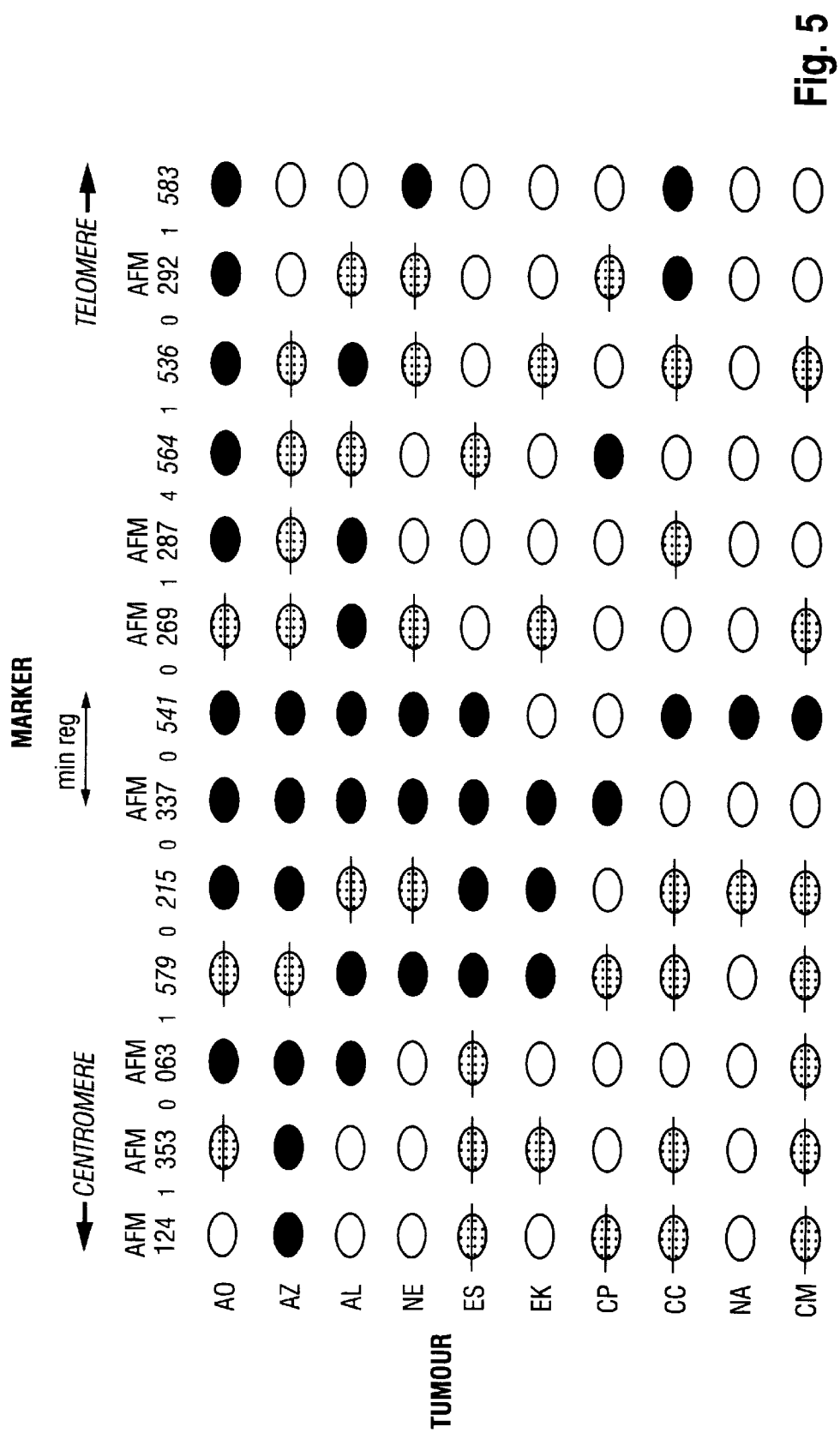
FIG. 5 shows further, more informative, LOH data.

FIGS. 4 and 5 give more detailed mapping data between AFM124 and D10S583, the markers that define the minimal region in the manuscript, allowing us to narrow the minimal region further to the interval between D10S541 and D10S215; more particularly between D10S541 and AFM337xf9, a distance of less than 1 cM. The physical mapping data are summarised below:

TABLE 1

| | Minimal region yeast artificial chromosome (YAC) sequence tag sites (STS) assignments | | | | |
|---|---|---|---|---|---|
| YAC | Approx size (KB) | D10-S579 | D10S215 | AFM337xf9 | D10S541 |
| 746-H-8 | 1200 | + | + | + | + |
| 821-D-2 | 1150 | + | + | + | + |
| 831-E-5 | 1110 | + | + | + | + |
| 921-F-8 | 1570 | + | + | + | + |
| 738-B-12 | 1330 | + | + | | |
| 796-D-5 | 800 | | | + | + |
| 829-E-1 | 1130 | | | | + |

TABLE 1-continued

Minimal region yeast artificial chromosome
(YAC) sequence tag sites (STS) assignments

| YAC | Approx size (KB) | D10-S579 | D10S215 | AFM337xf9 | D10S541 |
|---|---|---|---|---|---|
| 678-F-1 | 480 | + | + | | |
| 839-B-1 | 320 | | | | + |
| 734-B-4 | 280 | | | | + |
| 7B-F12 | 190 | | + | + | |
| 24G-A10 | 640 | | | | + |

All of these YACs other than 7B-F12 and 24G-A10 are publicly available from the CEPH mega-YAC library. 7B-F12 and 24G-A10 are publicly available from the ICI YAC library. Both of these libraries are publicly available from the Human Genome Mapping Project Resource Centre, Hinxton Hall, Hinxton, Cambridgeshire, CB10 1RQ, UK. Sizes for mega-YAC clones are taken from CEPH data. ICI YAC clones were sized by us.
+=STS Assigned to YAC YACs 821-D-2, 831-E-5, 796-D-5, 24G-A-10 and 734-B-4 have been mapped in more detail to give a large scale restriction map of the region (see FIG. 4). This contig does not include all restriction sites. YACs 821-D-2 and 831-E-5 appear to be identical and span the minimal region (D10S541-AFM337xf9). They therefore contain all or part of the tumour suppressor gene.

ESTs (Expressed Sequence Tags) are generated and assigned to genomic regions using the following procedure.
1. Construct cDNA library from the tissue of interest.
2. Select individual clones at random and perform a single sequencing pass to give approximately 200–300 bp of DNA sequence (an EST).
3. Design primers from each EST to allow PCR amplification of an internal fragment (an expressed Sequence Tagged Site or eSTS).
4. 'Bin' ESTs to chromosomes by PCR amplification from monochromosomal cell hybrid DNA (a panel of DNA samples derived from human/rodent cell hybrids, each of which has a single human chromosome).
5. Localize ESTs further by PCR amplification from pools of overlapping YAC clones and finally by PCR assignment to individual YACs.

The polypeptide encoded by the cDNA insert of IMAGE clone 264611 has some similarity to the protein tensin and to auxilin, a protein involved in protein transport to the cell membrane via clathrin coated vesicles. The gene corresponding to the cDNA insert of clone IMAGE 264611 is a tumour suppressor gene.

The prostate tumour suppressor gene or genes are identified by screening a panel of RNAs from prostate and other tumour cell lines, in order to identify an altered, usually reduced, level of transcript. The transcript is likely to be large, as it will probably have a complex function and several sites for disabling mutation 'hits' (cf BRCA1, RB). Cross-species conservation is a good indicator that the gene has a basic cell 'housekeeping' function, the loss of which can lead to a loss of growth control and tumour formation. The prostate tumour suppressor gene cDNA is identified as follows.

Part of one of the YAC clones is used as a probe to screen a prostate cDNA library directly following radiolabelling. The 400 kb Mlu1 fragment (marked on the restriction map in FIG. 4), which covers about 75% of the minimal region, is used as a probe—this fragment can be separated cleanly from a pulsed field gel following digestion. Alternatively, the entire 24G-A10 YAC is used as a probe. A standard colony/filter hybridization approach is used. Suitable BAC or PAC clones may also be used.

Mutation analysis of the entire coding region in tumours shows that the gene is a prostate tumour suppressor gene. This is done by analysing each exon individually for mutations. Methods for mutation analysis used are single-stranded conformation polymorphism (SSCP) analysis (or variations of this technique) and direct DNA sequencing.

Genes located within the region are identified by screening of cDNA libraries with the probes obtained from the human nucleic acid sequence contained within the YACs, BACs and PACs or by exon trapping methods or by sequencing of the human nucleic acid sequence contained within the YACs, BACs and PACs, automated sequencing techniques make this routine, and use of computer programs, e.g. GRAIL II, that distinguish coding sequence. The results are confirmed by RT-PCR of prostate RNA from prostate tissue or a cDNA library.

The prostate tumour suppressor gene or genes are found to be expressed in normal prostate tissue, mutation analysis of the entire coding region shows that expression of the gene(s) may be altered in prostate tumours compared to normal prostate, the product of the genes may be truncated at the protein level, the mRNA product may be truncated, or have altered splicing compared to normal which results in an abnormal protein, the resulting protein encoded by the altered gene may have abnormal properties or distribution within the tissue.

EXAMPLE 3

Diagnostic Applications of Nucleic Acids

Chromosomal deletions in a specific region on chromosome 10 (ie the tumour suppressor gene-containing region at the 10q23-q24 boundary) are detected using interphase fluorescent in situ hybridisation (FISH) on cells in interphase to check for loss. Cells from a biopsy sample are spread across a slide and the cell membrane permeabilised. This allows the reagents for in situ hybridisation to enter the cells containing interphase chromosomes. The BACs or PACs or other suitable probes specific for the region deleted are hybridised to the chromosomes after labelling the probes with a fluorescent dye. A chromosome containing a region of deletion shows no signal; and chromosomes from a cell in which one chromosome 10 has suffered a deletion from this region will show only one signal and not two. Therefore, a method is provided that can detect 10q deletions in biopsies from patients. These are useful indicators of the staging of the grade of the tumour between benign and malignant hyperplasia and may indicate that a more aggressive treatment regime should be undertaken.

Suitable YAC clones, for use as probes, include 821-D-2, 831-E-5, 796-D-5, 24G-A-10 and 734-B-4.

Any of the BAC or PAC clones derived from the region of interest (see physical map) may be used and include 60C5 and 46B12.

It is particularly useful to use a nucleic acid which is capable of selectively hybridising to the gene corresponding to the cDNA insert of clone IMAGE 264611. The gene itself, or a suitably sized fragment thereof, is particularly suited as a probe.

The probe is ideally between 10 kb and 1 Mb, preferably between 60–200 kb.

FISH is described by Bentz et al (1994) *Leukemia* 8(9), 1447–1452.

The BAC or PAC clone (such as BAC clone 60C5) is used on nuclei isolated from prostate tissue. The method for isolating nuclei from frozen tissue is as follows.

Extraction of Nuclei From Frozen Tissue (Adapted from Xiao et al (1995) *Am. J. Pathol.* 147, 896–904)

(1) Cut 2×5×5 mm portion of frozen tissue—take without defrosting whole specimen. Thaw at room temperature for 1–3 minutes. (2) Mince tissue finely in 35 mm plastic petri dish using opposed scalpel blades. (3) Add 1 ml of 0.5% pepsin in 0.9% NaClpH 1.5 to the dish. Transfer to 15 ml centrifuge tube. (4) Incubate in water bath at 37° C. for 15–30 minutes or until most tumour chunks have disappeared. (NB the time taken should be the minimum required to disaggregate the tumour). Vortex every 5 minutes. (5) Add 14 ml of PBS and collect nuclei by centrifugation—5 minutes at 15,000 rpm. (6) Discard all but 0.5 ml of supernatant by aspiration. Resuspend nuclear pellet in the residual supernatant. (7) Apply a drop (10 µl) of suspension onto a non-coated slide. Assess suspension by phase microscopy before drying to determine whether the cell density is appropriate—if nuclei are overcrowded dilute suspension with PBS; if nuclei are sparse add another drop of suspension to the same spot. (8) Air dry the slides. (9) Immerse in 10% buffered formalin for 10 minutes. (10) Air dry. (11) Bake at 55° C. for 2 hours on hot plate. Slides may be stored at this point as follows (dehydrate through ethanol series (75%, 85%, 95% for 2 minutes each; air dry; store slides at −20° C. with dessicant; store residual nuclear suspension in PBS at −70° C. (it can be thawed ×2 without any effect on the quality of the subsequent hybridization)). (12) Before hybridization the DNA needs to be denatured. Place slide on hot plate at 73° C. with 70% formamide/2×SSC pH 7.0 under a coverslip for 2.5 minutes. (13) Dehydrate in ethanol series of icecold 70%, 95% and 100% for 3 minutes each and air dry.

Hybridization

Each hybridization event usually occupies half a slide.

Probe Labelling

The BAC or PAC clone (e.g. BAC clone 60C5) is used as a diagnostic probe. The whole clone is used to generate a labelled probe. A commercially available clone that recognises sequences at the centromere of chromosome 10, e.g. Oncor D10Z1 α-satellite, is used as a control to detect chromosome 10. The two probes are labelled differently so that they may be distinguished. The probes are to be labelled by nick translation with biotin or digoxygenin using a commercially available kit (e.g. Bionick kit, Life Technologies). In an Eppendorf tube mix 20 ng labelled probe+4 µg Cot 1 DNA+2 volumes of ethanol. Dry mixture in a speed vac for 25–30 minutes. Resuspend in 11 µl hybridization mix (2×SSC, 50% formamide, 10% dextran sulphate, 1% Tween 20, pH 7.0). (If 2 or 3 probes have to be hybridized simultaneously then the 12 µl of hybridization mix should be divided equally between them (ie 2 probes 6 µl of hybridization mix each); they should not be put together until after the preannealing stage).

Denature the probe at 85° C. for 5 minutes. Place immediately on ice for a few secs only. Spin quickly to get all the liquid to the bottom of the tube. Pre-anneal at 37° C. for 30 minutes (after this mix 2 or more probes if necessary). Pre-annealed probe is placed on one half of a slide and covered with a 22×22 mm coverslip. Seal around coverslip with rubber solution.

Post Hybridization Washes (Steps Should Now be Carried Out in the Dark ie in a Covered Coplin Jar)

3×5 minutes in 50% formamide, 2×SSC, pH 7.0 at 42° C.
    3×5 minutes 2×SSC, pH 7.0 at 42° C.
    1×3 minutes 4×SSC, 0.05% Tween 20, pH 7.0 (=SSCCT) at room temp Probe Detection Step 1—preincubation with SSCTM. Place 100 µl of SSCTM (=SSCT+5% Marvel=10 mls of SSCT+0.5 g Marvel, spun down before use to remove solids) onto the slide under a 22×50 mm coverslip. Place in a moist chamber at 37° C. for 10 minutes. Wash in SSCT for 3 minutes. (NB All detection reagents are diluted in SSCTM.) For each detection step 100 µl of detection reagent is placed under a 22×50 mm coverslip and placed in a moist chamber at 37° C. for 25–30 minutes. Each step is followed by 3×3 minutes washes in SSCT at room temperature—the coplin jar during these steps should be shaken gently—except the last step which is followed by a 1×5 minutes wash in SSCT and 2×5 minutes wash in PBS. Slides are then dehydrated in an ethanol series (70%, 95%, 100% for 2 minutes each) and air dried. They are then mounted in Cytofluor (UKC ChemLab, Canterbury CT2 7NH, UK) containing DAPI 4,6-diamidino-2-phenylindole as counterstain (see below).

Dual Probe Detection (Two Colour)

Step 2—mouse anti-Digoxygenin FITC, and Avidin-Texas Red. Step 3—rabbit anti-mouse FITC, and anti-Avidin Biotin. Step 4—anti-rabbit FITC, Avidin-Texas Red. Counterstain: DAPI (0.15 µg/ml=5 µl of 30 µl/ml stock solution+995 µl glycerol (Cytofluor).

Results

For normal prostate cells, the 60C5 probe produces two signals (spots) per cell. Two spots per cell are also seen for the chromosome 10 centromeric marker D10Z1. If a prostate cell has only one, or no spots, produced by hybridisation with the 60C5 probe, indicating a deletion in the region covered by that probe, then the cell is cancerous. Furthermore, if the number of spots visualised using 60C5 is less than the number of spots visualised using the chromosome 10 centromeric marker, then a deletion has occurred in the region covered by 60C5, and the cell is cancerous.

The interphase FISH method can be used using genomic clones in the region. Preferably the genomic DNA is about 60–200 kb. Typically, normal tissue shows two dots, whereas tumour tissue shows one or no dots, or alternatively fewer dots than the number of chromosome 10 copies present in any cell. Centromeric repeat sequences are used to demonstrate the presence of chromosome 10 in a cell. However, even a normal tissue will show some cells with only single signals (spots). For a solid tissue, efficiency is typically between 85 and 95%, ie 85–95 nucleic per 100 show two signals. Efficiency is dependent on both the probe and the experimental conditions but may be optimised empirically. Affected tissue shows a significantly greater percentage of cells with only a single signal. The presence in the sample of contaminating, normal, cells will prevent this percentage from reaching 100%. It is therefore desirable to dissect out the area of the cells prior to these assays.

Thus, in summary, the methods and outcomes are: (i) Take tissue sample from patient, dissect out/purify affected area of tissue, and extract nuclei. (ii) Label probe with detectable tag. (iii) Contact probe with prepared sample under hybridising conditions. (iv) Remove, by washing, non-hybridised excess probe. (v) Visualise hybridised probe. Probe hybridised to a single locus is visualised as a signal (spot) by microscopy. (vi) In unaffected tissue, the majority of cells are found to show two signals, per cell. A minority of cells may show less than two spots, due to inefficient hybridisation. (vii) In affected tissues, a significantly greater number of cells are found to show single or no signals from the specific probe. It will be appreciated that contaminating normal cells will affect the proportion of cells seen with two signals.

Prognostic information for the solid tumour, neuroblastoma, has been obtained by other workers using unrelated probes but similar FISH methods (Taylor et al (1994) Br. J. Cancer 69, 445–451).

EXAMPLE 4
Detection of Polypeptides

A monoclonal antibody directed at the tumour suppressor gene product is labelled with $^{125}I$. A sample of prostate tissue is prepared and proteins separated by SDS-polyacrylamide gel electrophoresis. The proteins are electroblotted onto a nitrocellulose membrane and the membrane incubated with the monoclonal antibody.

Presence of the tumour suppressor gene product is detected. The absence of the product indicates an increased susceptibility to prostate cancer.

EXAMPLE 5
Therapeutic Applications

The tumour suppressor gene is introduced into a patient who is susceptible to prostate cancer using a suitable retroviral vector.

EXAMPLE 6
Use of IMAGE Clone 264611 (and Primer or Probes Derived Therefrom) in Diagnosing Prostate Cancer Clone 264611 (and primers or probes derived from it) are used for detection of altered mRNA levels by in situ

EXAMPLE 7
Loss of-heterozygosity (LOH) as a Diagnostic/prognostic Tool

Loss of heterozygosity studies using markers D10S541, D10S1765 (AFM337xf9) and D10S215 are used to determine loss of the D10S541-D10S215 interval.

These markers consist of blocks of tandem CA repeats flanked by unique DNA sequence and are commonly known as microsatellites. The number of CA repeats shows variation between alleles (homologs on different chromosomes). This may be exploited to distinguish the two homologous chromosomal regions bearing these markers in a given tissue. By comparing biopsied prostate DNA (e.g. from urine or semen) microsatellite profiles with those of DNA extracted from blood or cheek cells (e.g. by means of a mouthwash), loss of one homolog of the D10S541-D10S215 interval in prostate tissue can be assessed.

This method is particularly useful for distinguishing between neoplasia (loss of one homolog) and hyperplasia (no loss) of the prostate.

Figure 1A:
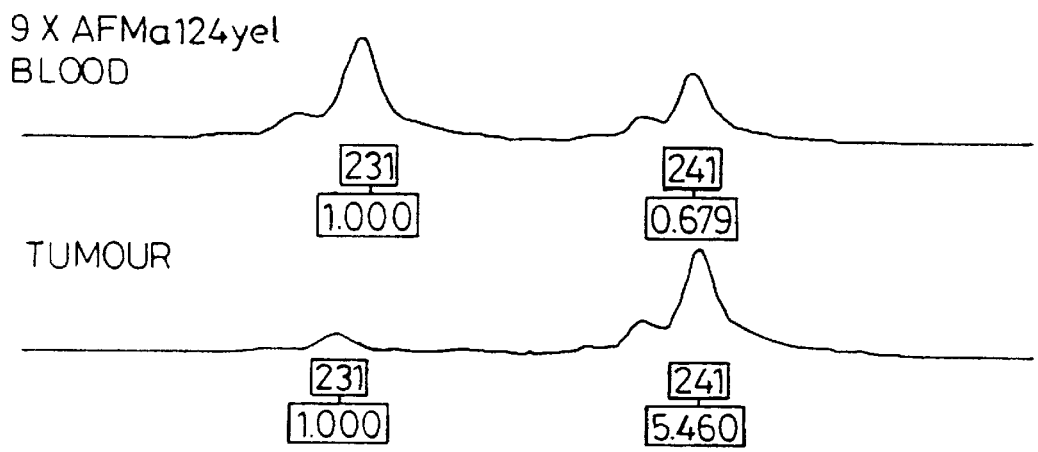
Figure 1B:
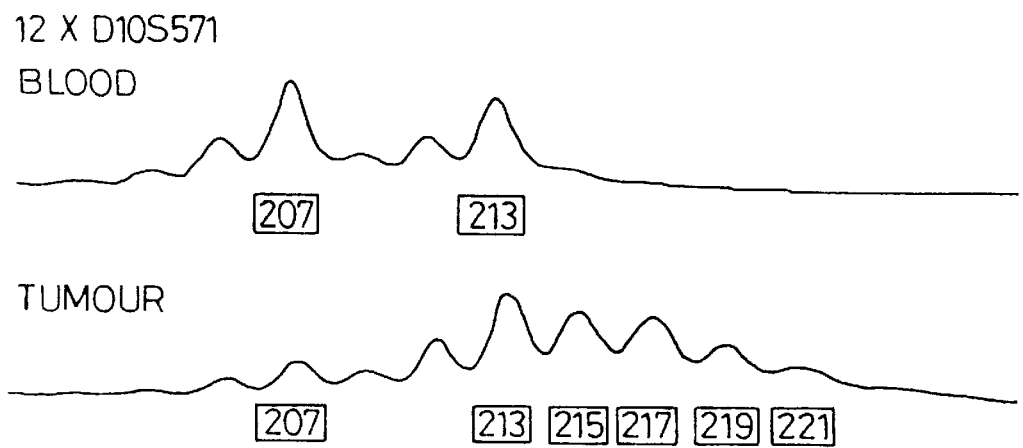

The methodology for this approach is described in more detail in Example 1 and the examples given in FIG. 1a and the Figure legend.

PCR primer sequences are:

| | | |
|---|---|---|
| D10S541: | 5'-AAGCAAGTGAAGTCTTAGAACCACC-3' | (SEQ ID No 1) |
| | 5'-CCACAAGTAACAGAAAGCCTGTCTC-3' | (SEQ ID No 2) |
| D10S215: | 5'-TGGCATCATTCTGGGGA-3' | (SEQ ID No 3) |
| | 5'-GCTTTACGTTTCTTCACATGGT-3' | (SEQ ID No 4) |
| D10S1765: | 5'ACACTTACATAGTGCTTTCTGCG-3' | (SEQ ID No 5) |
| | 5'-CAGCCTCCCAAAGTTGC-3' | (SEQ ID No 6) | hybridisation, Northern analysis (also detection of altered mRNA species profile) or quantitative RT-PCR. For expression detection methods (other than in situ hybridisation), it is preferable to use substantially pure tumour tissue. In situ hybridisation uses fixed tissue. A positive result indicative of prostatic cancer is altered expression levels compared to prostate tissue which is not cancerous or an altered pattern of transcript expression compared to normal prostate tissue. Samples suitable for analysis also include fresh prostate tissue, tissue collected by needle biopsy from prostate or from metastasis.

PCR primers derived from the cDNA insert of IMAGE clone 264611 are used for RT-PCR followed by mutation detection or protein truncation assays. A result indicative of prostate cancer is the detection of coding mutations, or a truncated protein product.

Thus, the methods of this Example are useful in detecting the presence of prostate adenocarcinoma.

Primers derived from intronic sequences of the gene corresponding to IMAGE 264611 (for example, those shown in FIGS. 29 to 34), are used to amplify the gene exons, which are then examined for mutations by various methods (sequencing, SSCP or any form of mismatch detection) or used in protein truncation assays. Suitable samples include fresh prostate tumour tissue, prostate cells recovered from blood, urine or semen, and DNA recovered from paraffin blocks.

Other methods for detecting mutations useful in this example include DGGE, direct sequencing, mis-match cleavage, heterozygote analysis and chemical cleavage.

Double deletion of the gene may be detected by analogous methods.

EXAMPLE 8
Mutation in Tumour Suppressor Gene

Analysis of nucleic acid in the preferred nucleic acid of the invention, comparing a sample from a tumour with a sample from blood, revealed the following mutation:

BLOOD: GAGGCCCTAG ATTTCTATGG GGAAGT-AAGG
    ACCAGAGACA AAA                                    (SEQ ID No 9)

TUMOUR: GAGGCCCTAG ATTTCTATGG GGAAGTTAAGG
    ACCAGAGACA AAA (SEQ ID No 10)

There is a T insertion in exon 4 (tumour 24). This mutation causes a frameshift, resulting in the incorporation of inappropriate amino-acids into the protein product following the insertion and ultimately premature truncation as the result of encountering an out-of-frame stop codon.

This mutation was detected following PCR amplification of exon 4 (using the intronic primers described in the figure of exon 4) and subsequent sequencing of the PCR product using standard methods.

Tumour CS exon2A. G deletion:

BLOOD: TTTATCCAAACATTATTGCTATGG-
    GATTTCCTGCAGAAAGACTT              (SEQ ID No 69)

TUMOUR: TTTATCCAAACATTATTGCTATGG-ATTTCCTGCA-
    GAAAGACTT              (SEQ ID No 70)

Tumour EK exon2A. Complex deletion/duplication:

BLOOD: ATTATTGCTATGGGATTTCCTGCAGAAA-
GACTTGAAG-GCGTATACAGGAA (SEQ ID No 71)

TUMOUR: ATTATTGCTATGGGATTTCCTGCAGAAA-
GACTTGAAGacagaaagACAGGAA (SEQ ID No 72)

These mutations were found in samples from thee different patients.

TABLE

Frameshift mutations in prostate tumours

| Tumour stage[a] | Tumour grade[b] | 10 q allele loss detected | Mutation | Exon |
|---|---|---|---|---|
| T4M1 | 3 | Yes | insT: normal: AGT-AAG mutant: AGTTAAG | 4 |
| T3M1 | 3 | No[c] | delG: normal: TGGGATT mutant: TGG-ATT | 2 |
| T2M1 | 3 | Yes | Complex duplication/deletion: normal: GCAGAAAGACTTGAAG-- GCGTATACA (SEQ ID NO: 73) mutant[d]: GCAGAAAGACTTGAAGacagaaag ACA (SEQ ID NO: 74) | 2 |

[a]Staging is based on digital rectal examination and bone scan. All tumours show metastasis.
[b]WHO gradings: 1, well differentiated; 2, moderately differentiated; 3, poorly differentiated; 4, mixture of differentiation.
[c]No allele loss was detected at 10q23/24 in this tumour, suggesting a second relatively small mutation event within the boundaries of D10S541 and D10S1765.
[d]The sequence in bold and italic type appears to have duplicated and inserted downstream (lowercase type) giving an overall insertion of 2 bp.

As all three mutations were detected in late-stage tumours showing metastasis, inactivation of the gene may be involved in a pathway leading to metastatic potential.

EXAMPLE 9

Use of Antibodies Directed Against Neptides Derived From the Polypeptide Whose Sequence is Given in FIG. 7

The following peptides were synthesised.

(1) APGRGSESPVTISRAGNAGE (Ref PSG1) (SEQ ID No 75)
(2) QLKVKIYSSNSGPTRREDKFMY (Ref PSG2) (SEQ ID No 76)
(3) KVKLYFTKTVEEPSNPEAS (Ref PSG3) (SEQ ID No 77)

These peptides are all derived from the sequence shown in FIG. 7.

The peptides were conjugated to keyhole limpet haemocyanin using the following method:

1. Weigh out peptide and an equal weight of carrier (Keyhole Limpet Heamocyanin). KLH is available from Calbiochem.
2. Dissolve peptide and carrier protein in 0.1M NaHCO$_3$ at a concentration of 2 carrier mg/ml.
3. Thaw out a fresh vial of glutaraldehyde. (Sigma ultra pure grade 1, obtained as 1 ml aliquots of 25% stock. Store at −20° C.). Add glutaraldehyde to peptide and carrier solution to a final concentration of 0.05%. Mix in a glass tube end over end or stirring at room temperature overnight. The solution will usually go a pale yellow colour. It may be necessary to raise the pH to 7–8 by adding more NaOH. (Commercial preparations of glutaraldehye have a pH of 3.1 and the glutaraldehyde is in the cyclic hemiacetal form. At pH 7–8 glutaraldehyde forms a,b-unsaturated polymers which may form Schiff bases with the amino groups of the peptide).

Do not use Tris or buffers containing amino groups, ammonium ions or azide.

4. EITHER: Dialyse against DDW for 12 hours and lyophilise the coupled carrier. NB For PPD conjugates, use low MWt cut-off dialysis tubing (we use material which only allows molecules below 2 kDa to pass through). To assess yield, weigh the lyophilised material and determine percentage of peptide coupled.

OR: Because coupling efficiency is usually reasonable, and not too critical anyway, it is easier to do the following.

Add 1M glycine ethyl ester (pH at 8.0 with NaOH) to a final concentration of 0.1M and leave for 30 minutes at room temperature. Then precipitate the coupled carrier with 4–5 volumes of ice cold acetone at −70° C. for 30 minutes. Pellet protein at 10,000×g for 5 mins, pour off acetone, air dry pellet, and redisperse it in saline (0.9% NaCl) at 1 mg carrier/ml. As the pelletised protein is rather sticky, it is often impossible to resuspend. An ultrasonic bath or a Dounce homogeniser may help to resuspend the pellet.

Notes

Coupling can also be done in 0.1M NaHCO$_3$/0.1% SDS should peptide or carrier prove insoluble in coupling buffer.

Typical reagent quantities

KLH 6.25 mg (from Calbiochem 374817 KLH in 50% glycerol)

Peptide 6.25 mg 0.1M NaHCO$_3$ @ 3 ml glutaraldehyde 6 microlitres glycine ethyl ester 0.3 ml saline @ 6.5 ml Antibodies were raised using a standard rabbit immunisation protocol. Briefly, this is:

Dose of immunogen about 200 µg for primary immunisation and 100 µg for subsequent boosts.

Emulsification with Freund's adjuvant is done. All injections are made subcutaneously at multiple sites. The volume of the immunogen plus adjuvant did not exceed 0.25 ml at each of 4 sites for each immunisation, therefore the volume of immunogen is not more than 0.5 ml for each injection.

A pre-bleed (5 ml) was done followed by primary immunisation in complete Freund's adjuvant. A first and second boost in incomplete Freund's adjuvant was carried out followed by a first test bleed (5 ml). A third and fourth boost in incomplete Freund's adjuvant was carried out followed by a second test bleed (5 m). Fifth and sixth boosts in incomplete Freund's adjuvant were carried out and the rabbit was later bled out.

For unknown reasons neither PSG1 or PSG2 gave an antibody response to the polypeptide.

PSG3 is the peptide which worked. A scan of a western blot is shown in FIG. 25. Ten µg of cell lysate was run on a 12.5% reducing acrylamide gel. The blot was probed with 1:2000 dilution of rabbit HB-10 serum (anti-PSG3) The blot includes two cell lines (BRI8 which is a human lymphoblastoid line and HCT116 which is a colorectal line). These are positive with the anti-PSG3 antibody.

The positive control is rabbit IgG to show that the developing agent is working.

EXAMPLE 10
Expression Profiles in a Range of Human Tissues

The 1.7 kb insert from IMAGE EST clone 264611, which contains the entire open reading frame, gives a constant pattern of at least five bands ranging from 2.5 to 5.5 kb in all tissues tested (leukocytes, colon, small intestine, ovary, testis, prostate, thymus, spleen). A probe derived from exon 1 detects a single 2.5 kb transcript. The origin of the remaining bands is unknown; they may represent further mRNA splice variants, or other mRNAes from genes of related sequence.

EXAMPLE 11
Polymorphism

A polymorphism exists as shown in FIG. 19. The sequences indicated as Exon 3.1 and Exon 3.2 are both found in blood (i.e. non-tumour tissue). The five bases underlined in the sequence Exon 3.1 are deleted in the sequence Exon 3.2. The polymorphism may be a useful marker for the gene, particularly in assessing loss of heterozygosity, especially in those people who are heterozygous with respect to the polymorphism.

TABLES

TABLE 2

Prostate tumours assessed for 10q23–q25 loss

| TUMOUR | STAGE[a] | GRADE[b] | PATIENT AGE | 10q LOSS[c] |
|---|---|---|---|---|
| 1 | T1 M0 | 2 | 81 | + (0.56) |
| 2 | T2 M0 | 2 | 84 | + (0.53) |
| 3 | T2 M0 | 1 | 67 | + (0.51) |
| 4 | T2 M0 | 3 | 70 | − |
| 5 | T2 M0 | 3 | 59 | − |
| 6 | T2 M0 | 2 | 64 | + (0.49) |
| 7 | T2 M1 | 3 | 84 | − |
| 8 | T2 M1 | 3 | 83 | + (0.79) |
| 9 | T2 M1 | 3 | 71 | − |
| 10 | T2 M1 | 2 | 83 | − |
| 11 | T2 M1 | 2 | 78 | + (0.35) |
| 12 | T3 M0 | 3 | 65 | IS |
| 13 | T3 M0 | 3 | 67 | + (0.65) |
| 14 | T3 M0 | 2 | 79 | + (0.46) |
| 15 | T3 M0 | 2 | 83 | + (0.52) |
| 16 | T3 M0 | 2 | 72 | + (0.36) |
| 17 | T3 M1 | 2 | 76 | + (0.37) |
| 18 | T3 M1 | 3 | 73 | + (0.60) |
| 19 | T3 M1 | 2 | 73 | − |
| 20 | T3 M1 | 3 | 61 | − |
| 21 | T3 M1 | 1 | 80 | + (0.57) |
| 22 | T3 M1 | 2 | 64 | + (0.34) |
| 23 | T3 M1 | 3 | 71 | + (0.25) |
| 24 | T3 M1 | 1 | 65 | + (0.56) |
| 25 | T3 M1 | 2 | 68 | + (0.38) |
| 26 | T4 M0 | 3 | 72 | − |
| 27 | T4 M0 | 3 | 73 | + (0.54) |
| 28 | T4 M0 | 3 | 55 | − |
| 29 | T4 M0 | 3 | 78 | − |
| 30 | T4 M1 | 3 | 64 | + (0.34) |
| 31 | T4 M1 | 3 | 58 | + (0.58) |
| 32 | T4 M1 | 3 | 71 | + (0.36) |
| 33 | T4 M1 | 3 | 67 | − |
| 34 | T4 M1 | 3 | 67 | − |
| 35 | T4 M1 | 1 | 80 | − |
| 36 | T4 M1 | 2 | 75 | + (0.62) |
| 37 | T4 M1 | 3 | 66 | + (0.38) |

[a]Staging is based on digital rectal examination and bone scan (9).
[b]World Health Organization gradings: 1. Well differentiated. 2. Moderately differentiated. 3. Poorly differentiated. 4. Mixture of differentiation.
[c]+ = 10q loss − = no detected 10q loss.
IS = instability.
Figures in brackets give the average degree of signal reduction for microsatellite markers showing allele loss, as determined by fluorescence based typing.

TABLE 3

LOCUS     AA009519     510 bp     mRNA     EST 29-JUL-1996
DEFINITION ze82b09.r1 Homo sapiens cDNA clone
365465 5' similar to SW:TENS_CHICK Q04205 TENSIN. [1].
ACCESSION AA009519
NID     g1470718
KEYWORDS  EST.
SOURCE     human.
ORGANISM Homo sapiens
    Eukaryota; mitochondrial eukaryotes; Metazoa; Chordata; Vertebrata; Mammalia; Eutheria;
    Primates; Catarrhini; Hominidae; Homo.
REFERENCE   1 (bases 1 to 510)
AUTHORS    Hillier, L., Clark, N., Dubuque, T., Elliston, K., Hawkins, M.,
    Holman, M., Hultman, M., Kucaba, T., Le, M., Lennon, G., Marra, M.,
    Parsons, J., Rifkin, L., Rohlfing, T., Soares, M., Tan, F., Trevaskis, E.,

TABLE 3-continued

Waterston, R., Williamson, A., Wohldmann, P. and Wilson, R.
TITLE      Wash U-Merck EST Project
JOURNAL    Unpublished (1995)
COMMENT
    Contact: Wilson RK
    The WashU-Merck EST
    Washington University School of Medicine
    4444 Forest Park Parkway, Box 8501, St. Louis, MO 63108
    Tel: 314 286 1800
    Fax: 314 286 1810
    Email: est@watson.wustl.edu
    This clone is available royalty-free through LLNL; contact the
    IMAGE Consortium (info@image.llnl.gov) for further information.
    Insert Length: 1195 Std Error: 0.00
    Seq primer: mob.REGA+ET
    High quality sequence stop: 331.
FEATURES     Location/Qualifiers
source  1...510
    /organism="Homo sapiens"
    /note="Organ: heart; Vector: pT7T3D (Pharmacia) with a
    modified polylinker; Site_1: Not I; Site_2: Eco RI; 1st
    strance cDNA was primed with a Not I - oligo(dT) primer [5'
    TGTTACCAATCTCTGAAGTGGGAGCGGCCGCATCTTTTTTTTTTTTTTTTTT 3'],
    double-stranded cDNA was size selected, ligated to Eco RI
    adapter (Pharmacia), digested with Not I and cloned into
    the Not I and eco RI sites of a modified pT7T3 vector
    (Pharmacia). Library went through one round of
    normalization to a Cot = 5. Library was constructed by
    M. Fatima Bonaldo. This library was constructed from the
    same fetus as the fetal lung library, Soares fetal lung
    NbHL19W."
    /clone="365465"
    /clone_lib="Soares_fetal_heart_NbHH19W"
    /sex="unknown"
    /dev_="19 weeks"
    /lab_host="DH10B (ampicillin resistant)"
    mRNA <1...>510
BASE COUNT    162 a    92 c    108 g    143 t    5 others
ORIGIN      AA009519 Length: 510 September 10, 1996 19:03 Type: N Check: 3385..
        1 atgtagtaag gtttttggat tcaaagcata aaaaccatta caagatatac aatctttgtg
       61 ctgaaagaca ttatgacacc gccaaattta attgcagagt tgcacaatat ccttttgaag
      121 accataaccc accacagcta gaacttatca aacccttg tgaagatctt gaccaatggc
      181 taagtgaaga tgacaatcat gttgcagcaa ttcactgtaa agctggaaag ggacgaactg
      241 gtgtaatgat atgtgcatat ttattacatc ggggcaaatt tttaaaggca caagaggcc
      301 ctagatttct atggggaagt aaggaccaga gacaaaaagg gagtaactat ttcccagtca
      361 gaaggcgcta tgtgtattat tattagctac ctgtaaaga atcatctgga ttatagacca
      421 gtggcacgt tgtttcccaa gatgatgntt tgaaactatt nccaatgttc agtggcngga
      481 ccttgcaatc cncagttttgt gggtcctgcn
//

TABLE 4

LOCUS      AA009520    414 bp    mRNA    EST 01-FEB-1997
DEFINITION ze82b09.sl Soares_fetal_heart_NbHH19W Homo sapiens cDNA clone
    IMAGE:365465 3'.
    ACCESSION AA009520
    NID      g1470719
    KEYWORDS  EST.
    SOURCE     human.
    ORGANISM Homo sapiens
    Eukaryota; mitochondrial eukaryotes; Metazoa; Chordata; Vertebrata; Eutheria;
    Primates; Catarrhini; Hominidae; Homo.
REFERENCE   1 (bases 1 to 414)
AUTHORS   Hillier, L., Clark, N., Dubuque, T., Elliston, K., Hawkins, M.,
    Holman, M., Hultman, M., Kucaba, T., Le, M., Lennon, G., Marra, M.,
    Parsons, J., Rifkin, L., Rohlfing, T., Soares, M., Tan, F., Trevaskis, E.,
    Waterston, R., Williamson, A., Wohldmann, P. and Wilson, R.
TITLE      Wash U-Merck EST Project
JOURNAL    Unpublished (1995)
COMMENT
    Contact: Wilson RK
    The WashU-Merck EST
    Washington University School of Medicine
    4444 Forest Park Parkway, Box 8501, St. Louis, MO 63108
    Tel: 314 286 1800
    Fax: 314 286 1810

TABLE 4-continued

```
    Email: est@watson.wustl.edu
    This clone is available royalty-free through LLNL; contact the
    IMAGE Consortium (info@image.llnl.gov) for further information.
    Seq primer: mob.REGA+ET
    High quality sequence stop: 317.
FEATURES     Location/Qualifiers
source   1..414
    /organism="Homo sapiens"
    /note="Organ: heart; Vector: pT7T3D (Pharmacia) with a
    modified polylinker; Site_1: Not I; Site_2: Eco RI; 1st
    strance cDNA was primed with a Not I - oligo(dT) primer [5'
    TGTTACCAATCTCTGAAGTGGGAGCGGCCGCATCTTTTTTTTTTTTTTTTT 3'],
    double-stranded cDNA was size selected, ligated to Eco RI
    adapter (Pharmacia), digested with Not I and cloned into
    the Not I and eco RI sites of a modified pT7T3 vector
    (Pharmacia). Library went through one round of
    normalization to a Cot = 5. Library was constructed by
    M. Fatima Bonaldo. This library was constructed from the
    same fetus as the fetal lung library, Soares fetal lung
    NbHL19W."
    /clone="365465"
    /clone_lib="Soares_fetal_heart_NbHH19W"
    /sex="unknown"
    /dev_="19 weeks"
    /lab_host="DH10B (ampicillin resistant)"
    mRNA (<1..>414)
BASE COUNT     104 a     71 c     72 g     165 t     2 others
ORIGIN     AA009520 Length: 414 September 10, 1996 19:05 Type: N Check: 5376..
     1 cattttattc aagtttattt tcatggtgtt ttatccctct tgataaaaaa aaattcagac
    61 ttttgtaatt tgtgtatgct gatcttcatc aaaaggttca ttctctggat cagagtcagt
   121 ggtgtcagaa tatctataat gatcaggttc attgtcacta acatctggtg ttacagaagt
   181 tgaactgcta gcctctggat ttgacggctc ctctactgtt tttgtgaagt acagcttcac
   241 cttaaaattt ggagaaaagt atcggttggc tttgtctttta tttgctttgt caagatcatt
   301 ttttgttaa gtaagtacta gatattcctt gtcattatct gcacgctcta tactgcaaat
   361 gctatcgatt tcttgatcac atagacttc cattttcnac ttttcngag gttt
   421 gtggcacgt tgtttcccaa gatgatgntt tgaaactatt nccaatgttc agtggcngga
   481 ccttgcaatc cncagttttgt gggtcctgcn
//
```

TABLE 5

```
LOCUS     AA017563     241 bp     mRNA     EST 02-AUG-1996
DEFINITION  ze39e04.s1 Soares retina N2brHR Homo sapiens cDNA clone
     IMAGE:361374 3', mRNA sequence.
     ACCESSION AA017563
     NID     g1479716
     KEYWORDS  EST.
     SOURCE    human.
     ORGANISM Homo sapiens
     Eukaryota; mitochondrial eukaryotes; Metazoa; Chordata; Vertebrata; Eutheria;
     Primates; Catarrhini; Hominidae; Homo.
REFERENCE  1 (bases 1 to 241)
AUTHORS    Hillier, L., Clark, N., Dubuque, T., Elliston, K., Hawkins, M.,
     Holman, M., Hultman, M., Kucaba, T., Le, M., Lennon, G., Marra, M.,
     Parsons, J., Rifkin, L., Rohlfing, T., Soares, M., Tan, F.,
     Trevaskis, E., Waterston, R., Williamson, A., Wohldmann, P. and
     Wilson, R.
TITLE      Wash U-Merck EST Project
JOURNAL    Unpublished (1995)
COMMENT
     Contact: Wilson RK
     The WashU-Merck EST
     Washington University School of Medicine
     4444 Forest Park Parkway, Box 8501, St. Louis, MO 63108
     Tel: 314 286 1800
     Fax: 314 286 1810
     Email: est@watson.wustl.edu
     This clone is available royalty-free through LLNL; contact the
     IMAGE Consortium (info@image.llnl.gov) for further information.
     Seq primer: -40M13 fwd. from Amersham
     High quality sequence stop: 166.
FEATURES     Location/Qualifiers
source   1..241
    /organism="Homo sapiens"
    /note="Organ: eye; Vector: pT7T3D (Pharmacia) with a
    modified polylinker; Site_1: Not I; Site_2: Eco RI; 1st
```

TABLE 5-continued strance cDNA was primed with a Not I - oligo(dT) primer [5'
TGTTACCAATCTCTGAAGTGGGAGCGGCCGCATCTTTTTTTTTTTTTTTT 3'],
double-stranded cDNA was size selected, ligated to Eco RI
adapter (Pharmacia), digested with Not I and cloned into
the Not I and eco RI sites of a modified pT7T3 vector
(Pharmacia). The retinas were obtained from a 55 year old
Caucasian and total cellular poly(A)+RNA was extracted 6
hrs after their removal. The retina RNA was kindly
provided by Roderick N. McInnes M.D. Ph.D. from the
University of Toronto. Library constructed by Bento
Soares M. Fatima Bonaldo."
/clone="361374"
/clone_lib="Soares retina N2brHR"
/sex="male"
/tisue_type="retina"
/dev_="55 year old"
/lab_host="DH10B (ampicillin resistant)"
mRNA (<1..>241)
BASE COUNT    31 a    84 c    82 g    37 t    7 others
ORIGIN    AA017563 Length: 241 September 10, 1996 19:12 Type: N Check: 7697..
    1 gcggccgcgg nggntgcagc tccangnagg gggtctgagt cgcctgtcac catttncagg
   61 gctgggaacg ccggagagtt ggtctctccc cttctactgc ctccaacacg gcggcngcgg
  121 cggcggcaca tccagggacc cgggccggtt ttaaacctcc cgtccgccgc cgccgcaccc
  181 cccagtggcc cgggctccgg agnccgcctg gcggaggcaa gccgttcgga gggattattc
  241 g
//

TABLE 6

LOCUS    C01084    84 bp    DNA    EST 11-JUL-1996
DEFINITION HUMGS0007741 Human Gene Signature, 3'-directed cDNA,
   sequence.
   ACCESSION C01084
   NID    g1433314
   KEYWORDS Gene Signature: GS; EST (expressed sequence tag); Body Map; gene expression.
   SOURCE    One or more human adult tissue.
   ORGANISM Homo sapiens
   Eukaryota; mitochondrial eukaryotes; Metazoa; Chordata; Vertebrata; Eutheria;
   Primates; Catarrhini; Hominidae; Homo.
REFERENCE    1 (bases 1 to 84)
AUTHORS    Okubo, K.
TITLE    Direct Submission
JOURNAL    Submitted (28-DEC-1995) to the DDBJ/EMBL/GenBank databases.
   Kousaku Okubo, Osaka University
   Institute for Molecular and Cellular Biol;
   1-3, yamada-oka, Suita, Osaka Pref. 565, Japan
   Tel: 06-077-5111(ex.3315)
   Fex: 06-877-1922
   Email: kousaku@imcb.osaka-u.ac.jp
   REFERENCE 2 (bases 1 to 84)
   AUTHORS Okubo, K
   TITLE body Map; human gene expression data base
   JOURNAL Unpublished (1995)
   COMMENT We are not submitting the same cDNA sequence redundantly
   to DDBJ since 1993. For the abundance information of clones with this
   sequence in this library and as well as in other 3'-directed libraries, see '
   http://www.imcb.osaka-u.ac.jp/bodymap.' The sequences of the clones
   represented by this GS sequences is also found there.
FEATURES    Location/Qualifiers
source    1..84
   /organism="Homo sapiens"
BASE COUNT    38 a    12 c    11 g    22 t    1 others
ORIGIN    C01084 Length: 84 September 10, 1996 19:12 Type: N Check: 5876..
    1 gatcagcata cacaaatnac aaaagtctga attttttttt atcaagaggg ataaaacacc
   61 atgaaaataa acttgaataa actg
//

TABLE 7-1

LOCUS    H92038    427 bp    mRNA    EST    29-NOV-1995
DEFINITION ys82e12.rl Homo sapiens cDNA clone
   221326 5'.
ACCESSION    H92038
NID    g1087616

TABLE 7-1-continued

```
KEYWORDS    EST.
SOURCE      human clone=221326 primer=M13RP1 library=Soares retina N264HR
            vector=pT7T3D (Pharmacia) with a modified polylinker host=DH10B
            (ampicillin resistant) Rsite 1=Not I Rsite 2=Eco RI 1st
            strand cDNA was primed with a Not I - oligo(dT) primer [5'
            TGTTACCAATCTGAAGTGGGAGCGGCCGCGCTTTTTTTTTTTTTTTTTT 3'],
            double-stranded cDNA was size selected, ligated to Eco RI
            adapters (Pharmacia), digested with Not I and cloned into
            the Not I and Eco RI sites of a modified pT7T3 vector
            (Pharmacia). The retinas were obtained from a 55 year old
            Caucasian and total cellular poly(A)+ RNA was extracted 6
            hrs after their removal. The retina RNA was kindly
            provided by Roderick R. McInnes M.D. Ph.D. from the
            University of Toronto Library constructed by Bento
            Soares and M. Fatima Bonaldo.
ORGANISM    Homo sapiens
            Eukaryota; Metazoa; Eumetazoa; Bilateria; Coelomata; Deuterostomia; Chordata;
            Vertebrata; Gnathostomata; Osteichthyes; Sarcopterygii; Choanata; Tetrapoda;
            Amniota; Eutheria; Archonata; Primates; Catarrhini; Hominidae; Homo.
            REFERENCE   1 (bases to 427)
            AUTHORS     Hillier, L., Clark, N., Dubuque, T., Elliston, K., Hawkins, M.,
            Holman, M., Hultman, M., Kucaba, T., Le, M., Lennon, G., Marra, M.,
            Parsons, J., Rifkin, L., Rohlfing, T., Soares, M., Tan, F.,
            Trevaskis, E., Waterston, R., Williamson, A., Wohldmann, P. and
            Wilson, R.
TITLE       The WashU-Merck EST Project
JOURNAL     Unpublished (1995)
COMMENT
            Contact: Wilson RK
            WashU-Merck EST Project
            Washington University School of Medicine
            4444 Forest Park Parkway, Box 8501, St. Louis, MO 63108
            Tel: 314 286 1800
            Fax: 314 286 1810
            Email: est@watson.wustl.edu
            High quality sequence stops: 330
            Source: IMAGE Consortium, LLNL
            This clone is available royalty-free through LLNL ; contact the
            IMAGE Consortium (info#image.llnl.gov) for further information.
FEATURES        Location/Qualifiers
source      1..427
            /organism="Homo sapiens"
            mRNA <1..>427
BASE COUNT      103 a     75 c     116 g     129 t     4 others
ORIGIN   H92038 Length: 427 september 10, 1996 19:06 Type: N Check: 6168..
        1 ggaagtnggt natggtcttc aaaaggatat tgtgcaactc tgcaattaaa ttggcggtg
       61 tcataatgtc tttcagcaca aagattgtat atcttgtaat ggttatg ctttgaatcc
      121 aaaaacctta ctacatcatc aatattgttc ctgtatacgc cttcaagtct ttctgcagga
      181 aatcccatag caataatgtt tggataaata taggtcaagt ctaagtcgaa tccatcctct
      241 tgatatctcc ttttgtttct ggctaacgat ctctttggat ggatggctgt catgtctggg
      301 gagcctgtgn tggnaaggaa aaagggaggg agagagatgg gcagaagctg gctcggtggg
      361 cgggggcttt cttctggcag ggatgggaaa tgggctctgg ggactgggcg gtactggatg
      421 gcccctc
//
```

TABLE 8

```
LOCUS       H92039    117 bp    mRNA    EST    29-NOV-1995
DEFINITION  ys82e12.s1 Homo sapiens cDNA clone
            221326 3'.
ACCESSION   H92039
NID         g1087617
KEYWORDS    EST.
SOURCE      human clone=221326 primer=Promega -21m13 library=Soares retina N2b4H
            vector=pT7T3D (Pharmacia) with a modified polylinker host=DH10B (ampicillian
            resistant) Rsite 1=Not I Rsite 2=Eco RI 1st strand cDNA was primed with NOT I -
            oligo(dT) primer
            TGTTACCAATCTGAAGTGGGAGCGGCCGCGCTTTTTTTTTTTTTTTTTT 3'],
            double-stranded cDNA was size selected, ligated to Eco RI
            adapters (Pharmacia), digested with Not I and cloned into
            the Not I and Eco RI sites of a modified pT7T3 vector
            (Pharmacia). The retinas were obtained from a 55 year old
            Caucasian and total cellular poly(A)+ RNA was extracted 6
            hrs after their removal. The retina RNA was kindly
            provided by Roderick R. McInnes M.D. Ph.D. from the
            University of Toronto. Library constructed by Bento
```

TABLE 8-continued

Soares and M. Fatima Bonaldo.
ORGANISM  Homo sapiens
   Eukaryota; Metazoa; Eumetazoa; Bilateria; Coelomata; Deuterostomia; Chordata;
   Vertebrata; Gnathostomata; Osteichthyes; Sarcopterygii; Choanata; Tetrapoda;
   Amniota; Theria; Eutheria; Primates; Catarrhini; Hominidae; Homo.
REFERENCE  1 (bases 1 to 117)
AUTHORS   Hillier, L., Clark, N., Dubuque, T., Elliston, K., Hawkins, M.,
   Holman, M., Hultman, M., Kucaba, T., Le, M., Lennon, G., Marra, M.,
   Parsons, J., Rifkin, L., Rohlfing, T., Soares, M., Tan, F.,
   Trevaskis, E., Waterston, R., Williamson, A., Wohldmann, P. and
   Wilson, R.
TITLE    The WashU-Merck EST Project
JOURNAL  Unpublished (1995)
COMMENT
   Contact: Wilson RK
   WashU-Merck EST Project
   Washington University School of Medicine
   4444 Forest Park Parkway, Box 8501, St. Louis, MO 63108
   Tel: 314 286 1800
   Fax: 314 286 1810
   Email: est@watson.wustl.edu
   High quality sequence stops: 104
   Source: IMAGE Consortium, LLNL
   This clone is available royalty-free through LLNL ; contact the
   IMAGE Consortium (info@image.llnl.gov) for further information.
   Possible reversed clone: polyT not found
FEATURES   Location/Qualifiers
source   1..117
   /organism="Homo sapiens"
   mRNA <1..>117
   BASE COUNT   16a   44c   37g   19t   1 others
ORIGIN  H92039 Length 117 September 10, 1996 19:12 Type: N Check: 5577..
   1 tccagggctg ggaacgccgg agagttggtc tctccccttc tactgcctcn aacacggcgg
  61 cggcggcggc ggcacatcca gggacccggg ccggttttaa acctcccgtc cgccgcc
//

TABLE 9

LOCUS   N20238   322 bp   mRNA   EST   18-DEC-1995
DEFINITION  yx44F06.s1 Homo sapiens cDNA clone
   264611 3'.
ACCESSION   N20238
NID   g1125193
KEYWORDS   EST.
SOURCE   human clone=26411 primer=m13 −40 forward library=Soares melanocyte 2NbHM
      vector=pT7T3D (Pharmacia) with a modified polylinker host=DH10B (ampicillin
      resistant) Rsite1=Not I Rsite2=Eco RI Male.
      1st strand cDNA was primed with a Not I - oligo(dT) primer [5'
      TGTTACCAATCTGAAGTGGGAGCGGCCGCAGTTTTTTTTTTTTTTTTTT3'],
      double-stranded cDNA was size selected, ligated to Eco RI
      adapters (Pharmacia), digested with Not I and cloned into
      the Not I and Eco RI sites of a modified pT7T3 vector
      (Pharmacia). Library constructed by Bento Soares and
      M. Fatima Bonaldo. RNA from normal foreskin melanocytes
      (FS374) was kindly provided by Dr. Anthony P. Albino.
ORGANISM  Homo sapiens
   Eukaryota; Metazoa; Eumetazoa; Bilateria; Coelomata; Deuterostomia; Chordata;
   Vertebrata; Gnathostomata; Osteichthyes; Sarcopterygii; Choanata; Tetrapoda;
   Amniota; Mammalia; Theria; Eutheria; Primates; Catarrhini; Hominidae; Homo.
REFERENCE   1 (bases 1 to 322)
AUTHORS  Hillier, L., Clark, N., Dubuque, T., Elliston, K., Hawkins, M.,
Holman, M., Hultman, M., Kucaba, T., Le, M., Lennon, G., Marra, M.,
Parsons, J., Rifkin, L., Rohlfing, T., Soares, M., Tan, F.,
Trevaskis, E., Waterston, R., Williamson, A., Wohldmann, P. and
Wilson, R.
TITLE    the WashU-Merck EST Project
COMMENT
   Contact: Wilson RK
   WashU-Merck EST Project
   Washington University School of Medicine
   4444 Forest Park Parkway, Box 8501, St. Louis, MO 63108
   Tel: 314 286 1800
   Fax: 314 286 1810
   Email: est@watson.wustl.edu
   High quality sequence stops: 209
   Source: IMAGE Consortium, LLNL

TABLE 9-continued

This clone is available royalty-free through LLNL ; contact the
IMAGE Consortium (info@image.llnl.gov) for further information.
Possible reversed clone: polyT not found
FEATURES      Location/Qualifiers
source     1..322
          /organism="Homo sapiens"
          mRNA <1..>322
BASE COUNT      49 a      112 c      98 g      57 t      6 others
ORIGIN      N20238 Length: 322 September 10, 1996 19:07 Type: N Check: 7249..
   1 ggtctgagtc gcctgtcacc atttccaggg ctgggaacgc nggagagttg gtctctcccc
  61 ttctactgcc tccaacacgg cggcggcggc ggcggcacat ccagggaccc gggccggttt
 121 taaacctccc gtccgccgcc gccgcacccc ccgtggcccg ggctccggag gccgccggcg
 181 gagnaagccg tttcggagga ttattcgtct tctccccatt ccgctgccgc ccgctgccag
 241 gctcttggtg cttgaagaag aagcaggcca gttgnctgaa accattcnag aagccgcnga
 301 agcagccatt acncggctgc gg
//

TABLE 10

LOCUS    N29304      427 bp    mRNA    EST    04-JAN-1996
DEFINITION      yx44f06.r1 Homo sapiens cDNA clone
          264611 5'.
     ACCESSION    N29304
     NID      g1147540
     KEYWORDS    EST.
SOURCE   human clone 264611 Primer=T7 library=Soares melanocyte 2NbHM
          vector=pTyT3D (Pharmacia) with a modified polylinker host=DH10B
          (ampicillin resistant) Rsite1 =Not I Rsite2=Eco RI Male
          1st strand cDNA was primed with a Not I - oligo(dT) primer [5'
          TGTTACCAATCTGAAGTGGGAGCGGCCGCAGTTTTTTTTTTTTTTTTTTT 3'],
          double-stranded cDNA was size selected, ligated to Eco RI
          adapters (Pharmacia), digested with Not I and cloned into
          the Not I and Eco RI sites of a modified pT7T3 vector
          (Pharmacia). Library constructed by Bento Soares and
          M. Fatima Bonaldo. RNA from normal foreskin melanocytes
          (FS374) was kindly provided by Dr. Anthony P. Albino.
ORGANISM Homo sapiens
     Eukaryota; Metazoa; Eumetazoa; Bilateria; Coelomata; Deuterostomia; Chordata;
     Vertebrata; Gnathostomata; Osteichthyes; Sarcopterygii; Choanata; Tetrapoda;
     Amniota; Mammalia; Theria; Eutheria; Primates; Catarrhini; Hominidae; Homo.
REFERENCE      1 (bases to 427)
AUTHORS   Hillier, L., Clark, N., Dubuque, T., Elliston, K., Hawkins, M.,
Holman, M., Hultman, M., Kucaba, T., Le, M., Lennon, G., Marra, M.,
Parsons, J., Rifkin, L., Rohlfing, T., Soares, M., Tan, F.,
Trevaskis, E., Waterston, R., Williamson, A., Wohldmann, P. and
Wilson, R.
TITLE     The WashU-Merck EST Project
JOURNAL      Unpublished (1995)
COMMENT
     Contact: Wilson RK
     WashU-Merck EST Project
     Washington University School of Medicine
     4444 Forest Park Parkway, Box 8501, St. Louis, MO 63108
     Tel: 314 286 1800
     Fax: 314 286 1810
     Email: est@watson.wustl.edu
     High quality sequence stops: 370
     Source: IMAGE Consortium, LLNL
     This clone is available royalty-free through LLNL ; contact the
     IMAGE Consortium (info@image.llnl.gov) for further information.
FEATURES      Locatiom/Qualifiers
source     1..427
          mRNA <1..>427
BASE COUNT      116a      90c      79g      140t      2 others
ORIGIN      N29304 Length: 427 September 10, 1996 19:04 Type: N Check: 9508..
       taagtactag atattccttg tcattatctg cactgctctat actgcaaatg ctatcgattt
    61 cttgatcaca tagacttcca ttttctactt tttctgaggt ttcctctggt cctggtatga
   121 agaatgtatt tacccaaaag tgaaacattt tgtccttttt tagcatcttg ttctgtttgt
   181 ggaagaactc tactttgata tcaccacaca caggtaacgg ctgagggaac tcaaagtaca
   241 tgaacttgtc ttcccgtcgt gtgggtcctg aattggagga atatatcttc acctttagct
   301 ggcagaccac aaactgnagg attgcaagtt ccgccactga acattggaat agtttcaaac
   361 atcatcttgt gaaacaacag tgccactggt ctataaccca gatgattctt taacagggta
   421 gctataa
//

TABLE 11

```
LOCUS       N35389     437 bp     mRNA      EST      16-JAN-1996
DEFINITION  yy23e03.sl Homo sapiens cDNA clone
            272092 3'.
ACCESSION   N35389
NID         g1156531
KEYWORDS    EST.
SOURCE      human clone=272092 primer=m13 -40 forward library=Soares melanocyte
            2NbHM vector=pT7T3D (Pharmacia) with a modified polylinker
            host=DH10B (ampicillin resistant) Rsite1 =Not I Rsite2=Eco RI Male
            1st strand cDNA was primed with a Not I - oligo(dT) primer [5'
            TGTTACCAATCTGAAGTGGGAGCGGCCGCAGTTTTTTTTTTTTTTTTT3'],
            double-stranded cDNA was size selected, ligated to Eco RI
            adapters (Pharmacia), digested with Not I and cloned into
            the Not I and Eco RI sites of a modified pT7T3 vector
            (Pharmacia). Library constructed by Bento Soares and
            M. Fatima Bonaldo. RNA from normal foreskin melanocytes
            (FS374) was kindly provided by Dr. Anthony P. Albino.
ORGANISM    Homo sapiens
            Eukaryota; Metazoa; Eumetazoa; Bilateria; Coelomata; Deuterostomia; Chordata;
            Vertebrata; Mammalia; Theria; Eutheria; Gnatbostomata; Osteichthyes; Sarcopterygii,
            Choanata; Tetrapoda; Amniota; Primates; Catarrhini; Hominidae; Homo.
REFERENCE   1 (bases 1 to 437)
AUTHORS     Hillier, L., Clark, N., Dubuque, T., Elliston, K., Hawkins, M.,
            Holman, M., Hultman, M., Kucaba, T., Le, M., Lennon, G., Marra, M.,
            Parsons, J., Rifkin, L., Rohlfing, T., Soares, M., Tan, F.,
            Trevaskis, E., Waterston, R., Williamson, A., Wohldmann, P. and
            Wilson, R.
TITLE       The WashU-Merck EST Project
JOURNAL     Unpublished (1995)
COMMENT
            Contact: Wilson RK
            WashU-Merck EST Project
            Washington University School of Medicine
            4444 Forest Park Parkway, Box 8501, St. Louis, MO 63108
            Tel: 314 286 1800
            Fax: 314 286 1810
            Email: est@watson.wustl.edu
            High quality sequence stops: 311
            Source: IMAGE Consortium, LLNL
            This clone is available royalty-free through LLNL ; contact the
            IMAGE Consortium (info@image.llnl.gov) for further information.
FEATURES    Location/Qualifiers
source      1..437
            /organism="Homo sapiens"
            mRNA <1..>437
BASE COUNT     108a     79c     78g     166t     6 others
ORIGIN      N35389 Length: 437 September 10, 1996 19:04 Type: N Check: 9803..
        1 cagtttattc aagtttattt tcatggtgtt ttatccctct tgataaaaaa aaattcagac
       61 ttttgtaatt tgtgtatgct gatcttcatc aaaaggttca ttctctggat cagagtcagt
      121 ggtgtcagaa tatctataat gatcaggttc attgtcacta acatctggtg ttacagaagt
      181 tgaactgcta gcctctggat ttgacggctc ctctactgtt tmgtgaagt acagcttcac
      241 cttaaaattt ggagaaaagt atcggttggc tttgtcttta tttgcnttgt caagatcatt
      301 ttctgttaaa gtaagtacta tgatattcct tgtcattatc tgcacgctct atactgcaaa
      361 tgctatcgat ttcttgatca catagacttc cattttctac tttttcngag gtttcccccn
      421 ggtccngggt aatgaan
//
```

TABLE 12

```
LOCUS       N48030     372 bp     mRNA      EST      14-FEB-1996
DEFINITION  yy23e03.rl Homo sapiens cDNA clone
            272092 5' similar to SW:TENS_CHICK Q04205 TENSIN. [1].
ACCESSION   N48030
NID         g1189196
KEYWORDS    EST.
SOURCE      human clone=272092 primer=T7 library=Soares melanocyte 2NbHM vector=pT7T3D
            (Pharmacia) with a modified polylincker host=DH10B (ampicillin resistant) Rsite1=Not I
            Rsite2=Eco RI Male 1st strand cDNA was primed with a Not I - oligo(dT) primer [5'
            TGTTACCAATCTGAAGTGGGAGCGGCCGCAGTTTTTTTTTTTTTTTTTT 3'],
            double-stranded cDNA was size selected, ligated to Eco RI
            adapters (Pharmacia), digested with Not I and cloned into
            the Not I and Eco RI sites of a modified pT7T3 vector
            (Pharmacia). Library constructed by Bento Soares and
            M. Fatima Bonaldo. RNA from normal foreskin melanocytes
            (FS374) was kindly provided by Dr. Anthony P. Albino.
ORGANISM    Homo sapiens
```

TABLE 12-continued

```
    Eukaryota; Metazoa; Eumetazoa; Bilateria; Coelomata; Deuterostomia; Chordata;
    Vertebrata; Mammalia; Theria; Eutheria; Gnathostomata; Osteichthyes; Sarcopterygii;
    Choanata; Tetrapoda; Archonta; Primates; Catarrhini; Hominidae; Homo.
REFERENCE    (bases to 372)
AUTHORS   Hillier, L., Clark, N., Dubuque, T., Elliston, K., Hawkins, M.,
    Holman, M., Hultman, M., Kucaba, T., Le, M., Lennon, G., Marra, M.,
    Parsons, J., Rifkin, L., Rohlfing, T., Soares, M., Tan, F.,
    Trevaskis, E., Waterston, R., Williamson, A., Wohldmann, P. and
    Wilson, R.
TITLE    The WashU-Merck EST Project
JOURNAL    Unpublished (1995)
COMMENT
    Contact: Wilson RK
    WashU-Merck EST Project
    Washington University School of Medicine
    4444 Forest Park Parkway, Box 8501, St. Louis, MO 63108
    Tel: 314 286 1800
    Fax: 314 286 1810
    Email: est@watson.wustl.edu
    High quality sequence stop: 240.
    This clone is available royalty-free through LLNL ; contact the
    IMAGE Consortium (info@image.llnl.gov) for further information.
FEATURES    Location/Qualifiers
source    1..372
        /organism="Homo sapiens"
        mRNA <1..>372
        /clone=
BASE COUNT    122 a    67 c    76 g    101 t    6 others
ORIGIN   N48030 Length: 372 September 10, 1996 19:06 Type: N Check: 6071
      1 tttttggatt caaagcataa aaaccattac aagatatttt atcttctnng ctgaaagaca
     61 ttatgacacc gccaaattta angcagagt tgcacaatat ccttttgaag accataaccc
    121 accacagcta gaacttatca aaccctttg tgaagatctt gaccaatggc taagtgaaga
    181 tgacaatcat gttgcagcaa ttcactgtaa agctggaaag ggacgaactg gtgtaatgat
    241 atgtgcatat ttattacatc ggggcaaatt tttaaaggca caagaggccc naagatttct
    301 atggggaagt aagggcccga gacnaaaagg gngtaactat tcccagtcag agggcgctat
    361 gtgtnttatt at
//
```

TABLE 13

```
LOCUS    R06763    474 bp    mRNA    EST    03-APR-1995
DEFINITION yf11e03.s1 Homo sapiens cDNA clone
    126556 3'.
ACCESSION    R06763
NID    g757383
KEYWORDS    EST.
SOURCE   human clone=126556 library=Soares fetal liver spleen 1NFLS
        vector=pT7T3D (Pharmacia) with a modified polylinker host=DH10B
        (ampicillin resistant) primer=SP6 Rsite1=Pac I Rsite2=Eco RI Liver
        and spleen from a 20 week-post conception male fetus. 1st strand cDNA
        was primed with a Pac I - oligo(dT) primer
        [5' AACTGGAAGAATTAATTAAAGATCTTTTTTTTTTTTTTTTTT 3'],
        double-stranded cDNA was ligated to Eco RI adaptors
        (Pharmacia), digested with Pac I and cloned into the Pac I
        and Eco RI sites of the modified pT7T3 vector. Library
        went through one round of normalization. Library
        constructed by Bento Soares and M. Fatima Bonaldo.
ORGANISM Homo sapiens
    Eukaryota; Metazoa; Chordata; Vertebrata; Gnathostomata; Mammalia; Eutheria;
    Primates; Catarrhini; Hominidae; Homo.
REFERENCE    1 (bases 1 to 474)
AUTHORS   Hillier, L., Clark, N., Dubuque, T., Elliston, K., Hawkins, M.,
    Holman, M., Hultman, M., Kucaba, T., Le, M., Lennon, G., Marra, M.,
    Parsons, J., Rifkin, L., Rohlfing, T., Soares, M., Tan, F.,
    Trevaskis, E., Waterston, R., Williamson, A., Wohldmann, P. and
    Wilson, R.
TITLE    The WashU-Merck EST Project
JOURNAL    Unpublished (1995)
COMMENT
    Contact: Wilson RK
    WashU-Merck EST Project
    Washington University School of Medicine
    4444 Forest Park Parkway, Box 8501, St. Louis, MO 63108
    Tel: 314 286 1800
    Fax: 314 286 1810
    Email: est@watson.wustl.edu
```

TABLE 13-continued

```
      High quality sequence stop: 240.
      This clone is available royalty-free through LLNL ; contact the
      IMAGE Consortium (info@image.llnl.gov) for further information.
FEATURES     Location/Qualifiers
source      1. .474
         /organism="Homo sapiens"
         /clone="126556"
BASE COUNT       108 a     81 c     89 g     190 t     6 others
ORIGIN R06763 Length: 474 September 10, 1996 19:04 Type: N Check: 6789..
        1 agccgcttta attaaagatc tttttttttt tttttttc agtttattca agtttatttt
       61 catggtgttt tatccctctt gataaaaaaa aattcagact tttgtaattt gtgtatgctg
      121 atcttcatca aaagggttca ttctctggat cagagtcagt gggtgtcaga atatctataa
      181 tgatcaggtt cattgtcact aacatctggn gtiacagaag ttgaactgct agcctctggg
      241 atttgacggc tccnctactg tttttgtgaa gtacagcttc accttaaaat ttggngaaaa
      301 gtatcggttg gctttgtctt tatttgcttt gtcaagatca tttttgtta aagtaaggac
      361 taggatattc cctgtcatta tctgcacgct ctatactgca aatgctatcg atttcttgat
      421 cacatagggc ttccntttc tactttttct gagggttncc ctggtccggg nttg
//
```

TABLE 14

```
LOCUS       R06814      429 bp    mRNA      EST       03-APR-1995
DEFINITION   yfl11e03.rl Homo sapiens cDNA clone
126556 5'.
ACCESSION     R06814
NID      g757434
KEYWORDS      EST.
SOURCE    human clone=126556 library=Soares fetal liver spleen 1NFLS
            vector=pT7T3D (Pharmacia) with a modified polylinker host=DH10B
            (ampicillin resistant) primer=M13RP1 Rsite1=Pac I Rsite2=Eco RI
            Liver and spleen from a 20 week-post conception male fetus.
            1st strand cDNA was primed with a Pac I - oligo(dT) primer
            [5' AACTGGAAGAATTAATTAAAGATCTTTTTTTTTTTTTTTT 3'],
            double-stranded cDNA was ligated to Eco RI adaptors
            (Pharmacia), digested with Pac I and cloned into the Pac I
            and Eco RI sites of the modified pT7T3 vector. Library
            went through one round of normalization. Library
            constructed by Bento Soares and M. Fatima Bonaldo.
ORGANISM Homo sapiens
      Eukaryota; Metazoa; Chordata; Vertebrata; Gnathostomata; Mammalia; Eutheria;
      Primates; Catarrhini; Hominidae; Homo.
REFERENCE     1 (bases 1 to 429)
AUTHORS    Hillier, L., Clark, N., Dubuque, T., Elliston, K., Hawkins, M.,
      Holman, M., Hultman, M., Kucaba, T., Le, M., Lennon, G., Marra, M.,
      Parsons, J., Rifkin, L., Rohlfing, T., Soares, M., Tan, F.,
      Trevaskis, E., Waterston, R., Williamson, A., Wohldmann, P. and
      Wilson, R.
TITLE    The WashU-Merck EST Project
JOURNAL      Unpublished (1995)
COMMENT
      Contact: Wilson RK
      WashU-Merck EST Project
      Washington University School of Medicine
      4444 Forest Park Parkway, Box 8501, St. Louis, MO 63108
      Tel: 314 286 1800
      Fax: 314 286 1810
      Email: est@watson.wustl.edu
      High quality sequence stop: 240.
      This clone is available royalty-free through LLNL ; contact the
      IMAGE Consortium (info@image.llnl.gov) for further information.
FEATURES     Location/Qualifiers
source      1..429
         /organism="Homo sapiens"
         /clone="126556"
BASE COUNT       114 a     73 c     65 g     176 t     1 others
ORIGIN     R06814 Length: 429 September 10, 1996 19:16 Type: N Check: 889..
        1 tgttctgtaa gttactttta ccgttaaact tcttaatgu gcttattgtt tgtcttacat
       61 ttttaggttg gattttttctt aagtcacatg tctaataaaa aaaaccctta aatacctcat
      121 ttattcgtct tcgttagtga atgcattgtt gtacatatta gatttttctc tttagataac
      181 tcagcttccc ctattaagtg ccacatgtat tacaaaattt tatttatgtt ttattgttta
      241 ataaactctt gagaactaga tacattttaa tcamgtaa tacttacatt ttctaaaaca
      301 cttcattttt cccgggggttc ttcaacaaag gggatggcat gtaggtacaa gggatagctt
      361 taccngtgtt aggaaggttg tttttcacacc tttcatcaa ctgcatagtc ccgttttgt
      421 tggggccca
//
```

TABLE 15

```
LOCUS       R29457      224 bp    mRNA     EST      25-APR-1995
DEFINITION  FI-578D 22 week old human fetal liver cDNA library Homo sapiens
    cDNA clone F1-578D 5'.
ACCESSION      R29457
NID     g1511865
KEYWORDS       EST.
SOURCE    human.
ORGANISM Homo sapiens
    Eukaryota; mitochondrial eukaryotes; Metazoa; Chordata; Vertebrata; Mammalia; Eutheria;
    Primates; Catarrhini; Hominidae; Homo.
REFERENCE     1 (bases 1 to 224)
AUTHORS     Choi, S. S., Yun, J. W., Choi, E. K., Cho, Y. G., Sung, Y. C. and Shin, H. -S.
TITLE     Construction of a gene expression profile of a human fetal liver by
    single-pass cDNA sequencing
JOURNAL    Unpublished (1995)
COMMENT
    Contact: Hee-Sup Shin
    Developmental Genetics
    Pohang Institute of Science & Technology
    San31, Hyojadong Pohang, 790–784 Republic of Korea
    Tel: 562-279-2291
    Fax: 562-279-2199
    Email: shinhs@vision.postech.ac.kr
    Seq primer: T3 primer.
FEATURES    Location/Qualifiers
source     1..224
        /organism"Homo sapiens"
        /note="Vector: pBluescriptII SK(-); Site__1: EcoRI; Site__2:
        XhoI; The cDNA library made by oligo-dT primed and
        directionally cloned between 5'ExoR 1-Xhol3' sites."
        /clone="F1 -578D"
        /clone__lib="22 week old human fetal liver cDNA library"
        /lab__host="XL1-blue MRF"
        mRNA <1..>224
BASE COUNT      45a      78c      67g      34t
ORIGIN R29457 Length: 224 September 10, 1996 19:11 Type: N Check: 1046..
      1 gggctccgga gccgccggcg gaggcagccg ttcggaggat tattcgtctt ctccccattc
     61 cgctgccgcc gctgccaggc ctctgctgct gaggagaagc aggcccagtc gctgcaacca
    121 tccagcagcc gccgcagcag ccattacccg gctgcggtcc agagccaaga cgcagagagg
    181 gcatcagcta ccgccaagtc agagcatttc catctcagaa gaag
//
```

TABLE 16

```
LOCUS      T05157      266 bp    mRNA     EST      30-JUN-1993
DEFINITION  E5T03045 Homo sapiens cDNA
    clone HFBCS42.
ACCESSION      T05157
NID     g316309
KEYWORDS       EST.
SOURCE   human clone=HFBCS42 library=Fetal brain, Stratagene (cat#936206)
           vector=Lambda ZAP-II primer=M13-21 17–18 wk gestation, female;
           oligo-dT+ random primed cDNA synthesis; lambda ZAP-II vector,
           10 kb average insert size.
ORGANISM Homo sapiens
    Eukaryota; Animalia; Chordata; Vertebrata; Gnathostomata; Mammalia; Theria;
    Eutheria; Primates; Haplorhini; Catarrhini; Hominidae.
REFERENCE     1 (bases 1 to 266)
AUTHORS     Adams, M. D., Kerlavage, A. R., Fields, C. and Venter, J. C.
TITLE     3,400 expressed sequence tags identical diversity of transcripts
    from human brain
JOURNAL     Nature Genet. 4, 256–267 (1993)
COMMENT
    Contact: Adams, MD
    The Institute for Genomic Research
    932 Clopper Road, Gaithersburg, MD 20878
    Tel: 3018699056
    Fax: 3018699423
    Email: mdadams@tigr.org
FEATURES    Location/Qualifiers
source     1..266
        /organism="Homo sapiens"
        /clone=""HFBS42"
BASE COUNT      95 a     44 c     57 g     69 t     1 others
ORIGIN     T05157 Length: 266 September 10, 1996 19:06 Type: N Check: 4396
      1 tggagggaag acaagttcat gtactttgag ttccctcagc cgttacctgt gtgtggtgat
```

TABLE 16-continued

```
 61 atcaaagtag agttcttcca caaacagaac aagatgctaa aaaaggacaa aatgtttcac
121 ttttgggtaa atacattctt cataccagga ccagaggaaa cctcagaaaa agtagaaaat
181 ggaagtctat gtgatcaagn aatcgatagc atttgcagta tagagcgtgc agataatgac
241 aaggaatatc tagtacttac tttaac
//
```

TABLE 17

LOCUS    T60214    396 bp    mRNA    EST    09-FEB-1995
DEFINITION yc22c07.r1 Homo sapiens cDNA clone
    81420 5'.
ACCESSION  T60214
NID    g662051
KEYWORDS  EST.
SOURCE  human clone=81420 library=Stratagene lung (#937210) vector=pBluescript
    SK-host=SOLR cells (Kenamycin resistant) primer=M13RPI Rsite1=EcoRI
    Rsite2=XhoI Normal lung tissue from a 72 year old male. Cloned
    unidirectionally. Primer: Oligo dT. Average insert size: 1.0 kb; Uni-ZAP
    XR vector; 5' adaptor sequence: 5'GAATTCGGCACGAG-3'; 3' adaptor sequence:
    5'CTCGAGTTTTTTTTTTTTTTTT 3"
 ORGANISM Homo sapiens
    Eukaryota; Metazoa; Chordata; Vertebrata; Gnathostomata; Mammalia; Eutheria;
    Primates; Catarrhini; Hominidae; Homo.
REFERENCE 1 (bases 1 to 396)
 AUTHORS Hillier,L., Clark, N., Dubuque, T., Elliston, K., Hawkins, M.,
    Holman, M., Hultman, M., Kucaba, T., Le, M., Lennon, G., Marra, M.,
    Parsons, J., Rifkin, L., Rohlfing, T., Tan, F., Trevaskis, E.,
    Waterston, R., Williamson, A., Wohldmann, P. and Wilson, R.
 TITLE  WashU-Merck EST Project
 JOURNAL  Unpublished (1995)
COMMENT
    Contact: Wilson RK
    WashU-Merck EST Project
    Washington University School of Medicine
    4444 Forest Park Parkway, Box 8501, St. Louis, MO 63108
    Tel: 314 286 1800
    Fax: 314 286 1810
    Email: est@watson.wustl.edu
    Insert Size: 280
    High quality sequence stops: 242 Source: IMAGE Consortium, LLNL This
    clone is available royalty-free through LLNL; contact the IMAGE
    Consortium (info@image.llnl.gov) for further information.
FEATURES        Location/Qualifiers
  source        1..396
       /organism="Homo sapiens"
       /clone="81420"
BASE COUNT  119 a  75 c  74 g  126 t    2 others
ORIGIN T60214 Length: 396 September 10, 1996 19:07 Type: N Check: 5134 ..

```
  1 tcaaatccag aggctagcag ttcaacttct gtaacaccag atgttagtga caatgaacct
 61 gatcattata gatattctga caccactgac tctgatccag agaatgaacc ttttgatgaa
121 gatcagcata cacaaattac aaaagtctga atttttttt atcaagaggg ataaaacacc
181 atgaaaataa acttgaataa actgaaaatg ggacttttt ttttttttaat gggcaatagg
241 gacattgtgt caggattacc agttataggg gacaattctc ttttccctgg acccaatctt
301 gttttttacc ctatacatcc accgggggtt ttttgacact tgtttgtccc agttggaaaa
361 agggttgtnt tggccgtngt ccaggattat accctt
//
```

TABLE 18

LOCUS    W23656    451 bp    mRNA    EST    20-AUG-1996
DEFINITION zb46c05.r1 Soares_fetal_lung_NbHL19W Homo sapiens cDNA clone
    IMAGE:306632 5'.
ACCESSION  W23656
NID    g1300471
KEYWORDS  EST.
SOURCE    human.
 ORGANISM Homo sapiens
    Eukaryota; mitochondrial eukaryotes; Metazoa; Chordata; Vertebrata; Eutheria;
    Primates; Catarrhini; Hominidae; Homo.
REFERENCE  1 (bases 1 to 451)
 AUTHORS  Hillier, L., Clark, N., Dubuque, T., Elliston, K., Hawkins, M.,
    Holman, M., Hultman, M., Kucaba, T., Le, M., Lennon, G., Marra, M.,
    Parsons, J., Rifkin, L., Rohlfing, T., Soares, M., Tan, F., Trevaskis, E.,
    Waterston, R., Williamson, A., Wohldmann, P. and Wilson, R.

TABLE 18-continued

TITLE   WashU-Merck EST Project
JOURNAL   Unpublished (1995)
COMMENT
   Contact: Wilson RK
   WashU-Merck EST Project
   Washington University School of Medicine
   4444 Forest Park Parkway, Box 8501, St. Louis, MO 63108
   Tel: 314 286 1800
   Fax: 314 286 1810
   Email: est@watson.wustl.edu
   This clone is available royalty-free through LLNL; contact the
   IMAGE Consortium (intu#image.llnl.gov) for further information.
   Seq primer: mob.REGA+ET
   High quality sequence stop: 240.
FEATURES       Location/Qualifiers
  source        1..451
     /organism="Homo sapiens"
     /note="Organ: lung; Vector: pT7T3D (Pharmacia) with a
     modified polylinker; Site_1: Not I; Site_2: Eco RI; 1st
     strand cDNA was primed with a Not I - oligo(dT)primer
     [5'-TGTTACCAATCTGAAGTGGGAGCGGCCGCAATTTTTTTTTTTTTTTTT-3'],
     double-stranded cDNA was size selected, ligated to Eco RI
     adapters (Pharmacia), digested with Not I and cloned into
     the Not I and Eco RI sites of a modified pT7T3 vector
     (Pharmacia). Library went through one round of
     normalization to a Cot = 5. Library constructed by Bento
     Soares and M. Fatima Bonaldo. This library was constructed
     from the same fetus as the fetal heart library, Soares fetal heart NbHHI9W".
     /clone="306632"
     /clone_lib="Soares_fetal_lung_NbHL19W"
     /dev_stage="19 weeks"
     /lab_host="DH10B (ampicillin resistant)"
     mRNA <1.. >451
BASE COUNT     148 a    76 c    82 g    141 t    4 others
ORIGIN W23656 Length: 451 September 10 1996 19:10 Type: N Check: 6961 ..
     1 caacttctgt aacaccagat gttagtgaca atgaacctga tcattataga tattctgaca
    61 ccactgactc tgatccagag aatgaaccit ttgatgaaga tcagcataca caaattacaa
   121 aagtctgaat tttttrtat caagagggat aaaacaccat gaaaataaac ttgaataaac
   181 tgaaaatgga cctttttttt tttaatggca ataggacatt gtgtcagatt accagttata
   241 ggaacaattc tctttcctg accaatcttg ntttacccna tacattccca ggggtttgga
   301 cacttggtgg tccagnttga aaaaaggttg tgtagctgtg ncatggtata tacctttttg
   361 tggccaaaag ggacatttaa aattcaatta ggattaataa agatgggcac tttcccgttt
   421 aattccagtt ttataaaaag tggggacaga c
//

TABLE 19

LOCUS    W27533    902 bp    mRNA    EST    08-MAY-1996
DEFINITION 32b2 Human retina cDNA randomly primed sublibrary Homo sapiens
   cDNA, mRNA sequence.
ACCESSION W27533
NID      g1307337
KEYWORDS EST.
SOURCE    human.
 ORGANISM Homo sapiens
   Eukaryota; mitochondrial eukaryotes; Metazoa; Chordata; Vertebrata; Mammalia; Eutheria;
   Primates; Catarrhini; Hominidae; Homo.
REFERENCE 1 (bases 1 to 902)
 AUTHORS   Macke, J., Smallwood, P. and Nathans, J.
 TITLE    Adult Human Retina cDNA
 JOURNAL   Unpublished (1996)
COMMENT
   Contact: Dr. Jeremy Nathans
   Dr. Jeremy Nathans, Dept. of Molecular Biology and Genetics
   Johns Hopkins School of Medicine
   725 North Wolfe Street, Baltimore, MD 21205
   Tel: 410 955 4678
   Fax: 410 614 0827
   Email: jeremy_nathans@qmail.bsjhu.edu
   Clones from this library are NOT available.
   PCR PRimers
   FORWARD: CTTTTGAGCAAGTTCAGCCTGGTTAAGT
   BACKWARD: GAGGTGGCTTATGAGTATTTCTTCCAGGGTAA
   Seq primer: GGGTAAAAAGCAAAAGAATT.
FEATURES       Location/Qualifiers
  source        1..902

TABLE 19-continued

```
    /organism="Homo sapiens"
    /note="Organ: eye; Vector: lambda gt10; Site_1: EcoRI;
    Site_2: EcoRI; The library used for sequencing was a
    sublibrary derived from a human retina cDNA library.
    Inserts from retina cDNA library DNA were isolated,
    randomly primed, PCR amplified, size-selected, and cloned
    into lambda gt10. Individual plaques were arrayed and
    used as templates for PCR amplification, and these PCR
    products were used for sequencing."
    /clone_lib="Human retina cDNA randomly primed sublibrary"
    /sex="mixed (males and females)"
    /tissue_type="retina"
    /dev_stage="adult"
    /lab_host="E. coli strain K802"
    mRNA    <1.. >7902
BASE COUNT      124 a     110 c    117 g    131 t    420 others
ORIGIN  W27533 Length: 902 September 10, 1996 19:05 Type: N Check: 224 ..
     1 gngnnnttnc tactcangat catttggngg ttaaagtaag tactagatan tccttgtcat
    61 tatctgcacg ctctatactg caaatgctat cgatttcttg atcacataga cttccatttt
   121 ctacttttnc tgaggttncc tctggtcctg gtatgaagaa tgtatttacc caaaagtgaa
   181 acattgggtc cttttttagc atctggtnct gtgngtggaa gaactctact tggatatcac
   241 cacacacagg taacggctga gggaactcaa agtacatgaa cttgtcttcc cgncgngtgg
   301 gtcctgaatt ggaggaatat ntcttcacct nnagctggca gaccacaaac tgaggattgc
   361 aagtnccgcc actgaacatg ggaataggnt caaacatcan cttgggaaac aacagggnca
   421 ctggtctttt anccagntga tcnnnacagg gggtatnata nacananggg cccnnnnngg
   481 aatgggncnc cnnggggttn nncccnnnnc ccannnnnnc anngggntnc cggngggnnn
   541 nnnnnnnnnn nnnnnnnnnn nnnnnnnnnn nnnnnnnnnn nnnnnnnnnn nnnnnnnnnn
   601 nnnnnnnnnn nnnnnnnnnn nnnnnnnnnn nnnnnnnnnn nnnnnnnnnn nnnnnnnnnn
   661 nnnnnnnnnn nnnnnnnnnn nnnnnnnnnn nnnnnnnnnn nnnnnnnnnn nnnnnnnnnn
   721 nnnnnnnnnn nnnnnnnnnn nnnnnnnnnn nnnnnnnnnn nnnnnnnnnn nnnnnnnnnn
   781 nnnnnnnnnn nnnnnnnnnn nnnnnnnnnn nnnnnnnnnn nnnnnnnnnn nnnnnnnnnn
   841 nnnnnnnnnn nnnnnnnnnn nnnnnnnnnn nnnnnnnnnn nnnnnnnnnn nnnnnnnnnn
   901 cc
//
```

TABLE 20

```
LOCUS      W30684      601 bp      mRNA      EST      09-MAY-1996
DEFINITION zb77b11.r1 Soares_senescent_fibroblasts_NbHSF Homo sapiens cDNA
    clone IMAGE:309597 5'.
ACCESSION  W30684
NID        g13311870
KEYWORDS   EST.
SOURCE     human.
ORGANISM   Homo sapiens
    Eukaryota; mitochondrial eukaryotes; Metazoa; Chordata; Vertebrata; Eutheria;
    Primates; Catarrhini; Hominidae; Homo.
REFERENCE  1 (bases 1 to 601)
AUTHORS    Hillier, L., Clark, N., Dubuque, T., Elliston, K., Hawkins, M.,
    Holman, M., Hultman, M., Kucaba, T., Le, M., Lennon, G., Marra, M.,
    Parsons, J., Rifkin, L., Rohlfing, T., Tan, F., Trevaskis, E.,
    Waterston, R., Williamson, A., Wohldmann, P. and Wilson, R.
TITLE      WashU-Merck EST Project
JOURNAL    Unpublished (1995)
COMMENT
    Contact: Wilson RK
    WashU-Merck EST Project
    Washington University School of Medicine
    4444 Forest Park Parkway, Box 8501, St. Louis, MO 63108
    Tel: 314 286 1800
    Fax: 314 286 1810
    Email: est@watson.wustl.edu
    This clone is available royalty-free through LLNL; contact the
    IMAGE Consortium (info@image.llnl.gov) for further information.
    Insert Length: 998 Std Error: 0.00
    eq primer: mob.REGA+ET
    High quality sequence stop: 463.
FEATURES           Location/Qualifiers
  source       1..601
    /organism="Homo sapiens"
    /note="Vector: pT7T3D (Pharmacia) with a modified
    polylinker V_TYPE: phagemid Site_1 Not I; Site_2: Eco
    RI; [5'
    TGTTACCAATCTGAAGTGGGAGCGGCCGCATTTTTTTTTTTTTTTTTTT 3'],
    double-stranded cDNA was size selected, ligated to Eco RI
    adapters (Pharmacia), digested with Not I and cloned into
```

TABLE 20-continued the Not I and Eco RI sites of a modified pT7T3 vector
(Pharmacia). Library went through one round of
normalization to a Cot = 5. Library constructed by Bento
Soares and M. Fatima Bonaldo."
/clone="309597"
/clone_lib="Soares_senescent_fibroblasts_NbHSF"
/lab_host="DH10B (ampicillin resistant)"
mRNA <1..>601
BASE COUNT    176 a    105 c    122 g    197 t    1 others
ORIGIN W30684 Length: 601 September 10, 1996 19:13 Type: N Check: 2320 ..
    1 gcaagaggga taaaacacca tgaaataaa cttgaataaa ctgaaaatgg acccttttt
   61 ttttaatggc aataggacat tgtgtcagat taccagttat aggaacaatt ctcttttcct
  121 gaccaatctt gttttaccct atacatccac agggttttga cacttgttgt ccagngaaa
  181 aaaggttgtg tagctgtgtc atgtatatac cttttgtgt caaaaggaca tttaaaattc
  241 aattaggatt aataaagatg gcactttccc gtttattcc agttttataa aaagtggaga
  301 cagactgatg tgtatacgta ggaattttt ccttttgtgt tctgtcacca actgaagtgg
  361 ctaaagagct ttgtgatata ctggttcaca tcctacccct ttgcacftgt ggcaacagat
  421 aagtttgcag ttgggctaag agaggtttcc gaagggtttt gctacattct aatgcatgta
  481 ttcggggtta ggggaatgga ggggaatgct cagaaaggaa ataattttaa tgctggactc
  541 tggaccatat accatctcca gctanttaca cacacctttc cttagcatgc cacagttatt
  601 a
//

TABLE 21

LOCUS    W81026    453 bp    mRNA    EST    26-JUN-1996
DEFINITION zd84a07.r1 Soares_fetal_heart_NbHH19W Homo sapiens cDNA clone
    347316 5'.
ACCESSION W81026
NID    g1392060
KEYWORDS EST.
SOURCE  human.
 ORGANISM Homo sapiens
    Eukaryota; mitochondrial eukaryotes; Metazoa; Chordata; Vertebrata; Eutheria;
    Primates; Catarrhini; Hominidae; Homo.
REFERENCE 1 (bases 1 to 453)
 AUTHORS    Hillier, L., Clark, N., Dubuque, T., Elliston, K., Hawkins, M.,
    Holman, M., Hultman, M., Kucaba, T., Le, M., Lennon, G., Marra, M.,
    Parsons, J., Rifkin, L., Rohlfing, T., Soares, M., Tan, F.,
    Trevaskis, E., Waterston, R., Williamson, A., Wohldmann, P. and
    Wilson, R.
    TITLE   The WashU-Merck EST Project
    JOURNAL   Unpublished (1995)
COMMENT
    Contact: Wilson RK
    Washington University School of Medicine
    4444 Forest Park Parkway, Box 8501, St. Louis, MO 63108
    Tel: 314 286 1800
    Fax: 314 286 1810
    Email: est@watson.wustl.edu
    This clone is available royalty-free through LLNL; contact the
    IMAGE Consortium (info@image.llnl.gov) for further information.
    Seq primer: mob.REGA+ET
    High quality sequence stop: 392.
FEATURES        Location/Qualifiers
  source        1..453
        /organism="Homo sapiens"
        /note="Organ: heart; Vector: pT7T3D (Pharmacia) with a
        modified polylinker; Site_I: Not 1; Site_2: Eco RI; 1st
        strand cDNA was primed with a Not 1 - oligo(dT) primer [5'
        TGTTACCAATCTGAAGTGGGAGCGGCCGCATCTTTTTTTTTTTTTTTT 3'],
        double-stranded cDNA was size selected, ligated to Eco RI
        adapters (Pharmacia), digested with Not I and cloned into
        the Not I and Eco RI sites of a modified pT7T3 vector
        (Pharmacia). Library went through one round of
        normalization to a Cot = 5. Library constructed by
        M. Fatima Bonaldo. This library was constructed from the
        same fetus as the fetal lung library, Soares fetal lung
        NbHL19W."
        /clone="347316"
        /clone_lib="Soares_fetal_heart_NbHH19W"
        /sex="unknown"
        /dev_stage="19 weeks"
        /lab_host="DH10B (ampicillin resistant)"
        mRNA <1..>453
BASE COUNT    190 a    77 c    79 g    106 t    1 others

TABLE 21-continued

ORIGIN W81026 Length: 453 September 10, 1996 19:03 Type: N Check: 2953 ..
```
    1 ataccaggac cagaggaaac ctcagaaaaa gtagaaaatg gaagtctatg tgatcaagaa
   61 atcgatagca tttgcagtat agagcgtgca gataatgaca aggaatatct agtacttact
  121 ttaacaaaaa atgatcttga caaagcaaat aaagacaaag ccaaccgata cttttctcca
  181 aattttaagg tgaagctgta cttcacaaaa acagtagagg agccgtcaaa tccagaggct
  241 agcagttcaa cttctgtaac accagatgtt acgtgacaat gaacctgatc attatagata
  301 ttctgacacc actgactctg atccagagaa tgaacctttt gatgaagatc agcatacaca
  361 aattacaaaa gtctgaattt tttttatca agagggataa aacaccatgg aaaataaact
  421 tggaataaac tgaaaaanaa aaaaaaaaaa gat
```
//

TABLE 22

LOCUS    W81062    429 bp    mRNA    EST    26-JUN-1996
DEFINITION zd84a07.s1 Soares_fetal_heart_NbHH19W Homo sapiens cDNA clone
    347316 3'.
ACCESSION  W81062
NID    g1392114
KEYWORDS  EST.
SOURCE  human.
  ORGANISM Homo sapiens
    Eukaryota; mitochondrial eukaryotes; Metazoa; Chordata; Vertebrata; Eutheria;
    Primates; Catarrhini; Hominidae; Homo.
REFERENCE  1 (bases 1 to 429)
  AUTHORS  Hillier, L., Clark, N., Dubuque, T., Elliston, K., Hawkins, M.,
    Holman, M., Hultman, M., Kucaba, T., Le, M., Lennon, G., Marra, M.,
    Parsons, J., Rifkin, L., Rohlfing, T., Soares, M., Tan, F.,
    Trevaskis, E., Waterston, R., Williamson, A., Wohldmann, P. and
    Wilson, R.
  TITLE    The WashU-Merck EST Project
  JOURNAL  Unpublished (1995)
COMMENT
    Contact: Wilson RK
    WashU-Merck EST Project
    Washington University School of Medicine
    4444 Forest Park Parkway, Box 8501, St. Louis, MO 63108
    Tel: 314 286 1800
    Fax: 314 236 1810
    Email: est@watson.wustl.edu
    This clone is available royalty-free through LLNL; contact the
    IMAGE Consortium (info@image.llnl.gov) for further information.
    Insert Length: 500 Std Error: 0.00
    Seq primer: mob.REGA+ET
    High quality sequence stop: 324.
FEATURES        Location/Qualifiers
  source      1..429
      /organism="Homo sapiens"
      /note="Organ: heart; Vector: pT7T3D (Pharmacia) with a
      modified polylinker; Site_1: Not I; Site_2: Eco RI; 1st
      strand cDNA was primed with a Not I - oligo(dT) primer [5'
      TGTTACCAATCTGAAGTGGGAGCGGCCGCATCTTTTTTTTTTTTTTTTTT 3'],
      double-stranded cDNA was size selected, ligated to Eco RI
      adapters (Pharmacia), digested with Not I and cloned into
      the Not I and Eco RI sites of a modified pT7T3 vector
      (Pharmacia). Library went through one round of
      normalization to a Cot = 5. Library constructed by
      M. Fatima Bonaldo. This library was constructed from the
      same fetus as the fetal lung library, Soares fetal lung
      NbHL19W."
      /clone="347316"
      /clone_lib="Soares_fetal_heart_NbHH19W"
      /sex="unknown"
      /dev_stage="19 weeks"
      /lab_host="DH10B (ampicillin resistant)"
      mRNA compliment (<1.. >429)
BASE COUNT    105 a    83 c    77 g    161 t    3 others
ORIGIN W81062 Length: 429 September 10, 1996 19:05 Type: N Check: 7359 ..
```
    1 cagtttattc aagtttattt tcatggtgtt ttatccctct tgataaaaaa aaattcagac
   61 ttttgtaatt tgtgtatgct gatcttcatc aaaaggttca ttctctggat cagagtcagt
  121 ggtgtcagaa tatctataat gatcaggttc attgtcacta acatctggtg ttacagaagt
  181 tgaactgcta gcctctggat ttgacggctc ctctactgtt tttgtgaagt acagcttcac
  241 cttaaaattt ggagaaaagt atcggttggc tttgtcttta tttgctttgt caagatcatt
```

TABLE 22-continued

```
301 ttttgttaaa gtaagtacta agatattcct tgtcattatc tgcacgctct aatactgcaa
361 atggctatcc gatttcctgg atccaccata ggncttccna tttccaactt ttccctgngg
421 ttccccgg
//
```

TABLE 23

| | |
|---|---|
| LOCUS | AAO3922    238 bp    mRNA    EST    30-AUG-1996 |
| DEFINITION | zk48f11.r1 Soares pregnant uterus NbHPU Homo sapiens CDNA clone 486093 5'. |
| ACCESSION | AA039223 |
| NID | g1515519 |
| KEYWORDS. | EST. |
| SOURCE | human. |
| ORGANISM | Homo sapiens<br>Eukaryotae; mitochondrial eukaryotes; Metazoa; Chordata; Vertebrata; Eutheria; Primates; Catarrhini; Hominidae; Homo. |
| REFERENCE | 1 (bases 1 to 238) |
| AUTHORS | Hillier, L., Clark, N., Dubuque, T., Elliston, K., Hawkins, M., Holman, M., Hultman, M., Kucaba, T., Le, M., Lennon, G., Marra, M., Parsons, J., Rifkin, L., Rohlfing, T., Soares, M., Tan, F., Trevaskis, E., Waterston, R., Williamson, A., Wohldmann, P. and Wilson, R. |
| TITLE | The WashU-Merck EST Project |
| JOURNAL | Unpublished (1995) |
| COMMENT | Contact: Wilson RK<br>Washu-Merck EST Project<br>Washington University School of Medicine<br>4444 Forest Park Parkway, Box 8501, St. Louis, MO 63108<br>Tel: 314 286 1800<br>Fax: 314 286 1810<br>Email: est@watson.wustl.edu<br>This clone is available royalty-free through LLNL; contact the IMAGE Consortium (info@image.llnl.gov) for further information.<br>Seq primer: -28M13 rev2 from Amersham<br>High quality sequence stop: 81. |
| FEATURES | Location/Qualifiers |
| source | 1..238<br>/organism="Homo sapiens"<br>/note="Organ: uterus; Vector: pT7T3-Pac; Site_1: Not I; Site_2: Eco RI; 1st strand cDNA was primed with a Not I - oligo(dT) primer [5' AACTGGAAGAATTCGCGGCCGCCTTTTTTTTTTTTTTTTTT 3'], double-stranded cDNA was ligated to Eco RI adaptors (Pharmacia), digested with Not I and cloned into the Not I and Eco RI sites of the modified pT7T3 vector. Library went through one round of normalization. Library constructed by M. Fatima Bonaldo."<br>/clone="486093"<br>/clone_lib="Soares pregnant uterus NbHPU"<br>/sex="female"<br>/dev_stage="adult"<br>/lab_host="DH10BZ" |
| mRNA | <1..>238 |
| BASE COUNT | 89 a    41 c    43 g    59 t    6 others |
| ORIGIN | |

```
  1 taaaaagga caaaatgttt cacttttggg taaatacatt cttcatacca ggaccagagg
 61 aaacctcaga aaaagtagaa aatggaagtc tatgtgatca agaaatccga tagcatttgc
121 ngtatagagc gtgcagataa tgncaaggaa tatctagtac ttactttaac caaaaantga
181 tcttgacaaa gcaaataaag nccaaccnac cgntactttt ctcccaattt ttaggggg
//
```

TABLE 24

| | |
|---|---|
| LOCUS | C17744    332 bp    mRNA    EST    9-SEP-1996 |
| DEFINITION | Human placenta CDNA 5'-end GEN-552A05. |
| ACCESSION | C17744 |
| NID | g1579347 |
| KEYWORDS | EST(expressed sequence tag; Human placenta. |
| SOURCE | Homo sapiens placenta cDNA to mRNA, clone:552A05. |
| ORGANISM | Homo sapiens<br>Eukaryotae; mitochondrial eukaryotes; Metazoa; Chordata; Vertebrata; Eutheria; Primates; Catarrhini; Hominidae, Homo. |

TABLE 24-continued

| | |
|---|---|
| REFERENCE | 1 (bases 1 to 332) |
| AUTHORS | Fujiwara, T. |
| TITLE | Direct Submission |
| JOURNAL | Submitted (24-JUN-1996) to the DDBJ/EMBL/GenBank databases. Tsutomu Fujiwara, Otsuka GEN Research Institute, Otsuka Pharmaceutical Co., Ltd; 463-10 Kagasuno Kawauchi-chol Tokushima, Tokushima 771-01, Japan (Tel: +81-886-65-2888, Fax: +81-866-37-1035) |
| REFERENCE | 2 (sites) |
| AUTHORS | Fujiwara, T., Hirano, H., Hishigaki, H., Horie, M., Kawai, A., Kuga, Y., Kyushiki, H., Nagata, M., Okuno, S., Ozaki, K., Shimizu, F., Shimada, Y., Shinomiya, H., Suzuki, M., Takaichi, A., Takeda, S., Watanabe, T., Maekawa, H., Nakamura, Y. and Takahashi, E. |
| TITLE | Otsuka cDNA project |
| JOURNAL | Unpublished (1996) |
| FEATURES | Location/Qualifiers |
| source | 1..332 |
| | /organism="Homo sapiens" |
| | /clone="552A05" |
| | /tissue_type="placenta" |
| BASE COUNT | 78 a    116 c    81 g    57 t |
| ORIGIN | |

```
  1 cgtcttctcc ccattccgct gccgccgctg ccaggcctct gcgctgctga ggagaagcag
 61 gcccagtcgc tgcaaccatc cagcagccgc cgcagcagcc attacccggc tgcggtccag
121 agccaagcgg cggcagagcg aggggcatca gctaccgcca agtccagagc catttccatc
181 ctgcagaaga agccccgcca ccagcagctt ctgccatctc tctcctcctt ttcttcagcc
241 acaggctccc agacatgaca gccatcatca aagagatcgt tagcagaaac aaaaggagat
301 atcaagagga tggattcgac ttagacttga cc
//
```

TABLE 25

| | |
|---|---|
| LOCUS | W37864    543 bp    mRNA    EST 15-MAY-1996 |
| DEFINITION | zc13a05.s1 Soares parathyroid tumor NbHPA Homo sapiens cDNA    clone 322160 3'. |
| ACCESSION | W37864 |
| NID | g1319458 |
| KEYWORDS | EST. |
| SOURCE | human. |
| ORGANISM | Horno sapiens<br>Eukaryotae; mitochondrial eukaryotes; Metazoa; Chordata; Vertebrata; Eutheria; Primates; catarrhini; Hominidae; Homo. |
| REFERENCE | 1 (bases 1 to 543) |
| AUTHORS | Hillier, L., Clark, N., Dubuque, T., Elliston, K., Hawkins, M., Holman, M., Hultman, M., Kucaba, T., Le, M., Lennon, G., Marra, M., Parsons, J., Rifkin, L., Rohlfing, T., Soares, M., Tan, F., Trevaskis, E., Waterston, R., Williamson, A., Wohldmann, P. and Wilson, R. |
| TITLE | The Washu-Merck EST Project |
| JOURNAL | Unpublished (1995) |
| COMMENT | Contact: Wilson RK<br>WashU-Merck EST Project<br>Washington University School of Medicine<br>4444 Forest Park Parkway, Box 8501, St. Louis, MO 63108<br>Tel: 314 286 1800<br>Fax: 314 286 1810<br>Email: est@watson.wustl.edu<br>This clone is available royalty-free through LLNL contact the<br>IMAGE Consortium (info@image.llnl.gov) for further information.<br>Seq primer: mob.REGA+ET<br>High quality sequence stop: 337. |
| FEATURES | Location/Qualifiers |
| source | 1..543<br>/organism="Homo sapiens"<br>/note="Vector: pT7T3D (Pharmacia) with a modified polylinker; Site_1: Not I; Site_2: Eco RI; 1st strand cDNA<br>was primed with a Not I - oligo(dT) primer (5'-TGTTACCAATCTGAAGTGGGAGCGGCCGCACCAATTTTTTTTTTTTTTTTTTTTT<br>T<br>  T-3'], double-stranded cDNA was size selected, |

TABLE 25-continued

|  | ligated to Eco RI adapters (Pharmacia), digested with Not I and cloned into the Not I and Eco RI sites of a modified pT7T3 vector (Pharmacia). Library went through one round of normalization to a Cot = 5. Library constructed by Bento Soares and M. Fatima Bonaldo. RNA from sporadic parathyroid adenomas was kindly provided by Dr. Stephen Marx, National Institute of Diabetes and Digestive and Kidney Diseases, NIH." /clone="322160" /clone_lib="Soares parathyroid tumor NbHPA" /dev_stage="adult" /lab_host="DH10B (ampicillin resistant)" |
|---|---|
| mRNA | complement(<1..>543) |
| BASE COUNT | 159 a    112 c    91 g    176 t    5 others |
| ORIGIN | |

```
  1 tttttttttt acaattgaga aaacatattt aataaatcat tgtcaatttt tataatgttt
 61 caagcccatt ctttgttgat agcctccaca tttatatggt taagtcattg ttgctgtgtt
121 tcttacctat gacattattt ttatatccct tcatttgtgg atcttaagat gttgcagaag
181 gttcattcct gtaccccaat acagattcac ttcctttagc tgcctttct agcaccaata
241 tgctttaaaa aaaaatgcgc aaacaacaan gcagtgacag cggccaattc ctcgaatgtc
301 cagtataata actgtagcat gctaaagaaa ggtgtgtgta aatagctcgg agatgggtat
361 atggtccaga gtccagcata aaattatttc ctttctgagc attccctcca ttgcccctaa
421 cccgaataca tgcattagaa tggtagcana acccttncgg aaacctctct tagccaactg
481 caaacttatc tgttgccaca agtgcaaagg gggtaggatg tgaanccagt atattccnca
541 aag
```

TABLE 26

| LOCUS | W37855    281 bp    mRNA    EST    15-MAY-1996 |
|---|---|
| DEFINITION | zc13a05.r1 Soares parathyroid tumor NbHPA Homo sapiens cDNA clone 322160 5'. |
| ACCESSION | W37855 |
| NID | g1319519 |
| KEYWORDS | EST. |
| SOURCE | human. |
| ORGANISM | Homo sapiens Eukaryotae; mitochondrial eukaryotes; Metazoa; Chordata; Vertebrata; Eutheria; Primates; Catarrhini; Hominidae; Homo. |
| REFERENCE | 1 (bases 1 to 281) |
| AUTHORS | Hillier, L., Clark, N., Dubuque, T., Elliston, K., Hawkins, M., Holman, M., Hultman, M., Kucaba, T., Le, M., Lennon, G., Marra, M., Parsons, J., Rifkin, L., Rohlfing, T., Soares, M., Tan, F., Trevaskis, E., Waterston, R., Williamson, A., Wohldmann, P. and Wilson, R. |
| TITLE | The Washu-Merck EST Project |
| JOURNAL | Unpublished (1995) |
| COMMENT | Contact: Wilson RK WashU-Merck EST Project Washington University School of Medicine 4444 Forest Park Parkway, Box 8501, St. Louis, MO 63108 Tel: 314 286 1800 Fax: 314 286 1810 Email: est@watson.wustl.edu This clone is available royalty-free through LLNL; contact the IMAGE Consortium (info@image.llnl.gov) for further information. Seq primer: mob.REGA+ET High quality sequence stop: 236. |
| FEATURES | Location/Qualifiers |
| source | 1..281 /organism="Homo sapiens" /note="Vector: pT7T3D (Pharmacia) with a modified polylinker; Site 1: Not I; Site 2: Eco RI; 1st strand cDNA was primed with a Not I - oligo(dT) primer [5'-TGTTACCAATCTGAAGTGGGAGCGGCCGCACCAATTTTTTTTTTTTTTTTTTTTTT T-3'], double-stranded cDNA was size selected, ligated to Eco RI adapters (Pharmacia), digested with Not I and cloned into the Not I and Eco RI sites of a modified pT7T3 vector (Pharmacia). Library went through one round of normalization to a Cot = 5. Library constructed by Bento Soares and M. Fatima Bonaldo. RNA from sporadic parathyroid adenomas was kindly provided by Dr. Stephen Marx, National Institute of Diabetes and Digestive and Kidney Diseases, NIH." /clone="322160" |

TABLE 26-continued

```
                   /clone_lib="Soares parathyroid tumor NbHFA"
                   /dev_stage="adult"
                   /lab_host="DH10B (ampicillin resistant)"
       mRNA        <1..>281
BASE COUNT      77 a    46 c    59 g    98 t    1 others
ORIGIN
     1 aagctgtgtc atgtatatac cttttgtgt caaaaggaca tttaaaattc aattaggatt
    61 aataaagatg gcactttccc gttttattcc agttttataa aaagtggaga cagactgatg
   121 tgtatacgta ggaattttt cctttgtgt tctgtcacca actgaagtgg ctaaagagct
   181 ttgtgatata ctggttcaca tcctaccct ttgcacttgt ggcaacagat aagttttgcag
   241 ttggctaaag agaggtttnc cgaagggttt tggctacatt c
//
```

TABLE 27

| | |
|---|---|
| LOCUS | M78282    455 bp    mRNA    EST    26-MAY-1992 |
| DEFINITION | EST00430 Homo sapiens cDNA clone HFBBA34. |
| ACCESSION | M78282 |
| NID | g272598 |
| KEYWORDS | EST. |
| SOURCE | human clone=HFBBA34 library=Fetal brain, Stratagene (cat#936206)<br>vector=LambdaZAP-II primer=M13 Forward 17–18 wk gestation, female;<br>oligo-dT + random primed cDNA synthesis; lambdaZAP-II vector, 1.0kb average insert size. |
| ORGANISM | Homo sapiens<br>Eukaryotae; Metazoa; Eumetazoa; Bilateria; Coelomata; Deuterostomia; Chordata; Vertebrata; Gnathostomata; Osteichthyes;<br>Sarcopterygii; Choanata; Tetrapoda; Amniota; Mammalia; Theria;<br>Eutheria; Archonta; Primates; Catarrhini; Hominidae; Homo. |
| REFERENCE | 1 (bases 1 to 455) |
| AUTHORS | Adams, M. D., Dubnick, M., Kerlavage, A. R., Moreno, R., Kelley, J. M.<br>Utterback, T. R., Nagle, J. W., Fields, C. and Venter, J. C. |
| TITLE | Sequence identification of 2,375 human brain genes |
| JOURNAL | Nature 355 (6361), 632–634 (1992) |
| MEDLINE | 92168112 |
| COMMENT | Contact: Kerlavage AR<br>The Institute for Genomic Research<br>932 Clopper Road, Gaithersburg, MD 20878<br>Tel: 301 869 9056<br>Fax: 301 869 9423<br>Email: arkerlav@tigr.org. |
| FEATURES | Location/Qualifiers |
| source | 1..455<br>/organism="Homo sapiens"<br>/clone="HFBBA34" |
| gene | <1..>455<br>/gene="D0S1270E" |
| mRNA | <1..>455<br>/gene="DOS1270E" |
| BASE COUNT | 135 a    94 c    77 g    146 t    3 others |

```
ORIGIN
     1 gttacaattg agaaaacata tttaataaat cattgtcaat tttnataatg tttcaagccc
    61 attctttgtt gatagcctcc acatttatat ggttaagtca ttgttgctgt gtttcttacc
   121 tatgacatta ttttnatatc ccttcatttg tggatcttaa gatgttgcag aaggttcatt
   181 cctgtacccc aatacagatt cacttccttt agctgccttt nctagcacca atatgcttta
   241 aaaaaaatg cgcaaacaac aagcagtgac agcggccaat tcctcgaatg tccagattaa
   301 taactgtagc atgctaaaga aaggtgtgtg taaatagctg gagatggtat atggtccaga
   361 gtccagcata aaattatttc ctttctgagg cattccctcc attcccctaa cccggataca
   421 tgcattagga atgtagcaaa acccttcggg gaacc
//
```

TABLE 28

| | |
|---|---|
| LOCUS | N98421    392 bp    mRNA    EST    20-AUG-1996 |
| DEFINITION | zb77b11.s1 Soares senescent fibroblasts NbHSF Homo |

TABLE 28-continued

|  |  |
|---|---|
|  | sapiens CDNA |
|  | clone 309597 3'. |
| ACCESSION | N98421 |
| NID | g1269847 |
| KEYWORDS | EST. |
| SOURCE | human. |
| ORGANISM | Homo sapiens |
|  | Eukaryotae; mitochondrial eukaryotes; Metazoa; Chordata; |
|  | Vertebrata; Eutheria; Primates; Catarrhini; Hominidae; |
|  | Homo. |
| REFERENCE | 1 (bases 1 to 392) |
| AUTHORS | Hillier, L., Clark, N., Dubuque, T., Elliston, K., |
|  | Hawkins, M., |
|  | Holman, M., Hultman, M., Kucaba, T., Le, M., Lennon, G., |
|  | Marra, M., |
|  | Parsons, J., Rifkin, L., Rohlfing, T., Tan, F., Trevaskis, E., |
|  | Waterston, R., Williamson, A., Wohldmann, P. and Wilson, R. |
| TITLE | WashU-Merck EST Project |
| JOURNAL | Unpublished (1995) |
| COMMENT | Contact: Wilson RK |
|  | Washu-Merck EST Project |
|  | Washington University School of Medicine |
|  | 4444 Forest Park Parkway, Box 8501, St. Louis, MO 63108 |
|  | Tel: 314 286 1800 |
|  | Fax: 314 286 1810 |
|  | Email: est@watson.wustl.edu |
|  | This clone is available royalty-free through LLNL |
|  | contact the |
|  | IMAGE Consortium (info@image.llnl.gov) for further |
|  | information. |
|  | Insert Length: 998    Std Error: 0.00 |
|  | Seq primer: ETPrimer |
|  | High quality sequence stop: 285. |
| FEATURES | Location/Qualifiers |
| source | 1..392 |
|  | /organism="Homo sapiens" |
|  | /note="Vector: pT7T3D (Pharmacia) with a modified |
|  | polylinker V_TYPE: phagemid; Site_1: Not I; Site_2: Eco |
|  | RI; TGTTACCAATCTGAAGTGGGAGCGGCCGCATTTTTTTTTTTTTTTTTTT |
|  | 3'], double-stranded cDNA was size selected, ligated to |
|  | Eco RI adapters (Pharmacia), digested with Not I and |
|  | cloned into the Not I and Eco RI sites of a modified |
|  | pT7T3 vector (Pharmacia). Library went through one round |
|  | of normalization to a Cot = 5. Library constructed by |
|  | Bento Soares and M. Fatima Bonaldo." |
|  | /clone="309597" |
|  | /clone_lib="Soares senescent fibroblasts NbHSF" |
|  | /tissue_type="senescent fibroblast" |
|  | /lab_host="DH10B (ampicillin resistant)" |
| mRNA | complement(<1..>392) |
| BASE COUNT | 116 a    71 c    62 g    143 t |
| ORIGIN |  |

```
  1 tttttttttt tttacaattg agaaaacata tttaataaat cattgtcaat ttttataatg
 61 tttcaagccc attctttgtt gatagcctcc acatttatat ggttaagtca ttgttgctgt
121 gtttcttacc tatgacatta tttttatatc ccttcatttg tggatcttaa gatgttgcag
181 aaggttcatt cctgtacccc aatacagatt cacttccttt agctgccttt tctagcacca
241 atatgcttta aaaaaaatg cgcaaacaac aagcagtgac agcggccaat tcctcgaatg
301 tccagattaa taactgtagc atgctaaaga aaggtgtgtg taaatagctg gagatggtat
361 atggtccaga gtccagcata aaattattcc tt
//
```

TABLE 29

|  |  |
|---|---|
| LOCUS | AA017584    474 bp    mRNA    EST    02-AUG-1996 |
| DEFINITION | ze39e04.r1 Soares retina N2b4HR Homo sapiens CDNA clone 361374 5'. |
| ACCESSION | AA017584 |
| NID | g1479810 |
| KEYWORDS | EST. |
| SOURCE | human. |
| ORGANISM | Homo sapiens |
|  | Eukaryotae; mitochondrial eukaryotes; Metazoa; Chordata; |
|  | Vertebrata; Eutheria; Primates; Catarrhini; Hominidae; Homo. |
| REFERENCE | 1 (bases 1 to 474) |
| AUTHORS | Hillier, L., Clark, N., Dubuque, T., Elliston, K., Hawkins, M., |
|  | Holman, M., Hultman, M., Kucaba, T., Le, M., Lennon, G., Marra, M., |
|  | Parsons, J., Rifkin, L., Rohlfing, T., Soares, M., Tan, F., |

TABLE 29-continued

|  |  |
|---|---|
| | Trevaskis, E., Waterston, R., Williamson, A., Wohldmann, P. and Wilson, R. |
| TITLE | The Washu-Merck EST Project |
| JOURNAL | Unpublished (1995) |
| COMMENT | Contact: Wilson RK |
| | WashU-Merck EST Project |
| | Washington University School of Medicine |
| | 4444 Forest Park Parkway, Box 8501, St. Louis, MO 63108 |
| | Tel: 314 286 1800 |
| | Fax: 314 286 1810 |
| | Email: est@watson.wustl.edu |
| | This clone is available royalty-free through LLNL; contact the |
| | IMAGE Consortium (info@image.llnl.gov) for further information. |
| | Seq primer: -28M13 rev2 from Amersham |
| | High quality sequence stop: 390. |
| FEATURES | Location/Qualifiers |
| source | 1..474 |
| | /organism="Homo sapiens" |
| | /note="organ: eye; Vector: pT7T3D (Pharmacia) with a |
| | modified polylinker; Site_1: Not I; Site_2: Eco RI; 1st |
| | strand cDNA was primed with a Not I - oligo(dT) primer (5' |
| | TGTTACCAATCTGAAGTGGGAGCGGCCGCGCTTTTTTTTTTTTTTTTTT 3'], |
| | double-stranded CDNA was size selected, ligated to Eco RI |
| | adapters (Pharmacia), digested with Not I and cloned into |
| | the Not I and Eco RI sites of a modified pT7T3 vector |
| | (Pharmacia) . The retinas were obtained from a 55 year old |
| | Caucasian and total cellular poly(A)+ RNA was extracted 6 |
| | hrs after their removal. The retina RNA was kindly |
| | provided by Roderick R. McInnes M.D. Ph.D. from the |
| | University of Toronto. Library constructed by Bento |
| | Soares and M. Fatima Bonaldo." |
| | /clone="361374" |
| | /clone_lib="Soares retina N2b4HR" |
| | /sex="male" |
| | /tissue_type="retina" |
| | /dev_stage="55 year old" |
| | /lab_host="DH10B (ampicillin resistant)" |
| mRNA | <1..>474 |
| BASE COUNT | 156 a    75 c    87 g    153 t    3 others |
| ORIGIN | |

```
  1 gtttcggaac gagggcggct gacagctatt gaataagtgc atcataaatc ttcaaagaaa
 61 aaaaacgctt actgtagaat ctcaaattga aaatttctgt gcagcattac aaaatatttt
121 atatttaatg agaaaaaaga agcttgcagg cagcacatga agcatccaca gcaggtatta
181 tgattgaaaa ctagtaaaat aagtgtaagt tgttgactga tgtaggtact aacagcatct
241 gaattttagc actggccttg attacacagg agatgggagaa gtcgttacaa ttgagaaaac
301 atatttaata aatcattgtc aattttata atgtttcaag cccattcttt gttgatagcc
361 tccacattta tatggttaag tcattgttgc tgtgtttctt acctatgaca ttattttnat
421 atcccttcat ttgtggatct taagatgtng cagaaggttc attcctgnac ccca
```

//

TABLE 30

| | |
|---|---|
| LOCUS | AA017563    241 bp    mRNA    EST    02-AUG-1996 |
| DEFINITION | ze39e04.s1 Soares retina N2b4HR Homo sapiens cDNA clone 361374 3'. |
| ACCESSION | AA017563 |
| NID | g1479716 |
| KEYWORDS | EST. |
| SOURCE | human. |
| ORGANISM | Homo sapiens |
| | Eukaryotae; mitochondrial eukaryotes; Metazoa; Chordata; |
| | Vertebrata; Eutheria; Primates; Catarrhini; Hominidae; Homo. |
| REFERENCE | 1 (bases 1 to 241) |
| AUTHORS | Hillier, L., Clark, N., Dubuque, T., Elliston, K., Hawkins, M., |
| | Holman, M., Hultman, M., Kucaba, T., Le, M., Lennon, G., Marra, M., |
| | Parsons, J., Rifkin, L., Rohlfing, T., Soares, M., Tan, F., |
| | Trevaskis, E., Waterston, R., Williamson, A., Wohldmann, P. and |
| | Wilson, R. |
| TITLE | The WashU-Merck EST Project |
| JOURNAL | Unpublished (1995) |
| COMMENT | Contact: Wilson RK |
| | WashU-Merck EST Project |
| | Washington University School of Medicine. |
| | 4444 Forest Park Parkway, Box 8501, St. Louis, MO 63108 |
| | Tel: 314 286 1800 |
| | Fax: 314 286 1810 |
| | Email: est@watson.wustl.edu |

TABLE 30-continued

|  |  |
|---|---|
|  | This clone is available royalty-free through LLNL; contact the IMAGE Consortium (info@image.llnl.gov) for further information. Possible reversed clone: polyT not found Seq primer: -40M13 fwd. from Amersham High quality sequence stop: 166. |
| FEATURES | Location/Qualifiers |
| source | 1..241 /organism="Homo sapiens" /note="Organ: eye; Vector: pT7T3D (Pharmacia) with a modified polylinker; Site_1: Not I; Site_2: Eco RI; 1st strand cDNA was primed with a Not I - oligo(dT) primer [5' TGTTACCAATCTGAAGTGGGAGCGGCCGCGCTTTTTTTTTTTTTTTTTT 3'], double-stranded cDNA was size selected, ligated to Eco RI adapters (Pharmacia), digested with Not I and cloned into the Not I and Eco RI sites of a modified pT7T3 vector (Pharmacia). The retinas were obtained from a 55 year old Caucasian and total cellular poly(A)+ RNA was extracted 6 hrs after their removal. The retina RNA was kindly provided by Roderick R. McInnes M.D. Ph.D. from the University of Toronto. Library constructed by Bento Soares and M. Fatima Bonaldo." /clone="361374" /clone_lib="Soares retina N2b4HR" /sex="male" /tissue_type="retina" /dev_stage="55 year old" /lab_host="DH10B (ampicillin resistant)" |
| mRNA | complement(<1..>241) |
| BASE COUNT | 31 a    84 c    82 g    37 t    7 others |
| ORIGIN |  |

```
    1 gcggccgcgg nggntgcagc tccangnagg gggtctgagt cgcctgtcac catttncagg
   61 gctgggaacg ccggagagtt ggtctctccc cttctactgc ctccaacacg gcggcngcgg
  121 cggcggcaca tccagggacc cgggccggtt ttaaacctcc cgtccgccgc cgccgcaccc
  181 cccagtggcc cgggctccgg agnccgcctg gcggaggcaa gccgttcgga gggattattc
  241 g
//
```

TABLE 31

| LOCUS | H84024    405 bp    mRNA    EST    13-NOV-1995 |
|---|---|
| DEFINITION | yv88c10.r1 Homo sapiens CDNA clone 249810 5'. |
| ACCESSION | H84024 |
| NID | g1062695 |
| KEYWORDS | EST. |
| SOURCE | human clone=249810 primer=M13RP1 library=Soares melanocyte 2NbHM vector=pT7T3D (Pharmacia) with a modified polylinker host=DH10B (ampicillin resistant) Rsitel=Not I Rsite2=Eco RI 1st strand cDNA was primed with a Not I - oligo(dT) primer [5' TGTTACCAATCTGAAGTGGGAGCGGCCGCGGTTTTTTTTTTTTTTTTTT 3'], double-stranded cDNA was size selected, ligated to Eco RI adapters (Pharmacia), digested with Not I and cloned into the Not I and Eco RI sites of a modified pT7T3 vector (Pharmacia). Library constructed by Bento Soares and M. Fatima Bonaldo. |
| ORGANISM | Homo sapiens Eukaryotae; Metazoa; Eumetazoa; Bilateria; Coelomata; Deuterostomia; Chordata; Vertebrata; Gnathostomata; Osteichthyes; Sarcopterygii; Choanata; Tetrapoda; Amniota; Mammalia; Theria; Eutheria; Archonta; Primates; Catarrhini; Hominidae; Homo. |
| REFERENCE | 1 (bases 1 to 405) |
| AUTHORS | Hillier, L., Clark, N., Dubuque, T., Elliston, K., Hawkins, M., Holman, M., Hultman, M., Kucaba, T., Le, M., Lennon, G., Marra, M., Parsons, J., Rifkin, L., Rohlfing, T., Soares, M., Tan, F., Trevaskis, E., Waterston, R., Williamson, A., Wohldmann, P. and Wilson, R. |
| TITLE | The Washu-Merck EST Project |
| JOURNAL | Unpublished (1995) |
| COMMENT | Contact: Wilson RK WashU-Merck EST Project Washington University School of Medicine 4444 Forest Park Parkway, Box 8501, St. Louis, MO 63108 Tel: 314 286 1800 Fax: 314 286 1810 Email: est@watson.wustl.edu High quality sequence stops: 271 Source: IMAGE Consortium, LLNL This clone is available royalty-free through LLNL; contact the |

TABLE 31-continued

| | |
|---|---|
| | IMAGE Consortium (info@image.llnl.gov) for further information. |
| FEATURES | Location/Qualifiers |
| source | 1..405 |
| | /organism="Homo sapiens" |
| | /clone="249810" |
| mRNA | <1..>405 |
| BASE COUNT | 110 a    77 c    69 g    139 t    10 others |
| ORIGIN | |

```
  1 ttacaattga gaaaacatat ttaataaatc attgtcaatt tttataatgt ttcaagccca
 61 ttctttgttg atagcctcca catttatatg gttaagtcat tgttgctgtg tttcttacct
121 atgacattat ttttatatcc cttcatttgt ggatcttaag atgttgcaga aggttcattc
181 ctgtacccca atacagnttc acttccttta gctgcctttt ctagcaccaa tatgctttaa
241 aaaaaaantg cgcaaacaac aagcagtgac agcggccaat tcctcgattg tccngattaa
301 tanctgtagc atgctaaagg aaggtgtgtg taaataggct ggagatgggt atatggntcc
361 agagtccagc tgaanattgt ntccttnctg agcnttccct ncatt
```
//

TABLE 32

| | |
|---|---|
| LOCUS | T60154    473 bp    mRNA    EST    09-FEB-1995 |
| DEFINITION | yc22c07.s1 Homo sapiens cDNA clone 81420 3'. |
| ACCESSION | T60154 |
| NID | g661991 |
| KEYWORDS | EST. |
| SOURCE | human clone=81420 library=Stratagene lung (#937210) |
| | vector=pBluescript SK- host=SOLR cells (kanamycin resistant) |
| | primer=-21m13 Rsite1=EcoRI Rsite2=XhoI Normal lung tissue from a 72 |
| | year old male. Cloned unidirectionally. Primer: oligo dT. Average |
| | insert size: 1.0 kb; Uni-ZAP XR Vector; 5' adaptor sequence: |
| | 5'-GAATTCGGCACGAG-3'; 3' adaptor sequence: |
| | 5 '-CTCGAGTTTTTTTTTTTTTTTTT-3'. |
| ORGANISM | Homo sapiens |
| | Eucaryotae; Metazoa; Chordata; Vertebrata; Gnathostornata; Mammalia; |
| | Eutheria; Primates; Catarrhini; Hominidae; Homo. |
| REFERENCE | 1 (bases 1 to 473) |
| AUTHORS | Hillier, L., Clark, N., Dubuque, T., Elliston, K., Hawkins, M., |
| | Holman, M., Hultman, M., Kucaba, T., Le, M., Lennon, G., Marra, M., |
| | Parsons, J., Rifkin, L., Rohlfing, T., Tan, F., Trevaskis, E., |
| | Waterston, R., Williamson, A., Wohldmann, P. and Wilson, R. |
| TITLE | WashU-Merck EST Project |
| JOURNAL | Unpublished (1995) |
| COMMENT | Contact: Wilson RK |
| | WashU-Merch EST Project |
| | Washington University School of Medicine |
| | 4444 Park Parkway, Box 8501, St. Louis, MO 63108 |
| | Tel: 314 286 1800 |
| | Fax: 314 286 1810 |
| | Email: est@watson.wustl.edu |
| | High qality sequence stops: 398 |
| | Source: IMAGE Consortium, LLNL |
| | This clone is available royalty-free through LLNL; contact the |
| | IMAGE Consortium (info@image.llnl.gov) for further information. |
| FEATURES | Location/Qualifiers |
| source | 1..473 |
| | /organism="Homo sapiens" |
| | /clone="81420" |
| BASE COUNT | 147 a    79 c    90 g    154 t    3 others |
| ORIGIN | |

```
  1 anagttngtg tgcagcatta caaaatattt tatatttaat gagaaaaaag aagcttgcag
 61 gcagcacatg aagcatccac agcaggtatt atgattgaaa actagtaaaa taagtgtaag
121 ttgttgactg atgtaggtac taacagcatc tgaattttag cactggcctt gattacacag
181 gagatggaga agtcgttaca attgagaaaa catatttaat aaatcattgt caattttat
241 aatgtttcaa gcccattctt tgttgatagc ctccacattt atatgggtta agtcattgtt
301 gctgtgtttc ttacctatga cattatttt atatcccttc atttgtggga tcttaaggat
361 gttgcaggaa gggttcattc cctgtaccc caatacagat tcacttcctt taggctgcct
421 tttctaggca ccaatatgct ttaaaaaaaa atggcggcaa acaacaggcn gtg
```
//

TABLE 33

| | |
|---|---|
| LOCUS | T60214    396 bp    mRNA    EST    09-FEB-1995 |
| DEFINITION | yc22c07.r1 Homo sapiens cDNA clone 81420 5'. |
| ACCESSION | T6O214 |
| NID | g662091 |

TABLE 33-continued

| | |
|---|---|
| KEYWORDS | EST. |
| SOURCE | human clone=81420 library=Stratagene lung (#937210) vector~pBluescript SK- host=SOLR cells (kanamycin resistant) primer=M13RP1 Rsite1=EcoRI RsiteZ=Xhol Normal lung tissue from a 72 year old male. Cloned unidirectionally. Primer: Oligo dT Average insert size: 1.0 kb: Uni-ZAF XR Vector; 5' adaptor sequence: 5'-GAATTCGGCACGAG-3'; 3' adaptor sequence: 5'-CTCGAGTTTTTTTTTTTTTTTTT-3' |
| ORGANISM | Homo sapiens Eucaryotae; Metaazoa; Chordata; vertebrata; Gnathostomata; Mammalia; Eutheria; Primate=; Catarrhini; Hominidae; Homo. |
| REFERENCE | ι (bases 1 to 396) |
| AUTHORS | Hillier, L., Clark, N., Dubuque, T., Elliston, K., Hawkins, M., Holman, M., Hultman, M., Kucaba, T., Le, M., Lennon, G., Marra, M., Parsons, J., Rifkin, L., Rohlfing, T., Tan, F., Trevaskis, E., Waterston, R., Williamson, A., Wohldmann, P. and Wilson, R. |
| TITLE | WashU-Merck EST Project |
| JOURNAL | Unpublished (1995) |
| COMMENT | Contact: Wilson RK Washu-Merck EST Project Washington University School of Medictne 4444 Forest Park Parkway, Box 8501, St. Louis, MO 63108 Tel: 314 286 1800 Fax: 314 286 1810 Email: est@watson.wustl.edu High qality sequence stops: 242 Source: IMAGE Consortium, LLNL This clone is available royalty-tree through LLNL; contact the IMAGE Consortium (info@image.llnl.gov) for further information. |
| FEATURES | Location/Qualifiers |
| source | 1..396 /organism="Homo sapiens" /clone="81420" |
| BASE COUNT | 119 a    15 c    74 g    126 t    2 others |
| ORIGIN | |

```
  1 tcaaatccag aggctagcag ttcaacttct gtaacaccag atgttagtga caatgaacct
 61 gatcattata gatattctga caccactgac tctgatccag agaatgaacc ttttgatgaa
121 gatcagcata cacaaattac aaaagtctga attttttttt atcaagaggg ataaaacacc
181 atgaaaataa acttgaataa actgaaaatg ggaccttttt ttttttttaat gggcaatagg
241 gacattgtgt caggattacc agttataggg gacaattctc ttttccctgg acccaatctt
301 gttttttacc ctatacatcc accgggggtt ttttgacact tgtttgtccc agttggaaaa
361 agggttgtnt tggccgtngt ccaggattat accctt
//
```

TABLE 34

| | |
|---|---|
| LOCUS | R29457    224 bp    mrNA    EST    25-APR-1995 |
| DEFINITION | F1-578D 22 week old human fetal liver cDNA library Homo sapiens cDNA clone F1-578D 5'. |
| ACCESSION | R29457 |
| NID | g1511865 |
| KEYWORDS | EST. |
| SOURCE | human. |
| ORGANISM | Homo sapiens Eukaryotae; mitochondrial eukaryotes; Metazoa; Chordata; Vertebrata; Eutheria; Primates; Catarrhini; Hominidae; Homo. |
| REFERENCE | 1 (bases 1 to 224) |
| AUTHORS | Choi, S. S., Yun, J. W., Choi, E. K., Cho, Y. G., Sung, Y. C. and Shin, H. -S. |
| TITLE | Construction of a gene expression profile of a human fetal liver by single-pass cDNA sequencing |
| JOURNAL | unpublished (1995) |
| COMMENT | Contact: Hee-Sup Shin Developmental Genetics Pohang Institute of Science & Technology San31, Hyojadong Pohang, 794-784 Republic of Korea Tel: 562-279-2291 Fax: 562-279-2199 Email: shinhs@vision.postech.ac.kr Seq primer: T3 primer. |
| FEATURES | Location/Qualifiers |
| source | 1..224 |

TABLE 34-continued

```
                /organism = "Homo sapiens"
                /note = "Vector: pBluescriptII SK(-); Site_1: EcoRI; Site_2:
                /XhoI; The cDNA librabry made by oligo-dT primed and
                directionally cloned between 5 'ExoR I-XhoI3' sites."
                /clone = "F1-578D"
                /clone_lib = "22 week old human fetal liver cDNA library"
                /lab_host = "XL1-blue MRF⁻" mRNA    <1..>224
BASE COUNT      45 a      78 c      67 g      34 t
ORIGIN
    1    gggctccgga    gccgccgcg    gaggcagccg    ttcggaggat    tattcgtctt    ctccccattc
   61    cgctgccgcc    gctgccaggc    ctctgctgct    gaggagaagc    aggcccagtc    gctgcaacca
  121    tccagcagcc    gccgcagcag    ccattacccg    gctgcggtcc    agagccaaga    cgcagagagg
  181    gcatcagcta    ccgccaagtc    agagcatttc    catctcagaa    gaag
//
```

TABLE 35

| LOCUS | C01610 | 154 bp | DNA | EST | 11-JUL-1996 |
|---|---|---|---|---|---|
| DEFINITION | HUMGS0008618, Human Gene Signature, 3'-directed CDNA sequence. | | | | |
| ACCESSION | C01610 | | | | |
| NID | g1433840 | | | | |
| KEYWORDS | Gene Signature; GS; EST(expressed sequence tag); BodyMap; gene expression. | | | | |
| SOURCE | One or more human adult tissue. | | | | |
| ORGANISM | Homo sapiens Eukaryotae; mitochondrial eukaryotes; Metazoa; Chordata; Vertebrata; Mammalia; Eutheria; Primates; Catarrhini; Hominidae; Homo. | | | | |
| REFERENCE | 1 (bases 1 to 154) | | | | |
| AUTHORS | Okubo, K. | | | | |
| TITLE | BodyMap; human gene expression database | | | | |
| JOURNAL | Unpublished (1995) | | | | |
| REFERENCE | 2 (bases 1 to 154) | | | | |
| AUTHORS | Okubo, K. | | | | |
| TITLE | Direct Submission | | | | |
| JOURNAL | Submitted (28-DEC-1995) to the DDBJ/EMBL/GenBank databases. Kousaku Okubo, Osaka University, Institute for Molecular and Cellular Bio; 1-3, Yamada-oka, Suita, Osaka Pref. 565, Japan (E-mail:kousaku@imcb.osaka-u.ac.jp, Tel: 06-877-5111(ex.3315), Fax: 06-877-1922) | | | | |
| COMMENT | We are not submitting the same cDNA sequence redundantly to DDBJ since 1993. For the abundance information of clones with this sequence in this library and as well as in other 3'-directed libraries, see ' http://www.imcb.osaka-u.ac.jp/bodymap'. The sequences of the clones represented by this GS sequences is also found there. | | | | |
| FEATURES | Location/Qualifiers | | | | |
| source | 1..154 /organism="Homo sapiens" | | | | |
| BASE COUNT | 67 a      19 c      25 g      41 t      2 others | | | | |

```
ORIGIN
    1 gatccacaaa tgaaagggat ataaaaataa tgtcataggt aagaaacaca gcaacaatga
   61 cttaaccata taaatgtgga ggctatcaac aaagaatggg cttgaaacat tataaaantt
  121 gacaatgatt tattaaatat gtttnctcaa ttgt
//
```

TABLE 36

| LOCUS | AA001098 | 360 bp | mRNA | EST | 18-JUL-1996 |
|---|---|---|---|---|---|
| DEFINITION | ze47h06.r1 Soares retina N2b4HR Homo sapiens CDNA clone 362171 5'. | | | | |

TABLE 36-continued

| | |
|---|---|
| ACCESSION | AA001098 |
| NID | g1437167 |
| KEYWORDS | EST. |
| SOURCE | human. |
|     ORGANISM | Homo sapiens |
| | Eukaryotae; mitochondrial eukaryotes; Metazoa; Chordata; |
| | Vertebrata; Eutheria; Primates; Catarrhini; Hominidae; |
| | Homo. |
| REFERENCE | 1 (bases 1 to 360) |
|     AUTHORS | Hillier, L., Clark, N., Dubuque, T., Elliston, K., |
| | Hawkins, M., |
| | Holman, M., Hultman, M., Kucaba, T., Le, M., Lennon, G., |
| | Marra, M., |
| | Parsons, J., Rifkin, L., Rohlfing, T., Soares, M., Tan, F., |
| | Trevaskis, E., Waterston, R., Williamson, A., Wohldmann, P. |
| | and |
| | Wilson, R. |
|     TITLE | The Washu-Merck EST Project |
|     JOURNAL | Unpublished (1995) |
| COMMENT | Contact: Wilson RK |
| | Washu-Merck EST Project |
| | Washington University School of Medicine |
| | 4444 Forest Park Parkway, Box 8501, St. Louis, MO 63108 |
| | Tel: 314 286 1800 |
| | Fax: 314 286 1810 |
| | Email: est@watson.wustl.edu |
| | This clone is available royalty-free through LLNL; |
| | contact the |
| | IMAGE Consortium (info@image.llnl.gov) for further |
| | information. |
| | Seq primer: mob.REGA+ET |
| | High quality sequence stop: 225. |
| FEATURES | Location/Qualifiers |
|     source | 1..360 |
| | /organism="Homo sapiens" |
| | /note="Organ: eye; Vector: pT7T3D (Pharmacia) with a |
| | modified polylinker; Site_1: Not I; Site_2: Eco RI; 1st |
| | strand cDNA was prirned with a Not I - oligo(dT) primer |
| | [5' |
| | TGTTACCAATCTGAAGTGGGAGCGGCCGCGCTTTTTTTTTTTTTTTTTTT 3'], |
| | double-stranded cDNA was size selected, ligated to Eco RI |
| | adapters (Pharmacia), digested with Not I and cloned into |
| | the Not I and Eco RI sites of a modified pT7T3 vector |
| | (Pharmacia). The retinas were obtained from a 55 year old |
| | Caucasian and total cellular poly(A)+ RNA was extracted |
| | 6 hrs after their removal. The retina RNA was kindly |
| | provided by Roderick, R. McInnes M.D. Ph.D. from the |
| | University of Toronto. Library constructed by Bento |
| | Soares and M. Fatima Bonaldo." |
| | /clone="362171" |
| | /clone_lib="Soares retina N2b4HR" |
| | /sex="male" |
| | /tissue_type="retina" |
| | /dev_stage="55 year old" |
| | /lab_host="DH10B (ampicillin resistant)" |
|     mRNA | <1. .> 360 |
| BASE COUNT | 118 a    55 c    63 g    118 t    6 others |
| ORIGIN | |

```
  1 tagaatctca aattgaaaat ttctgtgcag cattacaaaa tattttatat ttaatgagaa
 61 aaaagaagct tgcaggcagc acatgaagca tccacagcag gtattatgat tgaaaactag
121 taaaataagt gtaagttgtt gactgatgta ggtactaaca gcatctgaat tttagcactg
181 gccttgatta cacaggagat ggagaagtcg ttacaattga gaaacatat ttaataaatc
241 attgtcaatt nttaataatg gtttcaagcc catncttng ttgatagcct ccnccatttt
301 atatcggtta agtcattggg tgctngtgtt tcttacctat gaccattatn tttatatccc
//
```

TABLE 37

| | |
|---|---|
| LOCUS | R58391     150 bp     mRNA     EST     02-MAY-1996 |
| DEFINITION | G3334 Fetal heart Homo sapiens CDNA clone G3334 5' end. |
| ACCESSION | R58391 |
| NID | g828449 |
| KEYWORDS | EST. |
| SOURCE | human. |
|     ORGANISM | Homo sapiens |

TABLE 37-continued

|  |  |
|---|---|
|  | Eukaryotae; mitochondrial eukaryotes; Metazoa; Chordata; Vertebrata; Eutheria; Primates; Catarrhini; Hominidae; Homo. |
| REFERENCE | 1 (bases 1 to 150) |
| AUTHORS | Hwang, D. M., Fung, Y. W.. Wang, R.X., Laurenssen, C. M., Ng, S. H., Lam, W. Y., Tsui, K. W., Fung, K. P., Waye, M., Lee, C. Y. and Liew, C. C. |
| TITLE | Analysis of expressed sequence tags from a fetal human heart cDNA library |
| JOURNAL | Genomics 30 (2), 293–298 (1995) |
| COMMENT | Contact: Liew CC<br>Molecular Cardiology<br>University of Toronto<br>Banting Institute, 100 College St., Toronto, Ontario, M5G1L5<br>Tel: 4169788758<br>Fax: 4169785650<br>Email: liewcc@utcc.utoronto.ca<br>Seq primer: GGTGGCGACGACTCCTGGAGCC. |
| FEATURES | Location/Qualifiers |
| source | 1..150<br>/organism="Homo sapiens"<br>/note="vector: Lambda gt22; Site_1: NotI; Site_2: SalI; mRNA was purified from human fetal hearts (10–12 weeks). cDNA was constructed using a NotI-Oligo dT adaptor-primer.<br>SalI adaptors were ligated, followed by digestion with NotI, for direction cloning into predigested lambda gt22. Method is described in J. Mol. Cell. Cardiol. (1994) 26, 1329–1333)"<br>/clone="G3334"<br>/clone_lib="Fetal heart"<br>/lab_host="E. coli Y1090" |
| mRNA | <1..>150 |
| BASE COUNT | 51 a    23 c    29 g    47 t |
| ORIGIN |  |

```
  1 atgacctttg atgagatcag catacacaaa tacaaaagtc tgagtttttt tttatcagga
 61 gggataaaca ccatgaaata aacttgaata aactgaaaat ggacctttt tttttaatgg
121 cataggcatg ggcgttcccg tttggacaat
//
```

Location and nature of sequences shown in the Sequence Listing

| SEQ ID No | Page | Description |
|---|---|---|
| 1 | 34, 69 | primer for microsatellite marker |
| 2 | 34, 69 | primer for microsatellite marker |
| 3 | 34, 69 | primer for microsatellite marker |
| 4 | 34, 69 | primer for microsatellite marker |
| 5 | 34, 70 | primer for microsatellite marker |
| 6 | 34, 70 | primer for microsatellite marker |
| 7 | 52 | primer for exon amplification |
| 8 | 52 | primer for exon amplification |
| 9 | 70 | blood (normal) sequence |
| 10 | 70 | tumour (mutated) sequence |
| 11 | 50 (FIG. 6) | cDNA sequence |
| 12 | 50 (FIG. 7) | translation of cDNA sequence |
| 13 | 50 (FIG. 8) | gene corresponding to IMAGE 264611: exon and flanking sequence |
| 14 | 50 (FIG. 9) | gene corresponding to IMAGE 264611: exon and flanking sequence |
| 15 | 50 (FIG. 10) | gene corresponding to IMAGE 264611: exon and flanking sequence |
| 16 | 50 (FIG. 11) | gene corresponding to IMAGE 264611: exon and flanking sequence |
| 17 | 50 (FIG. 12) | gene corresponding to IMAGE 264611: exon and flanking sequence |
| 18 | 50 (FIG. 13) | gene corresponding to IMAGE 264611: exon and flanking sequence |
| 19 | 50 (FIG. 14) | gene corresponding to IMAGE 264611: exon and flanking sequence |
| 20 | 50 (FIG. 15) | gene corresponding to IMAGE 264611: exon and flanking sequence |
| 21 | 8 | modified polylinker |
| 22 | 9 (Table 3) | AA009519 IMAGE 365465 (5') |
| 23 | 9 (Table 4) | AA009520 IMAGE 365465 (3') |
| 24 | 9 (Table 5) | AA017563 IMAGE 361374 (3') |
| 25 | 9 (Table 6) | C01084 |
| 26 | 9 (Table 7) | H92038 IMAGE 221326 (5') |
| 27 | 9 (Table 8) | H92039 IMAGE 221326 (3') |
| 28 | 9 (Table 9) | N20238 IMAGE 264611 (3') |
| 29 | 9 (Table 10) | N29304 IMAGE 264611 (5') |
| 30 | 9 (Table 11) | N35389 IMAGE 272092 (3') |
| 31 | 9 (Table 12) | N48030 IMAGE 272092 (5') |
| 32 | 9 (Table 13) | R06763 IMAGE 126556 (3') |
| 33 | 9 (Table 14) | R06814 IMAGE 126556 (5') |
| 34 | 9 (Table 15) | R29457 F1-578D (5') |
| 35 | 9 (Table 16) | T05157 HFBCS42 |
| 36 | 9 (Table 17) | T60214 IMAGE 81420 (5') |
| 37 | 9 (Table 18) | W23656 IMAGE 306632 |
| 38 | 9 (Table 19) | W27533 |
| 39 | 9 (Table 20) | W30684 IMAGE 309597 (5') |
| 40 | 9 (Table 21) | W81026 IMAGE 347316 (5') |
| 41 | 9 (Table 22) | W81062 IMAGE 347316 (3') |
| 42 | 9 (Table 23) | AA039223 IMAGE 486093 (5') |
| 43 | 9 (Table 24) | C17744 552A05 |
| 44 | 9 (Table 25) | W37864 IMAGE 322160 (3') |

-continued

Location and nature of sequences shown in the Sequence Listing

| SEQ ID No | Page | Description |
|---|---|---|
| 45 | 9 (Table 26) | W37855 IMAGE 322160 (5') |
| 46 | 9 (Table 27) | M78282 HFBBA34 |
| 47 | 9 (Table 28) | N98421 IMAGE 309597 (3') |
| 48 | 10 (Table 29) | AA017584 IMAGE 361374 (5') |
| 49 | 10 (Table 30) | AA017563 IMAGE 361374 (3') |
| 50 | 10 (Table 31) | H84024 IMAGE 249810 (5') |
| 51 | 10 (Table 32) | T60154 IMAGE 81420 (3') |
| 52 | 10 (Table 33) | T60214 IMAGE 81420 (5') |
| 53 | 10 (Table 34) | R29457 F1-578D (5') |
| 54 | 10 (Table 35) | C01610 |
| 55 | 10 (Table 36) | AA001098 IMAGE 362171 (5') |
| 56 | 10 (Table 37) | R58391 G3334 (5') |
| 57 | 50 (FIG. 9) | gene corresponding to IMAGE 264611: exon 2B and flanking sequence |
| 58 | 50–51 (FIG. 16) | gene corresponding to IMAGE 264611: exon and flanking sequence |
| 59 | 50–51 (FIG. 17) | gene corresponding to IMAGE 264611: exon and flanking sequence |
| 60 | 50–51 (FIG. 18) | gene corresponding to IMAGE 264611: exon and flanking sequence |
| 61 | 50 (Table 37) | pcr primer (EST) |
| 62 | 50–51 (FIG. 19) | gene corresponding to IMAGE 264611: exon and flanking sequence |
| 63 | 50–51 (FIG. 19) | gene corresponding to IMAGE 264611: exon and flanking sequence |
| 64 | 50–51 (FIG. 20) | gene corresponding to IMAGE 264611: exon and flanking sequence |
| 65 | 50–51 (FIG. 21) | gene corresponding to IMAGE 264611: exon and flanking sequence |
| 66 | 50–51 (FIG. 22) | gene corresponding to IMAGE 264611: exon and flanking sequence |
| 67 | 50–51 (FIG. 23) | gene corresponding to IMAGE 264611: exon and flanking sequence |
| 68 | 50–51 (FIG. 24) | gene corresponding to IMAGE 264611: exon and flanking sequence |
| 69 | 70 | blood (normal) sequence |
| 70 | 70 | tumour (mutated) sequence |
| 71 | 71 | blood (normal) sequence |
| 72 | 71 | tumour (mutated) sequence |
| 73 | 71 | blood (normal) sequence |
| 74 | 71 | tumour (mutated) sequence |
| 75 | 72 | peptide antigen |
| 76 | 72 | peptide antigen |
| 77 | 72 | peptide antigen |
| 78 | 50 (Table 3, 4, 21, 22) | pcr primer (EST) |
| 79 | 50 (Table 5, 7, 8) | pcr primer (EST) |
| 80 | 50 (Table 9, 10, 11, 12) | pcr primer (EST) |
| 81 | 50 (Table 13, 14) | pcr primer (EST) |
| 82 | 50 (Table 17, 32, 33) | pcr primer (EST) |
| 83 | 50 (Table 17) | pcr primer (EST) |
| 84 | 50 (Table 18) | pcr primer (EST) |
| 85 | 50 (Table 19) | pcr primer (EST) |
| 86 | 50 (Table 19) | pcr primer (EST) |
| 87 | 50 (Table 19) | pcr primer (EST) |
| 88 | 50 (Table 20) | pcr primer (EST) |
| 89 | 50 (Table 23) | pcr primer (EST) |
| 90 | 50 (Table 25, 26) | pcr primer (EST) |
| 91 | 50 (Table 28) | pcr primer (EST) |
| 92 | 50 (Table 30, 36) | pcr primer (EST) |
| 93 | 50 (Table 31) | pcr primer (EST) |
| 94 | 50 (Table 32, 33) | pcr primer (EST) |

REFERENCES

1. Cannon-Albright, L., and Eeles, R. (1995) "Progress in prostate cancer" *Nature Genet.* 9, 336–338.
2. Lundgren, R., Mandahl, N., Heim, S., Limon, J., Henrikson, H., and Mitelman, F. (1992) "Cytogenetic analysis of 57 primary prostatic adenocarcinomas" *Genes Chrom. Cancer* 4, 16–24.
3. Arps, S., Rodewald, A., Schmalenberger, B., Carl, P., Bressel, M., and Kastendieck, H. (1993) "Cytogenetic survey of 32 cancers of the prostate" *Cancer Genet. Cogenet.* 66, 93–99.
4. Zervos, A. S., Gyuris, J., and Brent, R. (1993) "Mxil, a protein that specifically interacts with Max to bind Myc-Max recognition sites" *Cell* 72, 223–232.
5. Eagle, L. R., Yin, X., Brothman, A. R., Williams, B. J., Atkin, N. B., and Prochownick, E. V. (1995) "Mutation of the Mxil gene in prostate cancer" *Nature Genet.* 9, 249–255.
6. Phillips, S. M. A., Morton, D. G., Lee, S. J., Wallace, D. M. A., and Neoptolemos, J. P. (1994) "Loss of heterozygosity of the retinoblastoma and adenomatous polyposis susceptibility gene loci and in chromosomes 10p, 10q, and 16q in human prostate cancer" *Br. J. Urol.* 73, 390–395.
7. Gyapay, G., Morissette, J., Vignal, A., Dib, C., Fizames, C., Millasseau, P., Marc, S., Bernadi, G., Lathrop, M., and Weissenbach, J. (1994) "The 1993–1994 Genethon human genetic linkage map" *Nature Genetics* 7, 246–339.
8. Orita, M., Iwahana, H., Kanazawa, H., Hayashi, K., and Sekiya, T. (1989) "Detection of polymorphisms of human DNA by gel electrophoresis as single-strand conformation polymorphisms" *Proc. Natl. Acad, Sci. USA* 86, 2766–2770.
9. UICC (Union Internationale Contre Le Cancer). TNM Classification of malignant tumours. Geneva: International Union Against Cancer, 1978.
10. Parsons, R., Li, G.-M., Longley, M. J., Fang, W., Papadopoulos, N., Jen, J., de la Chapelle, A., Kinzier, K. W., Vogelstein, B., and Modrich, P. (1993) "Hypermutability and mismatch repair deficiency in RER+tumour cells" *Cell* 75, 1227–1236.
11. Gray, I. C., Nobile, C., Moresu, R., Ford, S., and Spurr, N. K. (1995) "A 2.4 megabase physical map spanning the CYP2C gene cluster on chromosome 10q24" *Genomics* 28, 328–332.
12. Rocchi, M., Covone, A., Romeo, G., Faraonio, R., and Colantuoni, V. (1989) "Regional mapping of RBP4 to 10q23-24 and RBP1 to 3q21-22 in man" *Somat. Cell Molec. Genet.* 15, 185–190.
13. Inoue, K., Inazawa, J., Suzuki, Y., Shimada, T., Yamazaki, H., Guengerich, F. P., and Abe, T. (1994) "Fluorescence in-situ hybridization analysis and chromosomal localization of 3 human cytochrome-p450-2c genes (cyp2c8, 2c9 and 2c10) at 10q24.1" *Jpn. J. Hum. Genet.* 39, 337–343.
14. Cohen, D., Chumakov, I., and Weissenbach, J. (1993) "A first generation physical map of the human genome" *Nature* 366, 698–701.
15. Parmiter, A. H., Balaban, G., Clark, W. H. J., and Nowell, P. C. (1988) "Possible involvement of the chromosome region 10q24-q26 in early stages of melanocytic neoplasia" *Cancer Genet. Ctogenet.* 30, 313–317.
16. Ransom, D. T., Rifland, S. R., Moertel, C. A., Dahl, R. J., O'Fallon, J. R., Scheithauer, B. W., Kimmel, D. W., Kelly, P. J., Olopade, O. I., Diaz, M. O., and Jenkins, R. B. (1992) "Correlation of cytogenetic analysis and loss of heterozygosity studies in human difuse astrocytomas and mixed oligo-atrocytomas" *Genes Chrom. Cancer* 5, 357–374.
17. Rasheed, B. K. A., Fuller, G. N., Friedman, A. H., Bigner, D. D., and Bigner, S. H. (1992) "Loss of het erozygosity for 10q loci in human gliomas" *Genes Chrom. Cancer* 5, 75–82.
18. Speaks, S. L., Sanger, W. G., Masih, A. S., Harrington, D. S., Hess, M., and Armitage, J. O. (1992) "Recurrent abnormalities of chromosome bands 10q23-q25 in non-Hodgkins lymphoma" *Genes Chrom. Cancer* 5, 239–243.
19. Fults, D., and Pedone, C. (1993) "Deletion mapping of the long arm of chromosome 10 in glioblastoma multiforme" *Genes Chrom. Cancer* 7, 173–177.
20. Karlbom, A. E., James, C. D., Boethius, J., Cavenee, W. K., Collins, V. P., Nordenskjold, M., and Larsson, C. (1993) "Loss of heterozygosity in malignant gliomas involves at least three distinct regions on chromosome 10" *Hum. Gene.* 92, 169–174.
21. Herbst, R. A., Weiss, J., Enlis, A., Cavanee, W. K., and Arden, K. C. (1994) "Loss of heterozygosity for 10q22-10qter in malignant melanoma progression" *Cancer Res.* 54, 3111–3114.

What is claimed is:

1. A mammalian expression vector adapted to express a protein encoded by the sequence of FIG. 6 (SEQ ID NO:11).

2. The expression vector of claim 1, comprising the nucleotide sequence of FIG. 6 (SEQ ID NO:11).

3. The expression vector of claim 1, further defined as encoding the amino acid sequence of FIG. 7 (SEQ ID NO:12).

4. The expression vector of claim 1, wherein the vector comprises regulatory control sequences recognized by a human cell, and expression of said protein is under the control of said regulatory control sequences.

5. The expression vector of claim 4, wherein the regulatory control sequences comprise a viral promoter.

6. The expression vector of claim 5, wherein the viral promoter is a Rous sarcoma virus LTR.

7. The expression vector of claim 5, wherein the viral promoter is an adenovirus major late promoter.

8. The expression vector of claim 4, wherein the regulatory control sequence comprises an enhancer sequence.

9. The expression vector of claim 4, wherein the regulatory control sequence comprises an inducible promoter.

10. The expression vector of claim 1, further comprising a gene that encodes a selectable trait.

11. The expression vector of claim 10, wherein the gene encoding a selectable trait is a gene encoding antibiotic resistance.

12. The expression vector of claim 1, further defined as a plasmid.

13. The expression vector of claim 1, further defined as a viral vector.

14. The expression vector of claim 13, further defined as an adenoviral vector.

15. The expression vector of claim 13, further defined as an integrating vector.

16. The expression vector of claim 15, further defined as a retroviral vector.

17. The expression vector of claim 13, wherein the vector is an ectotropic virus.

18. The expression vector of claim 13, wherein the vector is an amphotropic virus.

19. A composition comprising the expression vector of any one of claims 1, 2, or 3–18, in combination with a pharmaceutically acceptable excipient or diluent.

20. A host cell comprising the expression vector of claim 1.

21. The host cell of claim 20, further defined as an animal cell.

22. The host cell of claim 21, further defined as a COS-1 cell.

23. A vector adapted for introduction and replication in a mammalian host cell, the vector including a sequence which is at least 50% of the length of the sequence of FIG. 6 (SEQ ID NO:11).

24. The vector of claim 23, further defined as including a sequence which is at least 75% of the length of the sequence of FIG. 6 (SEQ ID NO:11).

25. The vector of claim 24, further defined as including a sequence which is at least 95% of the length of the sequence of FIG. 6 (SEQ ID NO:11).

26. A vector adapted for introduction and replication in a mammalian host cell, the vector comprising a nucleotide sequence encoding a protein encoded by the sequence of FIG. 6 (SEQ ID NO:11).

27. The vector of claim 26, wherein the nucleotide sequence is defined as the nucleotide sequence of FIG. 6 (SEQ ID NO:11).

28. The vector of claim 27, comprising a nucleotide sequence encoding the amino acid sequence of FIG. 7 (SEQ ID NO:12).

29. The vector of claim 23, further defined as a mammalian expression vector.

30. The vector of claim 23, further comprising a gene encoding a selectable marker.

* * * * *